US006355803B1

(12) United States Patent
Natrajan et al.

(10) Patent No.: US 6,355,803 B1
(45) Date of Patent: Mar. 12, 2002

(54) NEAR INFRARED CHEMILUMINESCENT ACRIDINIUM COMPOUNDS AND USES THEREOF

(75) Inventors: Anand Natrajan, Manchester, NH (US); Qingping Jiang, Northborough, MA (US); David Sharpe, Foxborough, MA (US); Say-Jong Law, Westwood, MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/371,489

(22) Filed: Aug. 10, 1999

Related U.S. Application Data

(60) Provisional application No. 60/096,073, filed on Aug. 11, 1998.

(51) Int. Cl.[7] ................ C07D 219/04; G01N 33/532; C07K 17/06
(52) U.S. Cl. .................. 546/102; 435/6; 435/7.1; 435/7.5; 435/188; 436/500; 436/526; 436/544; 530/391.5; 530/402; 530/404; 530/405; 530/812; 544/238; 544/247; 544/343; 546/61; 546/65; 546/70; 546/104
(58) Field of Search ................ 436/544, 500, 436/526; 435/6, 7.1, 7.5, 188; 546/102, 104, 70, 65, 61; 544/238, 343, 247; 530/402, 812, 391.5, 404, 405

(56) References Cited

U.S. PATENT DOCUMENTS

| | | | |
|---|---|---|---|
| 4,745,181 A | 5/1988 | Law et al. ............... 530/387 |
| 4,918,192 A | 4/1990 | Law et al. ............... 546/104 |
| 4,927,769 A | 5/1990 | Chang et al. ............ 436/518 |
| 4,931,223 A | 6/1990 | Bronstein et al. ........ 252/700 |
| 5,110,932 A | 5/1992 | Law et al. ............... 546/102 |
| 5,227,489 A | 7/1993 | Law et al. ............... 546/23 |
| 5,241,070 A | 8/1993 | Law et al. ............... 546/107 |
| 5,395,752 A | 3/1995 | Law et al. ............... 435/6 |
| 5,449,556 A | 9/1995 | Law et al. ............ 428/402.2 |
| 5,468,646 A | 11/1995 | Mattingly et al. ........ 436/501 |
| 5,538,901 A | 7/1996 | Law et al. ............... 436/501 |
| 5,543,524 A | 8/1996 | Mattingly et al. ........ 546/104 |
| 5,545,739 A | 8/1996 | Mattingly et al. ........ 546/108 |
| 5,565,570 A | 10/1996 | Mattingly et al. ........ 546/108 |
| 5,595,875 A | 1/1997 | Law et al. ............... 435/6 |
| 5,656,207 A | 8/1997 | Woodhead et al. ....... 252/700 |
| 5,656,426 A | 8/1997 | Law et al. ............... 435/6 |
| 5,663,074 A | 9/1997 | Law et al. ............... 436/546 |
| 5,669,819 A | 9/1997 | Mattingly et al. ........ 436/501 |
| 5,702,887 A | 12/1997 | Law et al. ............... 435/6 |
| 5,879,894 A | 3/1999 | Law et al. ............... 435/7.1 |

FOREIGN PATENT DOCUMENTS

| | | | |
|---|---|---|---|
| EP | 0 263 657 A2 | 4/1988 | |
| EP | 0 324 202 A1 | 7/1989 | ............ 219/4 |
| EP | 0 353 971 A2 | 2/1990 | |
| EP | 0 361 817 A2 | 4/1990 | |
| EP | 0 478 626 B1 | 4/1992 | ............ 21/76 |
| EP | 0 609 885 A1 | 8/1994 | ............ 219/4 |
| WO | WO 98/02421 | 1/1998 | |
| WO | WO 98/54574 | 12/1998 | ............ 33/58 |

OTHER PUBLICATIONS

M. Kawaguchi, et al; *Proceedings of 9th International Symposium 1996*; ed. Hastings, et al, 1997, pp. 481–484.
Zomer, et al. "Synthesis, Chemiluminescence, and Stability of Acridinium Ester Labeled Compounds", *Pract. Spectrosc. 1991*, 12 (*Lumin. Tech. Chem. Biochem. Anal.*), 505–521.
Martin, C., et al., *J. Biolumin. & Chemilumin.* 9, (3), 145 (1994).
Edwards, B., et al., *J. Biolumin. & Chemilumin.*, 5, 1 (1990).

*Primary Examiner*—Mary E. Ceperley
(74) *Attorney, Agent, or Firm*—Weingarten, Schurgin, Gagnebin & Lebovici LLP

(57) ABSTRACT

This application relates to long-wavelength acridinium compounds having electron-donating groups, which may either be: (a) Part of an extended conjugation system attached by appropriate functional groups to the acridinium nucleus, with coplanarity of the attached functional group and the acridone moiety during light emission (geometry requirement), said functional group consisting of at least one aromatic ring and one electron-donating atom or group with an extra pair of electrons which can readily delocalize into the extended π system to which the heteroatom is directly attached or built into, and establish stable extended resonance with the electron-withdrawing carbonyl moiety of the light emitting acridone. Such electron-donating atom or group that exists in the form of an anion has particularly strong effect to further the bathochromic shift of the emission wavelength; or (b) directly attached at one or more of positions C-2, C-4, C-5, or C-7 of the acridinium nucleus, of electron-donating atoms or groups having extra pair(s) of electrons. The electron-donating entities can be the same or different if more than one electron-donating entity is used. An electron-donating atom or group that exists in the form of an anion has particularly strong effect to further the bathochromic shift of the emission wavelength.

17 Claims, 13 Drawing Sheets

Schematic Diagram of Dual AE-label Vanco A + B Resistance Gene Assay

Vanco A Assay Reagents

Vanco A 2-OH-DMAE-Probe 526.20

```
   2-OH-
   DMAE
    |
3' NH -TTT ACA CGC TTT TTG GAA CGC  5'
```

Vanco-A PMP-Probe 557.22

```
                                                                                                    (PMP)
                                                                                                      |
                                                                                                      N
5'                  3' TGC TGT TAA CGA TAA GTC GAC TGA TCG AGG AGG AGG AGG AGG AGG AGG- N 5'
5' AA TGT GCG AAA AAC CTT GCG CGG AAT GGG AAA ACG ACA ATT GCT ATT CAG CTG  3'
```

Vanco A Synthetic Target 526.53

Vanco B Assay Reagents

Vanco B DMAE-Probe 459.23

```
  DMAE
    |
3' NH -GT GAC CGG ATG TAA GAA TGT TTT  5'
```

Vanco-B PMP-Probe 496.20

```
                                                                                                    (PMP)
                                                                                                      |
                                                                                                      N
                              3' G CAG GGG CTT AAA GTT TAC T TGA AGG AGG AGG AGG AGG AGG AGG AGG- N 5'
5' CA CTG GCC TAC ATT CTT ACA AAA AAT GCG GGC ATC GCC GTC CCC GAA TTT CAA ATG A  3'
```

Vanco B Synthetic Target 459.57

*FIG. 4*

NEAR INFRARED CHEMILUMINESCENT ACRIDINIUM COMPOUNDS AND USES THEREOF

CROSS REFERENCE TO RELATED APPLICATIONS

This application claims priority under 35 U.S.C. §119(e) to provisional patent application serial No. 06/096,073 filed Aug. 11, 1998, the disclosure of which is hereby incorporated by reference.

FIELD OF THE INVENTION

The present invention relates to novel chemiluminescent acridinium compounds that have emission maxima close to or in the near infrared (NIR) region (>590 nm). The structural requirements for such long wavelength-emitting acridinium compounds are disclosed herein. These novel acridinium compounds when used in conjunction with short wavelength-emitting acridinium esters (with emission maxima below 450 nm) should be highly useful labels for the simultaneous detection of multiple target analytes in immunoassays or nucleic acid assays due to the extremely small or negligible spectral overlap between the different labels. A true and effective optical segregation of the two or more specific signals associated with different analytes can be easily achieved by the use of optical filters in conjunction with a simple algorithmic operation for minor correction of any low level of cross-talk. From practical standpoint, minimal spectral overlap is thus the key factor that is necessary for the simultaneous and accurate measurement of different analytes. A further application of the compounds described here is in situations where there is optical interference from biological samples at short wavelength (under 500 nm). Under these conditions, these novel acridinium compounds should be useful, alternative, labels, permitting the optical separation of non-label related luminescence from the specific, chemiluminescent signal generated front the binding complex. Finally, long-wavelength acridinium compounds used in conjunction with detectors such as CCD cameras offer the potential for improved assay sensitivity since these detectors are remarkably efficient in reading long wavelength signals.

BACKGROUND OF THE INVENTION

Acridinium esters (AE) provide for an extremely sensitive method of detection and are useful chemiluminescent signal molecules that have been used extensively as labels in immunoassays and nucleic acid assays. U.S. Pat. Nos. 4,745,181; 4,918,192; 5,110,932 first described hydrolytically stable Polysubstituted Aryl Acridinium Esters (PAAE) which are useful for analytical measurements and became the first chemiluminescent acridinium compounds that enabled ligand binding assays to meet the stringent conditions required for commercialization owing to their remarkable stability. Subsequently, U.S. Pat. Nos. 5,241,070; 5,538,901; and 5,663074 described nucleophilic PAAE useful for the direct labeling of diverse organic molecules which lack nucleophilic functional groups. The utility of PAAE was further enhanced with the advent of Functionalized Hydrophilic PAAE (U.S. Pat. No. 5,656,426) which increased the quantum yield of PAAE and enhanced the performance of PAAE-labeled binding partners in terms of the observed signal to noise ratios and the sensitivities of various binding assays. This was primarily due to the introduction of hydrophilic group at the acridinium nucleus which increased the aqueous solubility of the compound and also unexpectedly increased the quantum yield of light production. Additionally, introduction of ionizable groups at the phenoxy moiety produced another sub-class of hydrophilic PAAE (U.S. Pat. Nos. 5,227,489; 5,449,556; and 5,595,875) which could be encapsulated in large numbers within biomolecule-functionalized, liposomes with extremely low leakage over prolonged storage. The last application further enhanced the utility of PAAE.

M. Kawaguichi, et al. (Bioluminescence and Chemiluminescence, Proceedings of 9$^{th}$ International Symposium 1996, Ed. Hastings, Kricka and Stanley, John Wiley & Sons, 1997, pp. 480–484) have described stabilized phenyl acridinium esters for chemiluminescent immunoassays. AE derivatives with additional methyl substitutions at C-1, which are optional at C-3 of the acridinium nucleus with matching mono- or di-methyl substitutions at the ortho-positions of the phenoxy moiety, were shown to have excellent stability in aqueous solution.

EP 0324,202 A1 and subsequently EP 0609,885 A1 both describe acridinium esters with functional groups substituted at the nitrogen atom of the acridinium nucleus. The latter application further describes alternate substituents such as the biphenyl or naphthylmoieties as possible replacements for the phenyl group. These types of acridinium compounds are reported to have emission maxima at 420 nm.

Mattingly, et al. (U.S. Pat. Nos. 5,468,646 and 5,543,524) describe chemiluminescent acridinium salts, their methods of preparation, their antibody conjugates, and their applications in immunoassays. These acridinium salts belong to another class of compounds termed acridinium sulfonylamides (or N-sulfonylacridinium carboxamides). The acridinium sulfonylamides (AS) have aqueous stabilities which are comparable with PAAE. No emission maxima were reported for the AS described therein. However, since the same acridone species should be generated from both classes of these compounds during their reaction with alkaline peroxide, the emission maxima for the acridinium sulfonylamides is expected to be in the blue region.

Mattingly, et al. further describe and claim the analogous chemiluminescent phenanthridinium salts, their methods of preparation, their antibody conjugates, and their applications in immunoassays, in U.S. Pat. Nos. 5,545,739; 5,565,570, and 5,669,819. Additionally, in these patents a general structure of acridinium sulfonylamides is described showing possible substitutents of a Markush group at the acridinium nucleus. No particular benefits about the substitutents were stated. None of the AS derivatives depicted by the general structure fits the teachings described by the present invention. Finally, the above patents do not describe any attempt to extend the wavelength of light emission of the acridinium sulfonylamides nor do they outline any strucuture-activity rationale about how this may be achieved.

Conventional acridinium compounds, such as those described in the aforementioned patents and literature, emit light with maxima at about 428 nm upon reaction with hydrogen peroxide in strong alkaline solution. Acridinium compounds which emit light of wavelength maxima >500 nm have also been described in the prior art. U.S. Pat. Nos. 5,395,752; 5,702,887 and 5,879,894 by Law et al. describe novel, long-emission acridinium esters (LEAE), where a fused, benzacridinium system is employed to extend the wavelength of emission of the acridinium ester. In the copending PCT application PCT/IB98/00831, Jiang et al. have further extended the PAAE emission maxima well into the region of 600–700 nm by utilizing the principle of energy transfer. This entailed the covalent coupling of luminophores to acridinium ester. Then the chemiluminescent reactions of these conjugates were initiated by treatment with alkaline peroxide, light emission was observed at long wavelengths where the wavelength maxima depended upon the structure of the luminophore.

EP 0 478 626 B1 and U.S. Pat. No. 5,656,207 by Batmanghelich et al. outline a structure for a purported, long-wavelength-emitting acridinium ester, in which an extended conjugation system is drawn by appending a substituted carboxybutadienyl group to the acridinium ester. However, in the Batmanghelich patents, neither the synthesis of this acridinium ester nor its emission properties was described to enable and substantiate the claim of light emission maxima of 500–700 nm, as already pointed out in the U.S. patent application Ser. No. 08/308,772, now U.S. Pat. No. 5,879,894.

Other non-acridinium ester-based, long emitting chemiluminescent compounds related to stable 1,2-dioxetanes have been described by Bronstein et. al. in U.S. Pat. No. 4,931,223. Said patent discloses chemiluminescent 1,2-dioxetanes comprised of enzyme-cleavable, functional groups and light emitting fluorophores with different emission wavelengths. Specific preferred embodiments include a acetoxybenzopyran-substituted stable dioxetane (A), a phosphoryloxy-benzopyran-substituted stable dioxetane (B), and a β-galactosyloxy-benzothiazolyl-benzopyran-substituted stable dioxetane (C). The dioxetane A emits light with a 450 nm wavelength maximum when its acetoxy group is cleaved by an esterase. The dioxetane B emits lights at a 480 nm wavelength maximum when its phosphoryloxy group is cleaved by a phosphatase, while the dioxetane C emits light at 515 nm wavelength maximum upon treatment with the enzyme β-galactosidase. The patent provides an example of a three-channel analysis for the simultaneous detection of HSV, CMV, and HPV in a nucleic acid probe simultaneous assay, using three, narrow band-pass optical filters to sort out the different color emissions from the aforementioned dioxetanes. The levels of HSV, CMV, and HPV present in the sample were correlated by the corresponding image brightness. Because the three light emission maxima are so close together, most of the spread from each emission spectrum had to be cut off by the narrow band pass filters to remove signal from the overlapping regions. This resulted in a very little usable amount of signal for each assay component and greatly limited the assay sensitivity and perhaps accuracy.

Edwards et al. [J. Biolumin. & Chemilumin., 5, 1 (1990)] have reported an another chemiluminescent dioxetane, 3-(2'-spiroadamantane)-4-methoxy-4-(7"-acetoxy)naphth-2'-yl-1, 2-dioxetane, which emits green light (maximum of 550 nm) with a bathochromic shift of 90 nm in comparison to its 6"-acetoxy substituted isomer. This is attributed to the different position of the enzymatically cleavable acetoxy substituent that gives rise to an oxide anion substituent responsible for triggering dioxetane decomposition. Similar application of the two isomeric dioxetane compounds for the simultaneous detection of several analytes was suggested in the paper.

In this invention, we describe the design and synthesis of novel acridinium compounds which emit light with wavelength maxima >590 nm upon reaction with hydrogen peroxide. These acridinium compounds contain some key structural features which are critical for observing long-wavelength emission. These results along with our earlier observations described in U.S. Pat. No. 5,395,752 provide sound and experimentally verified rules for the design and synthesis of long-wavelength-emitting acridinium compounds.

For the improved measurement of the NIR chemiluminescent signal we also disclose in the present invention a modified, semi-automatic luminescence analyzer in which the red-insensitive photomultiplier tube has been replaced with a state-of-the-art low-noise, cooled CCD detector utilized in photon counting mode. By comparing the quantitated signals obtained from the original and modified analyzers we demonstrated an improvement in the specific activity of a NIR acridinium compound by about 40-fold. The use of a cooled CCD camera system for imaging chemiluminescent signal in the short wavelength region generated from a 1,2-dioxetane compound, was described by Martin, et. al. in J. Biolumin. Chemilumin. 9 (3), 145, 1994. The applications that were said to have been adapted to this imaging method, included various nucleic acid and immuno blottings, ELISA methods and DNA sequencing systems.

SUMMARY OF THE INVENTION

This invention identifies two sets of necessary and sufficient criteria for observing long-wavelength emission from acridinium compounds:

Set A:
(a) The creation of an extended conjugation system by the attachment of appropriate functional groups on the acridinium nucleus (electronic requirement).
(b) Coplanarity of the attached functional group and the acridone moiety during light emission (geometry requirement).
(c) Said functional group must consist of at least one aromatic ring and one electron-donating atom or group with an extra pair of electrons which can readily delocalize into the extended π system to which the heteroatom is directly attached or built into, and establish stable extended resonance with the electron-withdrawing carbonyl moiety of the light emitting acridone. Such electron-donating atom or group that exists in the form of an anion has particularly strong effect to further the bathochromic shift of the emission wavelength.

Set B:
(a) A direct attachment at one or more of positions C-2, C-4, C-5, or C-7 of the acridinium nucleus, of electron-donating atoms or groups having extra pair(s) of electrons. The electron-donating entities can be the same or different if more than one electron-donating entity is used. Such electron-donating atom or group that exists in the form of an anion has particularly strong effect to further the bathochromic shift of the emission wavelength.

For molecules for which the above criteria are met such as LEAE, 3-HS-DMAE, and 2-hydroxy-DMAE long wavelength-emission exceeding 500 nm and reaching into NIR region is expected and observed.

Preferably, the utility of an NIR-AC of comparable quantum yield as the conventional acridinium compounds goes hand-in-hand with the employment of a luminenscence detector of good to excellent detection efficiency. To achieve efficient NIR signal detection and facilitate the performing of diagnostic assays, a further objective of the present invention is the advance of a concept and the realization of substituting a state-of-the-art charge-coupled device (CCD) detector for the red-insensitive photomultiplier tube (PMT) in a conventional fully or semi-automatic analyzer such as MLA-II of Chiron Diagnostics, Walpole, Mass.

BRIEF DESCRIPTION OF THE FIGURES

FIG. 4 is a schematic diagram of the Dual-Analyte Probe Assay described in Example 16.

DETAILED DESCRIPTION OF THE INVENTION

Figure 1A:
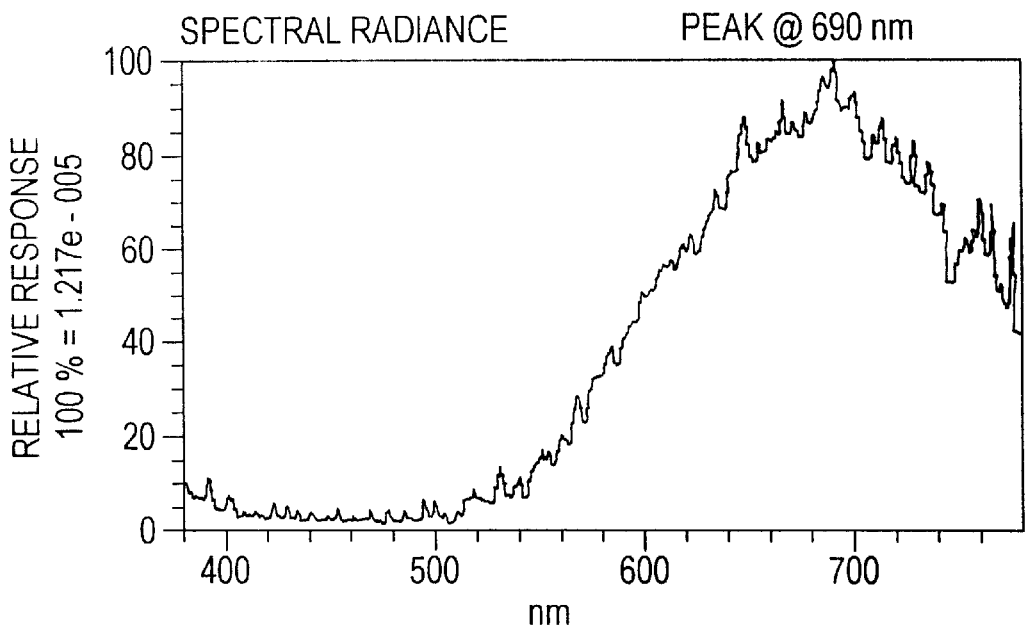
FIG. 1 depicts the normalized, light emission intensities (where the maximum response for each spectrum is shown as 100%) as a function of wavelength (in nm) for some of the various compounds which were evaluated. (Note, the quantity of the compound evaluated in each analysis ranged from about 10 to 100 ug. The emission intensity, being a function of amount of compound present, was normalized so that the maximum intensity at the peak in the wavelength range investigated was set at 100.) The scale for FIG. 1F is labeled slightly differently, but it still should be interpreted the same way.
Figure 1B:
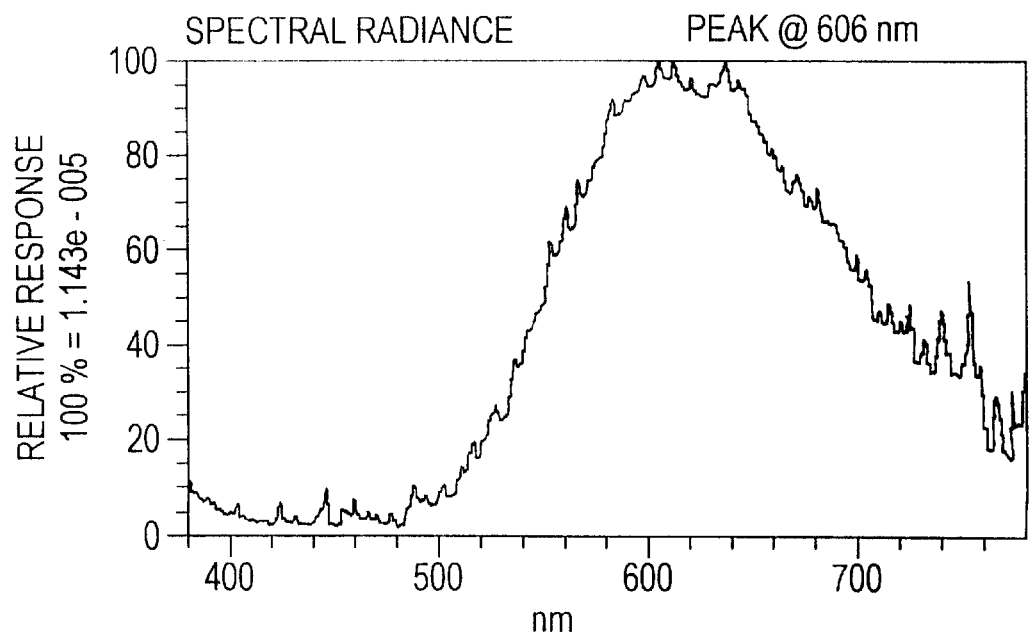
Figure 1C:
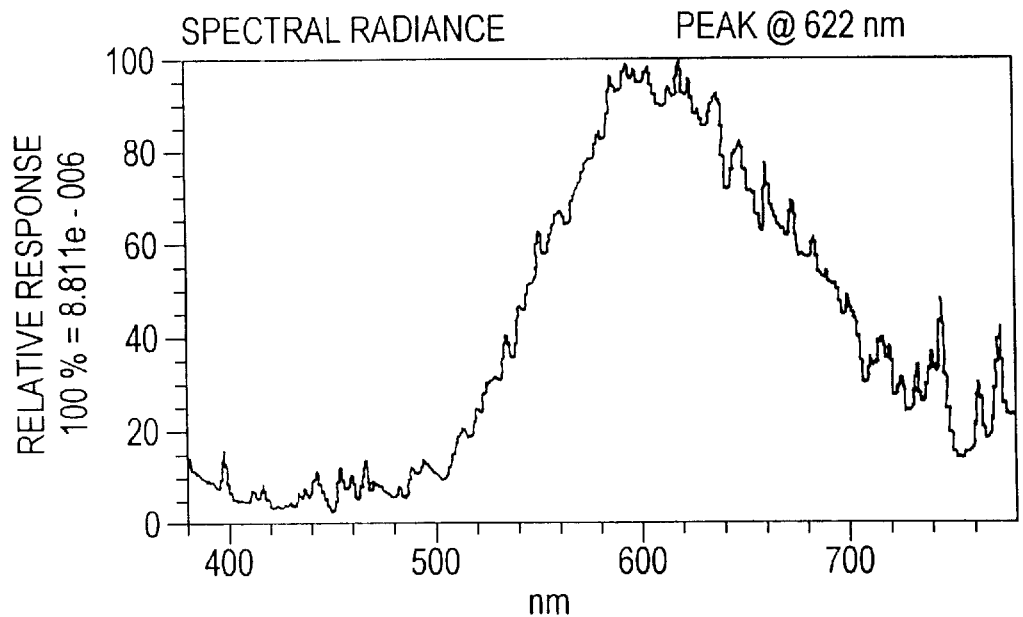
Figure 1D:
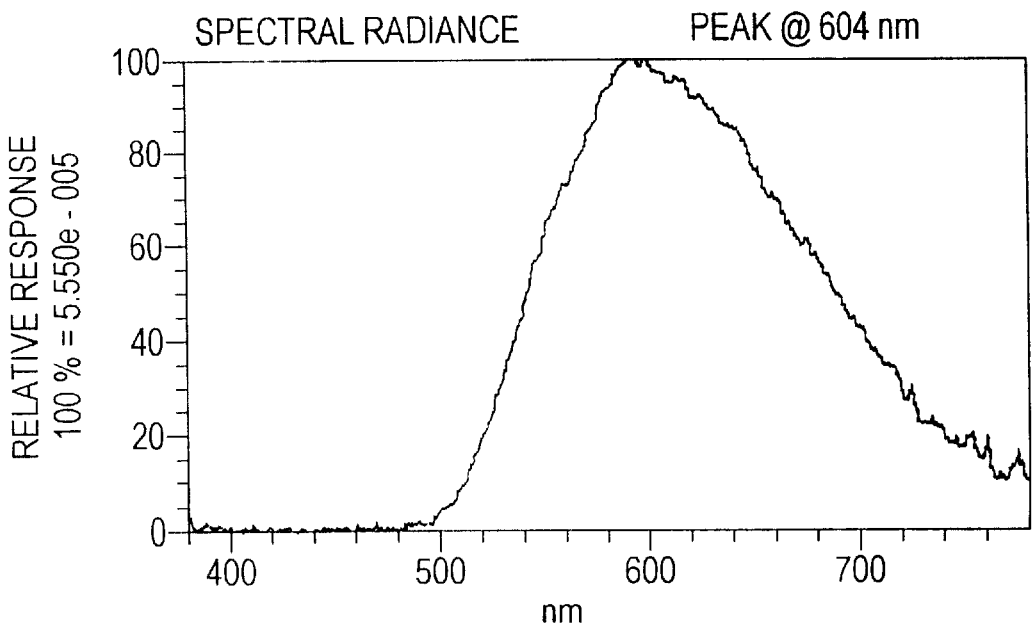
Figure 1E:
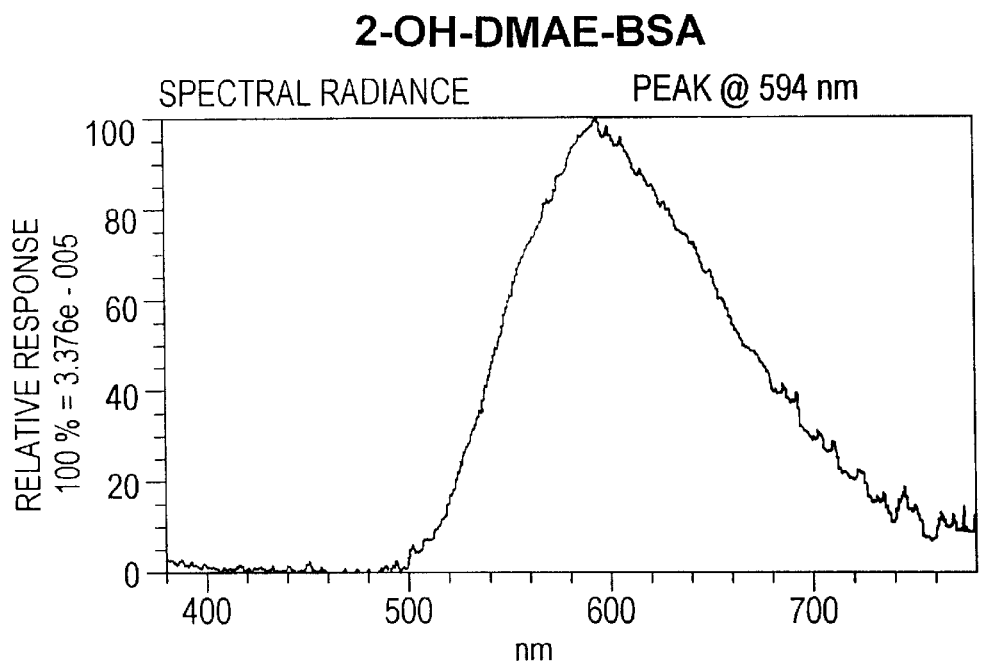
Figure 1F:
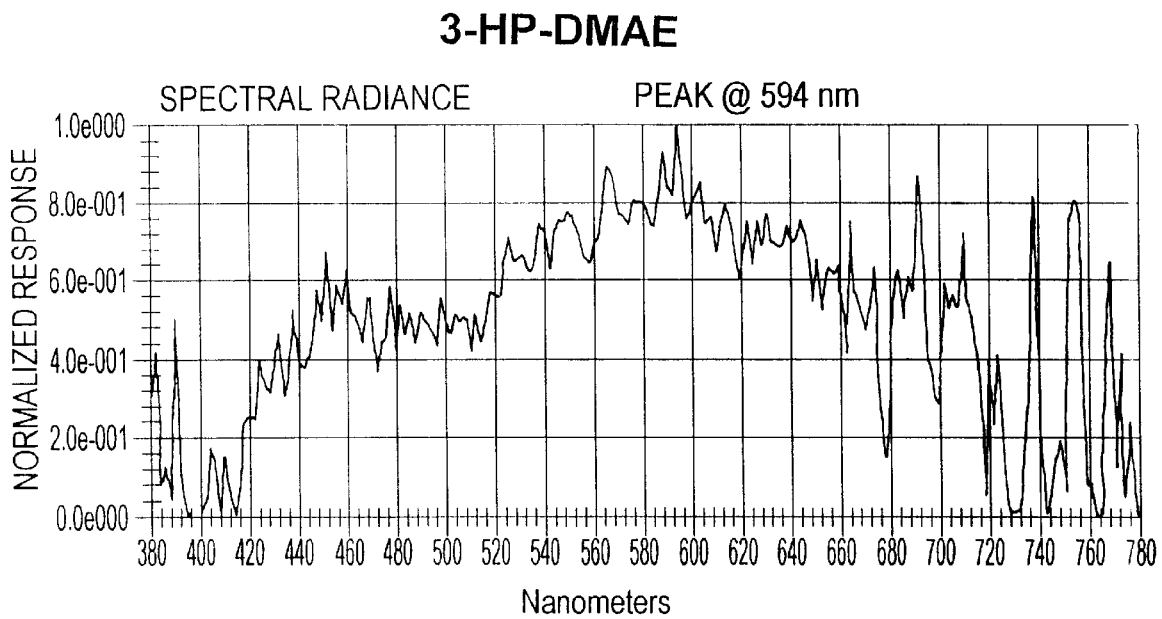
Figure 1G:
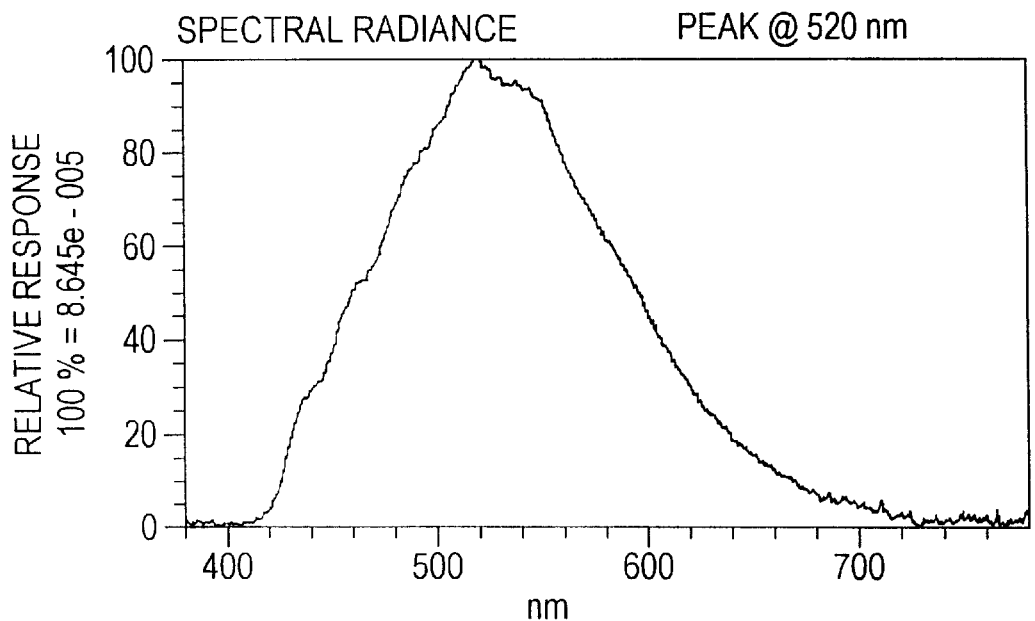
Figure 1H:
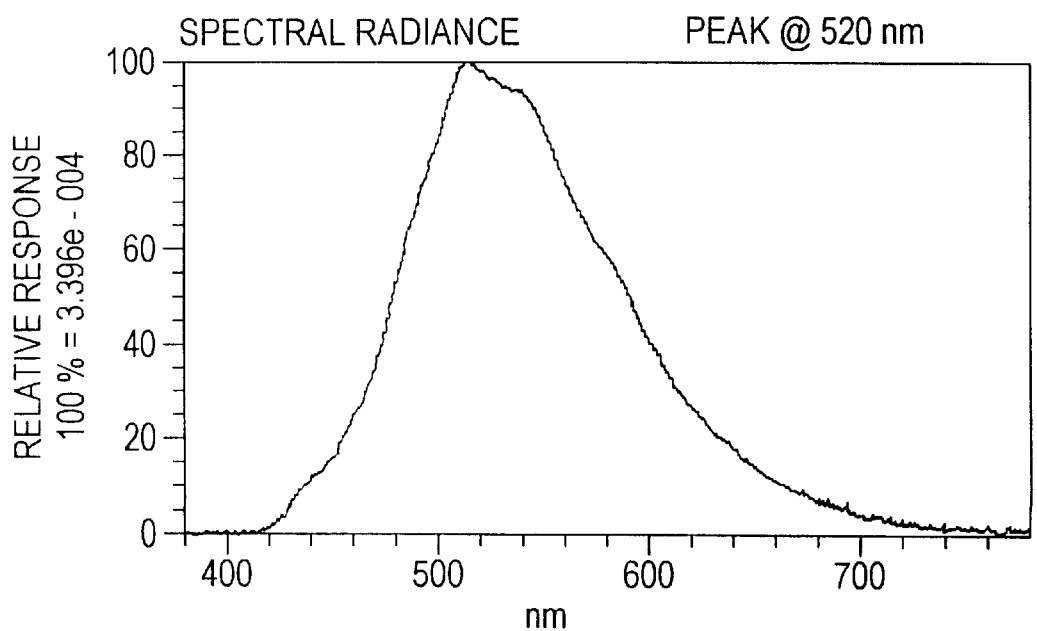
Figure 1I:
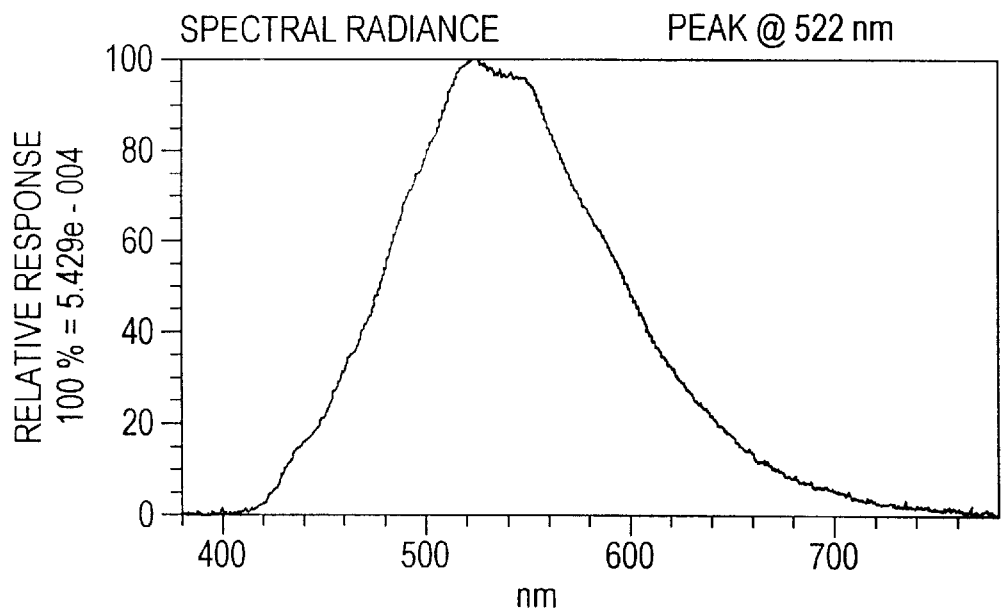
Figure 1J:
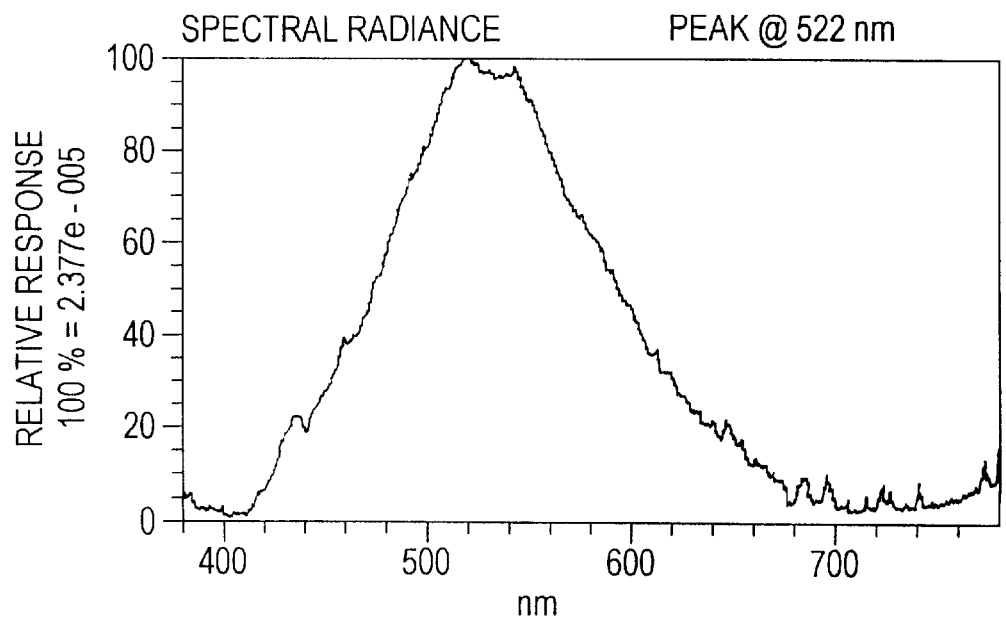
Figure 1K:
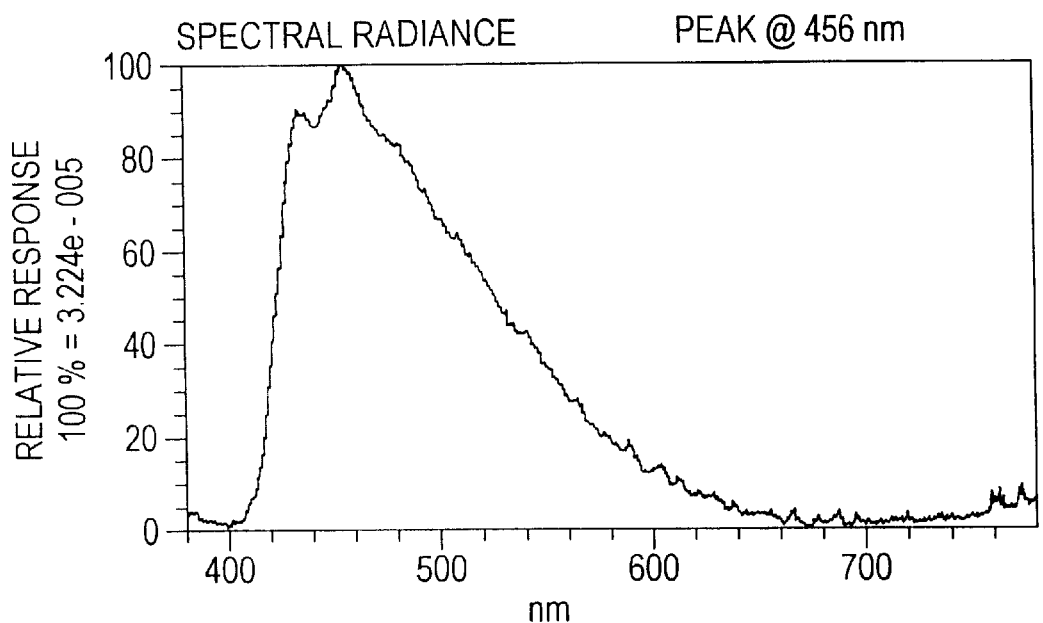
Figure 1L:
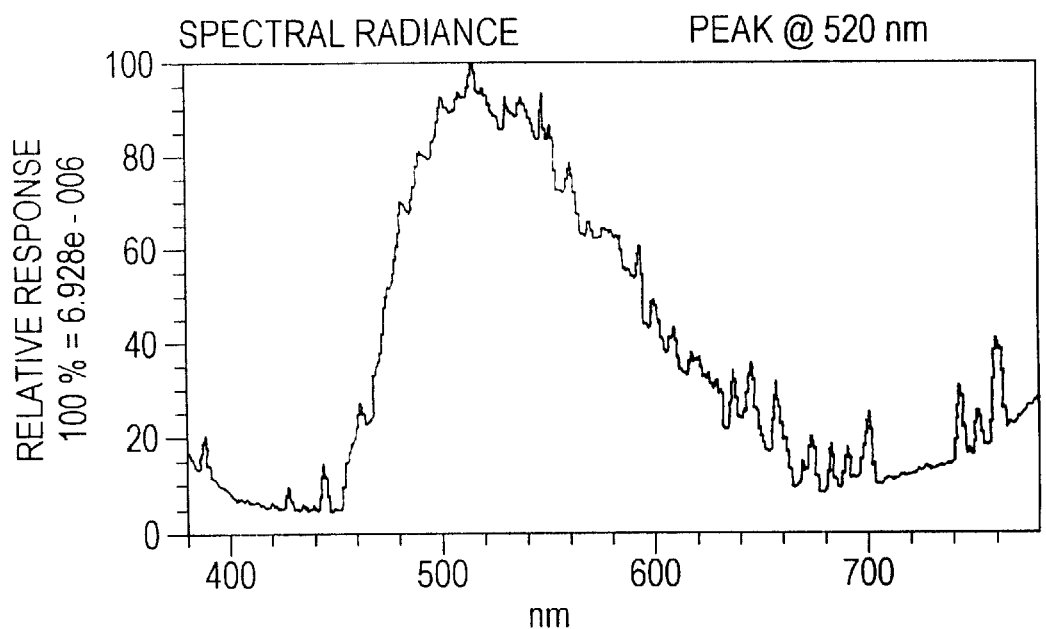
Figure 1M:
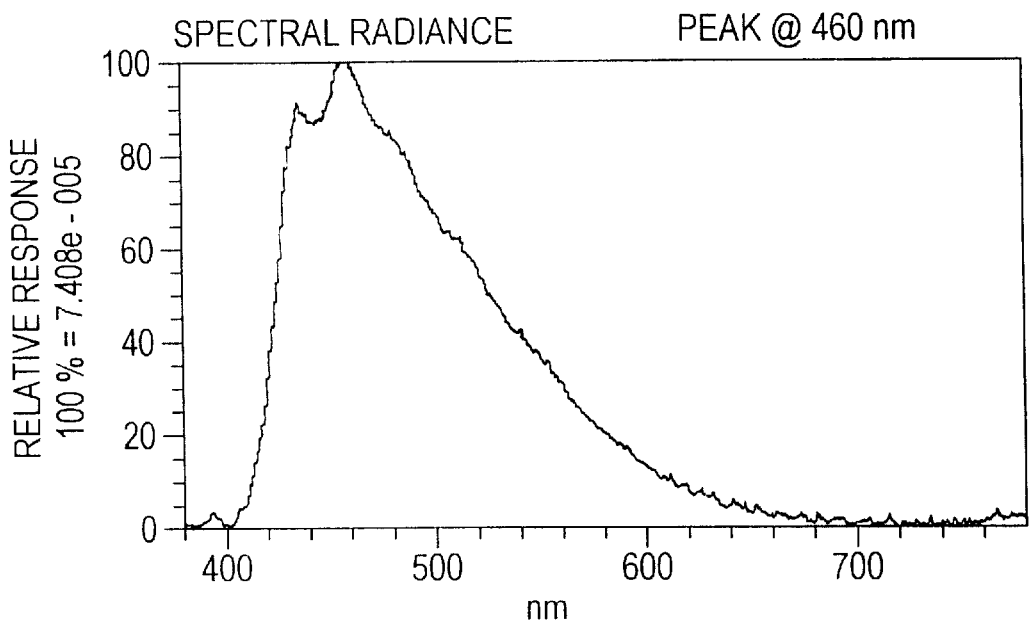
Figure 1N:
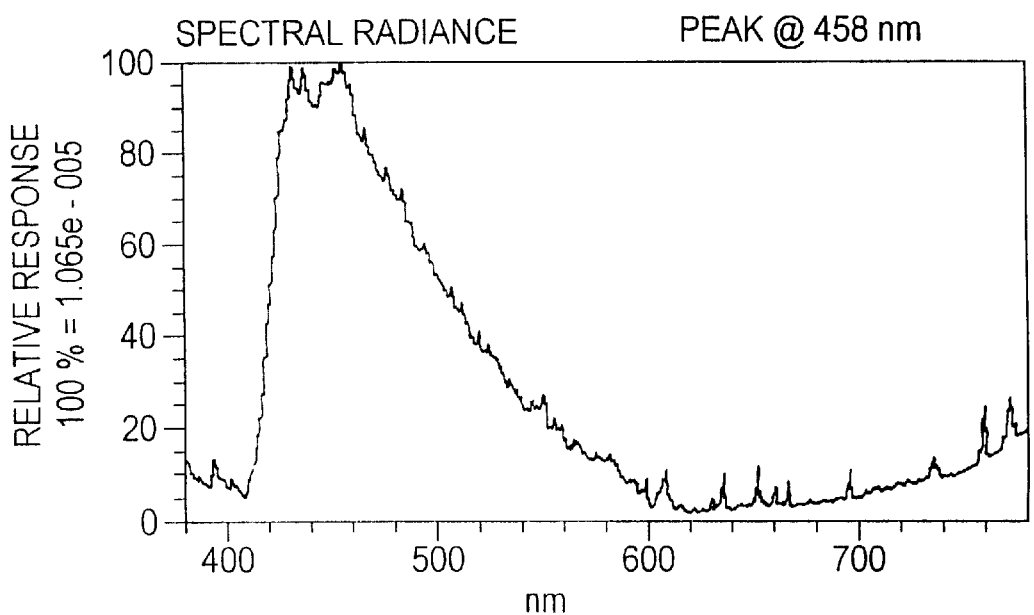
Figure 1O:
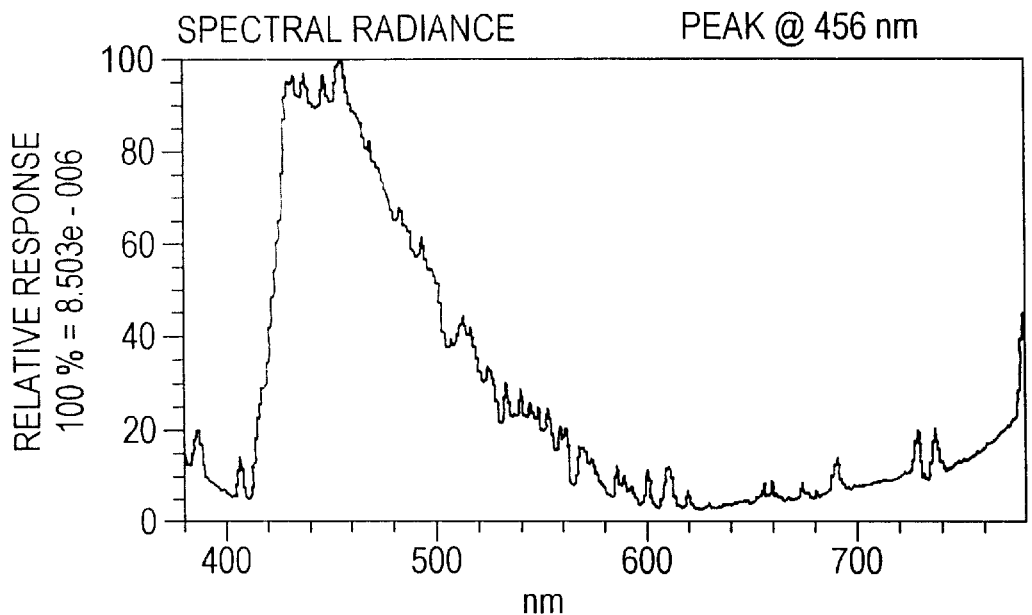
Figure 1P:
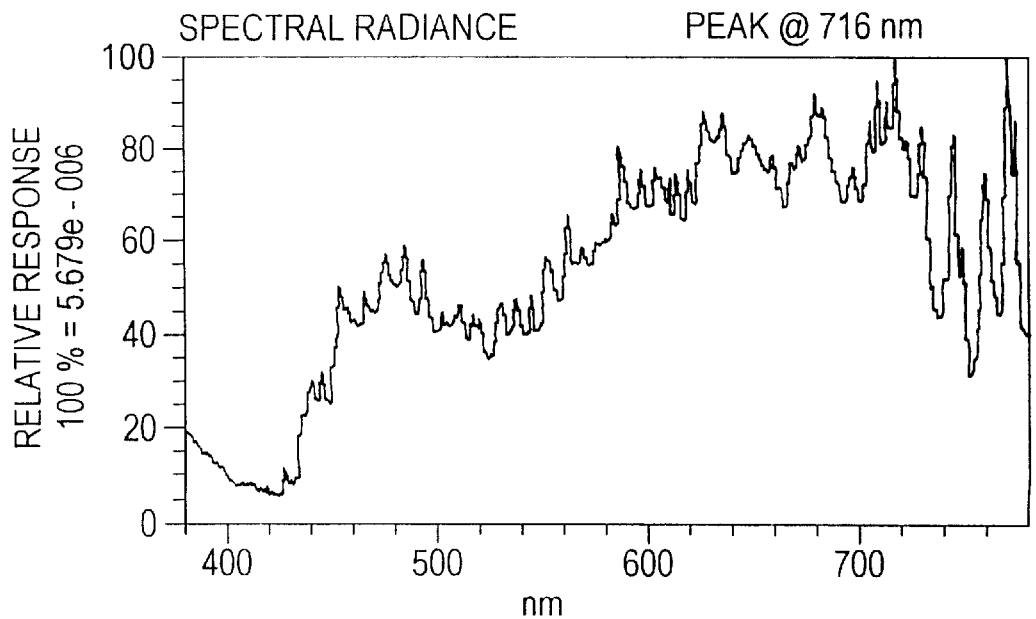
Figure 1Q:
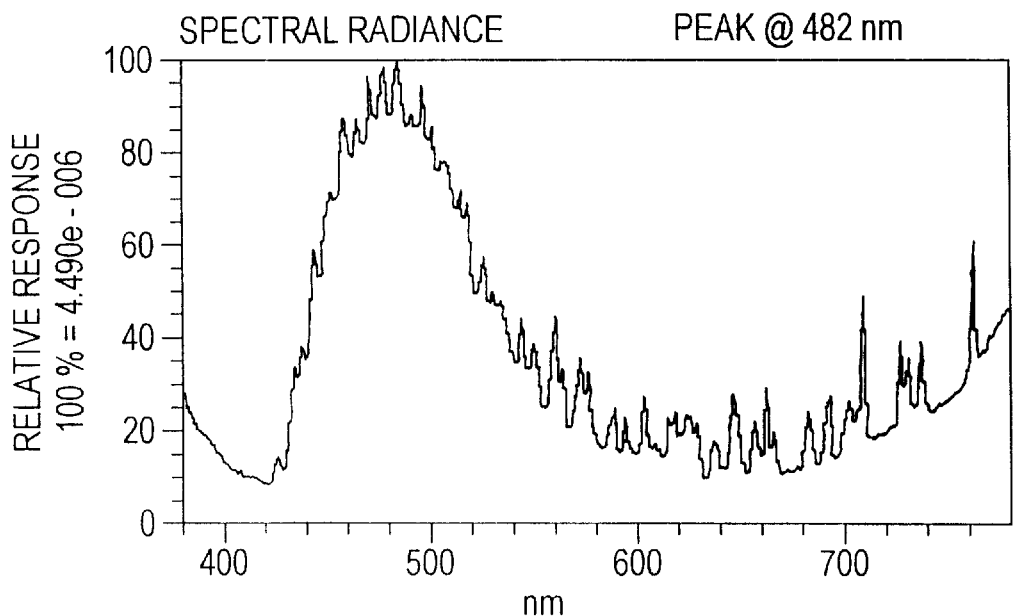
Figure 1R:
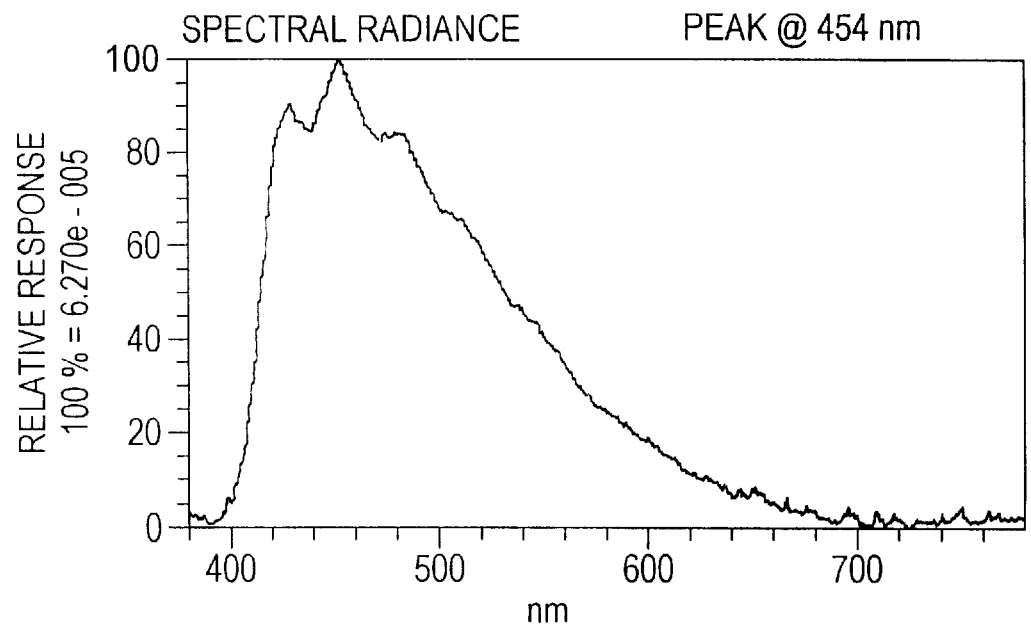
Figure 2:
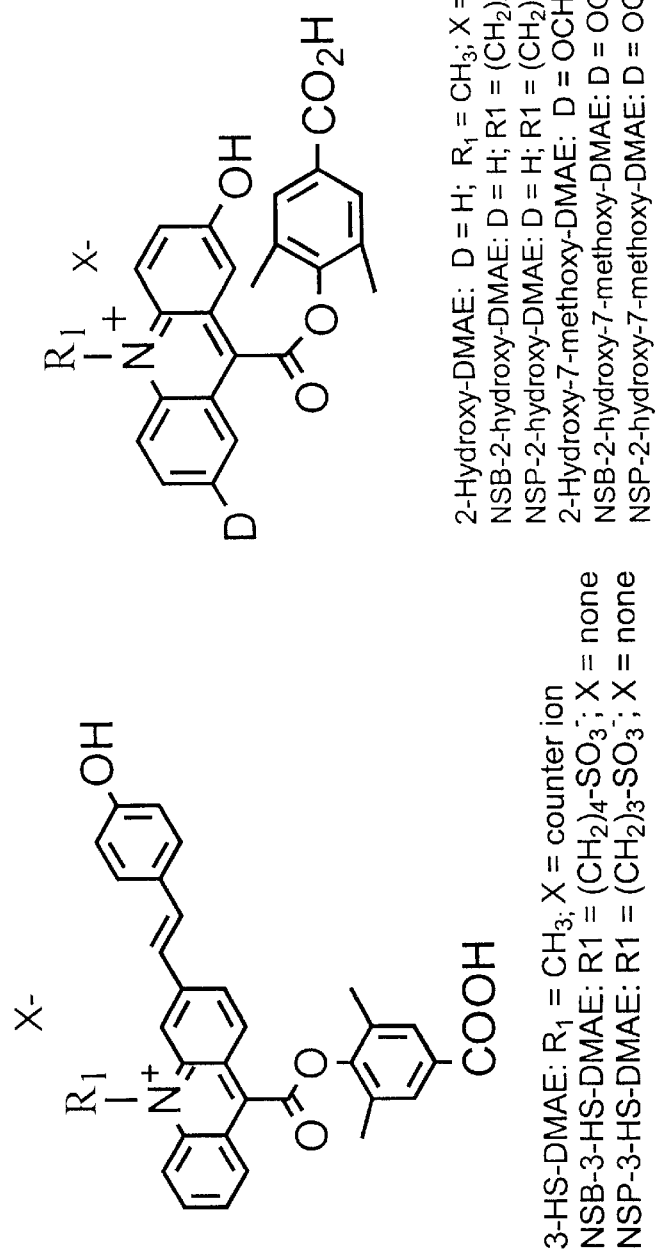
FIG. 2 shows the structure of selective compounds referred to in this patent.

The chemiluminescent reaction of a PAAE is triggered by hydrogen peroxide in strong alkaline solution (see figure below). The light emitting species is the acridone which is formed in an electronic excited state during the chemical (peroxide-mediated) decomposition of the acridinium ester via a putative, highly strained and unstable dioxetanone intermediate. (It should be noted that any chemical which releases bivalent peroxide can be used, for example, sodium peroxide or any bivalent peroxide salt.)

Light emission occurs when this excited acridone reverts to its ground state. The energy (wavelength) of the emitted light depends upon the difference of energy between the first excited state and the ground state, which in turn is determined by the specific structure of the acridones with various functional group T.

A second, equally critical requirement, which is related to conformation (geometry), is that the extended conjugated system must remain, at all times, coplanar with the acridone π-system so that the over-all, planar structure of the light emitting species is indeed the only most energetically-favored conformation of the molecule. If such a geometry is energetically unfavorable, or if the molecule can assume other, nonplanar, conformations as well, then long-wavelength emission is either not possible, or the resulting emission spectrum will cover such a broad range that the utility of the compound as a label in a simultaneous, multiple analyte assay will be questionable.

The most convenient as well as critical sites for modification of acridinium compounds are C-2 (C-7) and C-3 (C-6). In LEAE, the appended functional group responsible for long-wavelength emission is an aromatic ring fused in a linear fashion to both C-2 and C-3. By doing so, complete planarity of the extended π-system is assured and the molecule is permanently locked into the lowest-energy, planar conformation. Consequently, LEAE, in its chemiluminescent reaction with hydrogen peroxide, emits light at 520 nm, an extension of 92 nm from the emission maximum of conventional acridinium compounds. In contrast, the carboxybutadienyl substituted AE fails to achieve an emission maximum of 510 nm as claimed by Batmanghelich et. al. This is apparently because of the inability of the molecule to fulfill the coplanar rule for effective electron delocalization throughout the entire π system. As a result, 3-carboxybutadienyl AE only shows an emission maximum of 464 nm, an entension of merely 36 nm from the emission maximum of the original acridinium ester as demonstrated in the U.S. Pat. No. 5,879,894. Extensive emission spectral overlap remains between the 3-carboxybutadienyl AE and the original AE.

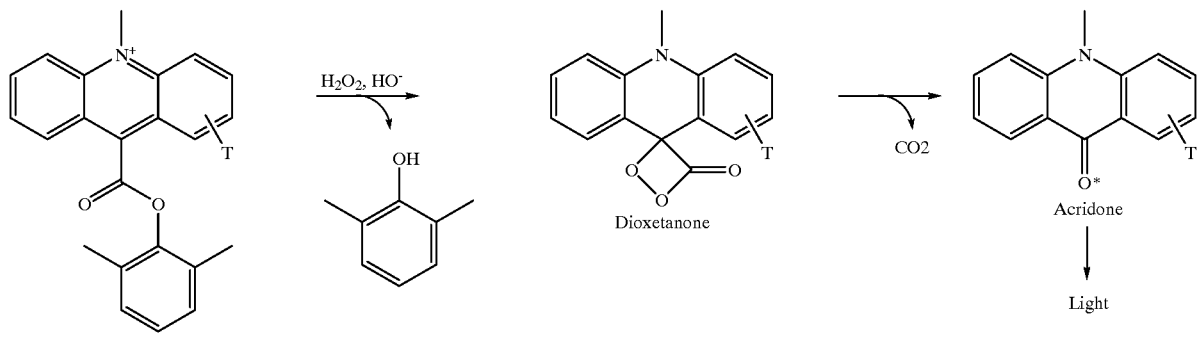

It is evident that in order to observe long-wavelength emissions from acridinium esters and derivatives (e.g. acridinium sulfonylamides), the energy gap between the excited and ground states of the corresponding acridone must be reduced. Normally, an extended conjugated system decreases the energy gap for the molecule in question. For acridinium compounds, therefore, this necessitates attachment of a suitable functionality to the acridinium nucleus at a critical ring position so that an extended conjugated system is created. This is predicted to result in a shift in the emission properties of the corresponding acridone to longer wavelengths.

In the case of aromatic, ring-fused, acridinium ester systems, we also want to stress the importance of linearity along a horizontal axis of the whole π-system for effective extension of the emission maxima. Aromatic rings fused in an angular manner to the acridinium nucleus at C-1 (C-8) and C-2 (C-7) positions, for example, extend the emission maxima only minimally from 428 to 440 nm (see U.S. Pat. No. 5, 395,752), making it very difficult to discern the difference in the emission spectra between the angular, aromatic ring-fused PAAE and the parent PAAE, when their chemiluminescence occur together in the same tube.

Numbering System for Acridinium Nucleus

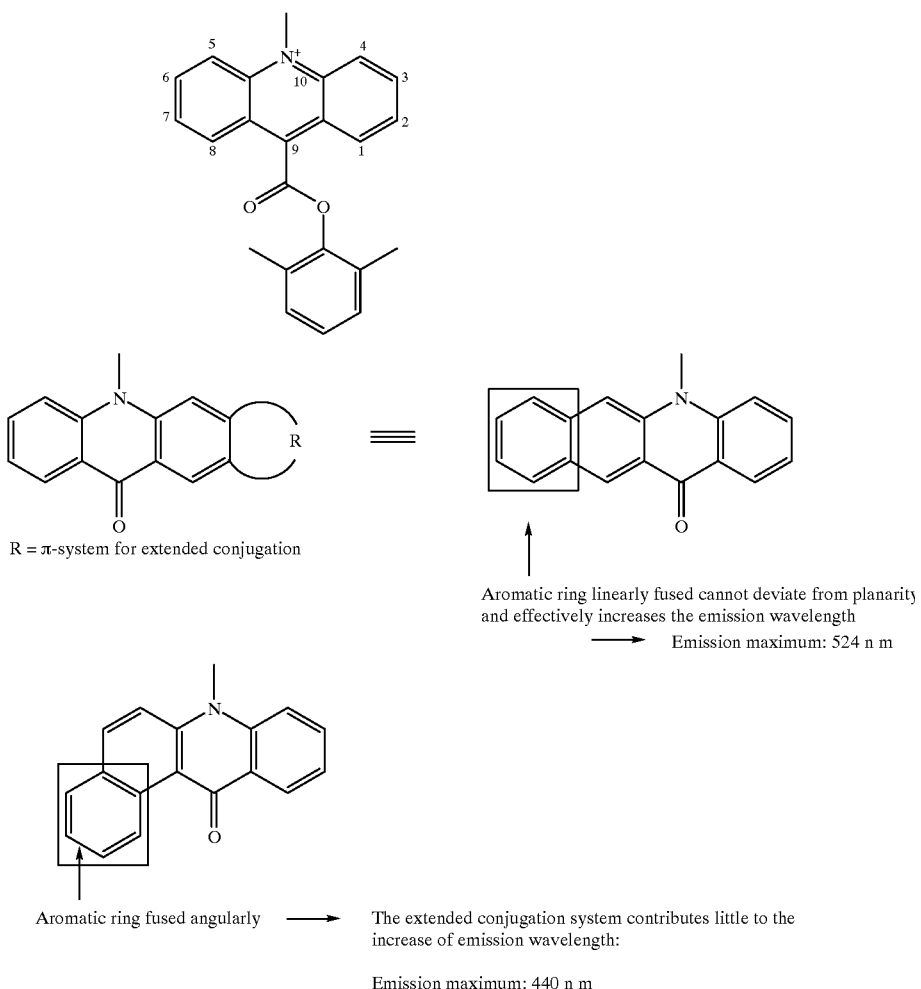

An alternative mode of creating an extended conjugated system according to the present invention involves the single point attachment of the requisite functional group (T) to one of the peri-positions (C1–C4) of the acridinium nucleus. Said functional group must carry at least one electron-donating atom or group with an extra pair of electrons which can readily delocalize into the extended, conjugation system of the AE nucleus to which the electron-donating atom or group is directly attached or built into. Electron-donating atom involved in such structural arrangements include the commonly encountered oxygen, sulfur, and nitrogen which appear, for instance, in styrenyloxide, thiophenoxide, naphthoxide, indole, benzimidazole, benzotriazole, benzothiazole, and other numerous other aromatic, heterocyclic systems. Some resonance structures are shown below for illustration of the involvement of the electron pair in the extended, conjugation systems.

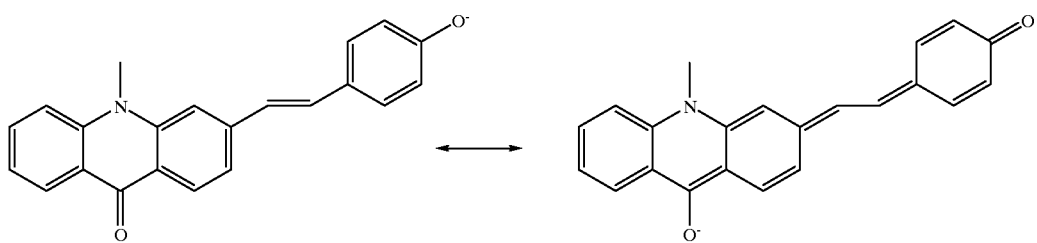

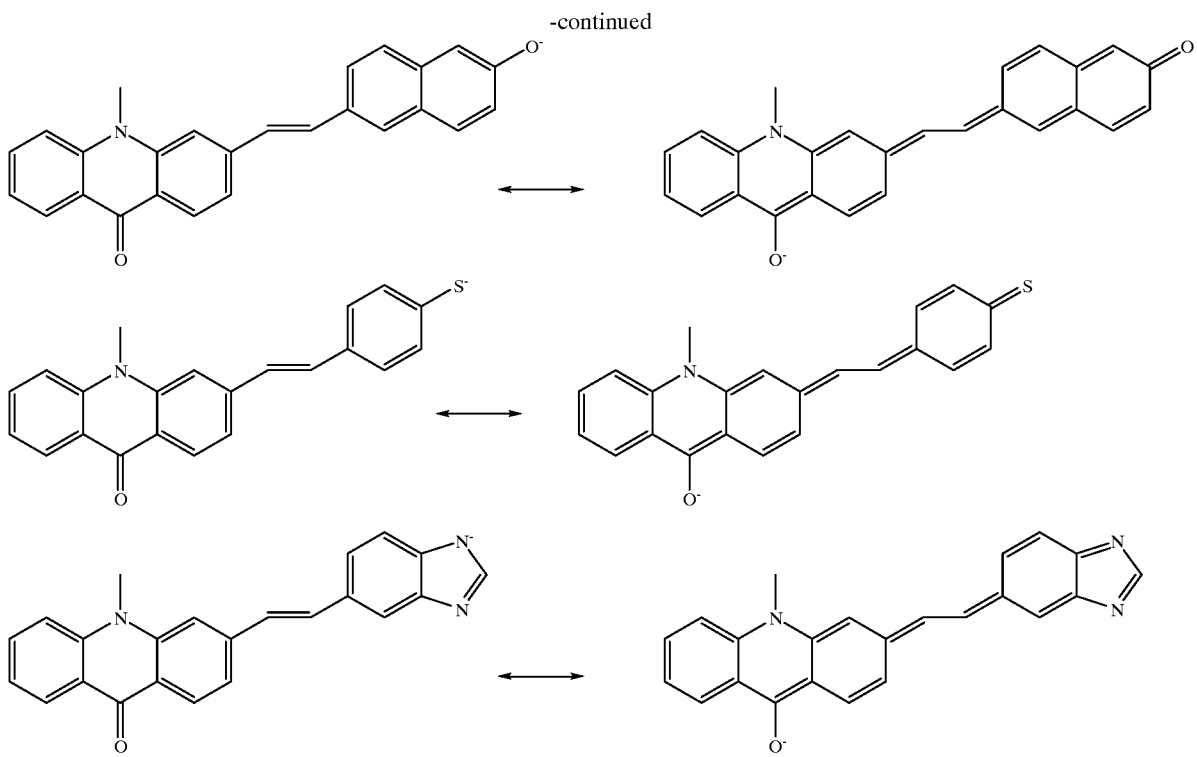

In the mode where a single point attachment of T to either C-2 or C-3 is utililized, unlike in LEAE, molecular rotation can now occur around the bond connecting the acridone. Consequently, the wavelength of the emitted light from the corresponding acridone will depend upon whether the acridone and R are coplanar or not.

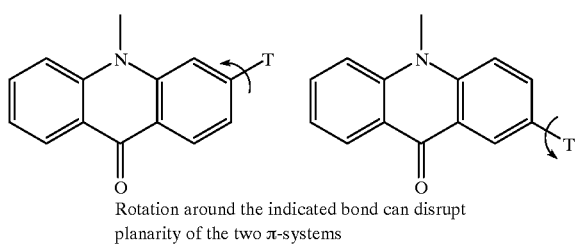

Rotation around the indicated bond can disrupt planarity of the two π-systems

To determine whether attachment of such a functional group to the peri-positions (C1–C4) of the acridinium nucleus is a viable approach for creating long-wavelength emitting acridinium esters, we synthesized and evaluated the emission properties of acridinium esters containing a 4-hydroxystyrenyl (4-HS-) and a 4-methoxystyrenyl (4-MS-) group at both C-2 and C-3 (Schemes 1 and 2). C-3 position was chosen as a representative of C-1 and C-3 positions, both of which would allow the eletron-donating atom or group of T to participate in long-range resonance with the carbonyl moiety of acridone. Similarly, C-2 position is a representative of C-2 and C-4 positions, both of which would not allow the same.

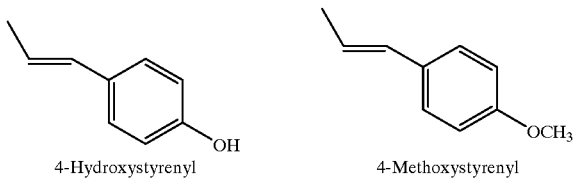

4-Hydroxystyrenyl      4-Methoxystyrenyl

Both the functional groups contain the extended conjugation system of the styrenyl moiety with an oxygen atom attached to the para position of the aromatic ring. The two functional groups, however differ in the ease with which they are capable of delocalizing a pair of electrons from the oxygen to the styrenyl π system. In alkaline media, the 4-HS-group, after deprotonation forms the phenoxide anion which is strongly electron donating and can readily delocalize its extra pair of electrons into the π system that it is attached to. For the 4-MS-group, since the ether oxygen cannot be deprotonated, such a mechanism for electron donation is not possible. While it is possible to write a resonance structure whereby even the ether oxygen in the 4-MS-group donates an n-electron pair to the attached π-system, this entails creating a positive charge on the ether oxygen. This resonance contribution is thus expected to be of high energy and is therefore likely to make only a minimal contribution to the electronic properties of the overall π system. The results of the studies that follow are anticipated to bear direct relevance to the emission properties of the reported 3-carboxybutadienyl acridinium ester and to provide an unambiguous protocol in terms of what the necessary structural features indeed are which are responsible for extending the emission maximum of acridinium ester into the 500–700 nm region.

The syntheses of the C-2 substituted analogs are shown in Scheme 2. Isatin was N-alkylated with 2-(4-bromophenyl)-

1,3-dioxalane as disclosed in U.S. patent application Ser. No. 08/308,772. The N-alkylated isatin was rearranged to the corresponding acridine derivative by refluxing in 10% KOH [Zomer at al. in "Synthesis, Chemiluminescence, and Stability of Acridinium Ester Labeled Compounds", *Pract. Spectrosc.* 1991, 12 (Lumin. Tech. Chem. Biochem. Anal.), 505–21]. Hydrolysis of the dioxalane afforded the 2-carboxaldehyde which was condensed with the ylid from either 4-benzyloxybenzylphosphonium chloride or 4-ethoxybenzyltriphenylphosphonium chloride. In both cases, the Wittig reaction afforded a mixture of E and Z olefins. The E olefin was observed to be more stable in each case and could be isolated pure after chromatography. However, pure Z isomer could not be isolated because in each case, the compound underwent partial to complete isomerization during purification. Consequently, only the E-isomer in each case was elaborated on further. The acridine nitrogen was alkylated with either methyl trifluoromethane sulfonate (4-hydroxyphenyl analog) or 1,4-butane sultone (4-methoxyphenyl analog). The benzyl ester was removed to liberate the free acid which was then converted to the N-hydroxysuccinimide ester using dicyclohexylcarbodiimide and N-hydroxysuccinimide.

The syntheses of the 3-substituted analogs were accomplished in a similar fashion (Scheme 1) except that 2-(3-bromophenyl)-1,3-dioxalane was used to alkylate isatin. This ensures that the carboxaldehyde is introduced at C-3 in the acridine nucleus.

Protein conjugates of the acridinium esters were also prepared as described in examples 8–13.

Chemiluminescent emission spectra of the synthesized acridinium esters and protein conjugates were recorded using Spectrascan camera. The results are shown in FIG. 1 which depict the normalized, light emission intensities as a function of wavelength for the various compounds which were evaluated.

The results in FIG. 1 show dramatic differences in the wavelength of the emitted light for the various compounds. 3-HS-DMAE, which contains a 3-(4-hydroxystyrenyl) moiety, shows long-wavelength emission with a maximum centered ~690 nm. Conjugation of this molecule to BSA shifts its emission maximum to ~610 nm. This hypsochromic shift of the emission maximum can be attributed to a solvent effect, since the emission spectrum of the free compound was measured in a medium containing about 42% organic solvent to ensure complete solubility, while the protein conjugate was measured in a completely aqueous medium because of the incompatibility of protein with organic solvent. Similarly, NSB-3-MS-DMAE showed a hypsochromic shift of ~66 nm when its spectrum was recorded in water as opposed to either DMF or acetonitrile. Changes in the emission maximum of 30 acridinium compounds that give rise to the same, blue light-emitting, N-methylacridone, as a function of the solvent mixture used, have also been recorded. McCapra et al. [Tetrahedron Letters No. 43, 3167, (1964) and Photochem. & Photobiology, 4, 1111, (1965)] reported an emission maximum of 442 nm for a number of acridinium salts in 80% aqueous alcohol, while we previously observed an emission maximum of 426–430 nm for DMAE in 42% DMF. Another example of a hypsochromic shift influenced by the solvent was observed between free N-sulfopropyl-DMAE, which emits at 424 nm in 42% DMF vs. N-sulfopropyl-DMAE-BSA conjugate which shows maximum emission at 420 nm in a completely aqueous medium. In general, acridinium ester labels, when flashed in an organic solvent rich medium, will give longer emission maxima than in water rich or completely aqueous environments. The difference in the observed maximum varies from about 4–12 nm in the case of shorter emission AEs to about 80 nm as seen in the present case of NIR-AE, which appears to be more susceptible to solvent effects. A similar conjugate of BSA, with the hydrophilic version of the NIR-AE termed NSB-3-HS-DMAE, has a N-sulfobutyl substituent instead of methyl group at the ring nitrogen of the acridinium nucleus. This conjugate also shows long wavelength emission at 620 nm. Note that for practical utility in binding assays, the only relevant emission maxima are those obtained in a completely aqueous environment.

In sharp contrast to the above compounds and conjugates, the acridinium ester termed NSB-3-MS-DMAE, which contains a 3-(4-methoxystyrenyl) moiety, shows light emission at much shorter wavelength (455–460 nm) either as the free label or when conjugated to protein.

The acridinium ester, NSB-2-MS-DMAE, like the 3-analog, also shows relatively short-wavelength emission at 454 nm. The acridinium ester 2-HS-DMAE, unlike the 3-isomer, was found to emit light over a wide range 450–700 nm. When this compound was conjugated to BSA, its light emission was at relatively short wavelength (482 nm).

In addition to the styrenyl substituted acridinium compounds, we prepared an acridinium ester where a 4-hydroxyphenyl moiety is directly attached to C-3 of the acridinium nucleus (Scheme 3). This compound termed 3-hydroxyphenyl-DMAE (3-HP-DMAE) was found to have an emission maximum at 594 nm. However, the emission spectrum of 3-HP-DMAE was observed to cover a broad range of about 420 nm to 780 nm with multiple maxima.

The emission spectra in FIG. 1 clearly demonstrate that creation of an extended conjugation system by linking the appropriate functionality at C-2 or C-3 of acridinium ester, in itself, is a necessary but not a sufficient condition to get long-wavelength emission. The relatively short-wavelength observed in the emission spectra of the 3-carboxybutadienyl-AE, and MS-DMAE derivatives strongly suggests that the two π-systems (acridone and the 4-methyoxystyrenyl) are not coplanar. Similarly, for the 2-HS-DMAE, while the free label appears to show light emission from a range of low energy conformations, its emission spectrum when attached to protein suggests that there is considerable deviation from coplanarity of the two π-systems.

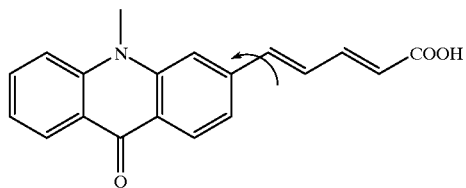

Emission maximum: 464 nm in mixed solvents

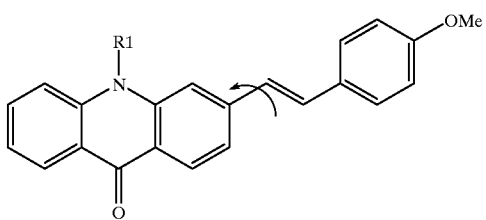

Emission maximum:
520–522 nm in mixed solvents
456 nm in aqueous media

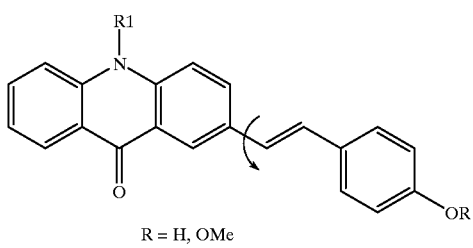

R = H, OMe

Emission maximum:
Very broad in mixed solvents
454-482 nm in aqueous media

Only the 3-HS-DMAE derivatives show emission at long wavelength. While rotation around the bond connecting the two π-systems is also possible for this compound, in strong alkaline pH, resonance delocalization of the phenoxide negative charge onto the electron withdrawing carbonyl moiety of the acridone provides a strong incentive for this compound to remain coplanar during light emission. Consequently, the extended conjugated system is maintained and long wavelength emission is observed. A similar mechanism also operates for 3-HP-DMAE but here the steric requirements for coplanarity of the hydroxyphenyl substituent relative to the acridinium nucleus are not completely met and hence emission from this compound occurs over a broad range of wavelength.

Having observed the dramatic effect of an extra pair of electrons in lowering the energy of extended π-systems for the C-3 functionalized acridinium compounds, we then examined the effect of the direct attachment of a hydroxyl group as a representative of electron-donating atoms or groups, to the acridinium nucleus on its emission properties. Among the two sets of alternate peri-positions of the acridinium nucleus, we chose to study the attachment at C-2 and C-3 again as the representative of group A (C-2, C-4, C-5, and C-7) and group B (C-1, C-3, C-6, and C-8) positions, respectively. The members within each group are expected to have similar emission characteristics because they are isomers with the hydroxyl group attached at the alternate position on the acridinium nucleus. Unexpectedly, we found that 2-hydroxy-DMAE, but not 3-hydroxy-DMAE is also capable of long wavelength emission (emission maximum of 604 nm), despite the absence of an extended conjugation system between the hydroxy substituent and the acridinium nucleus.

In strong alkaline solution, this hydroxyl group is expected to be deprotonated. The negative charge associated with this oxygen thus decreases the energy gap between the ground and electronic excited state of the corresponding acridone and leads to long wavelength, light emission. We thus disclose another novel method for the creation of acridinium esters that emit light in the NIR region. The structure of 2-hydroxy-DMAE has been included in the substance claim of U.S. Pat. Nos. 4,918,192 and 5,110,932 as one of the hydrolytically stable chemiluminescent PAAE. Synthesis of 2-hydroxy-DMAE is given in the example section of this application.

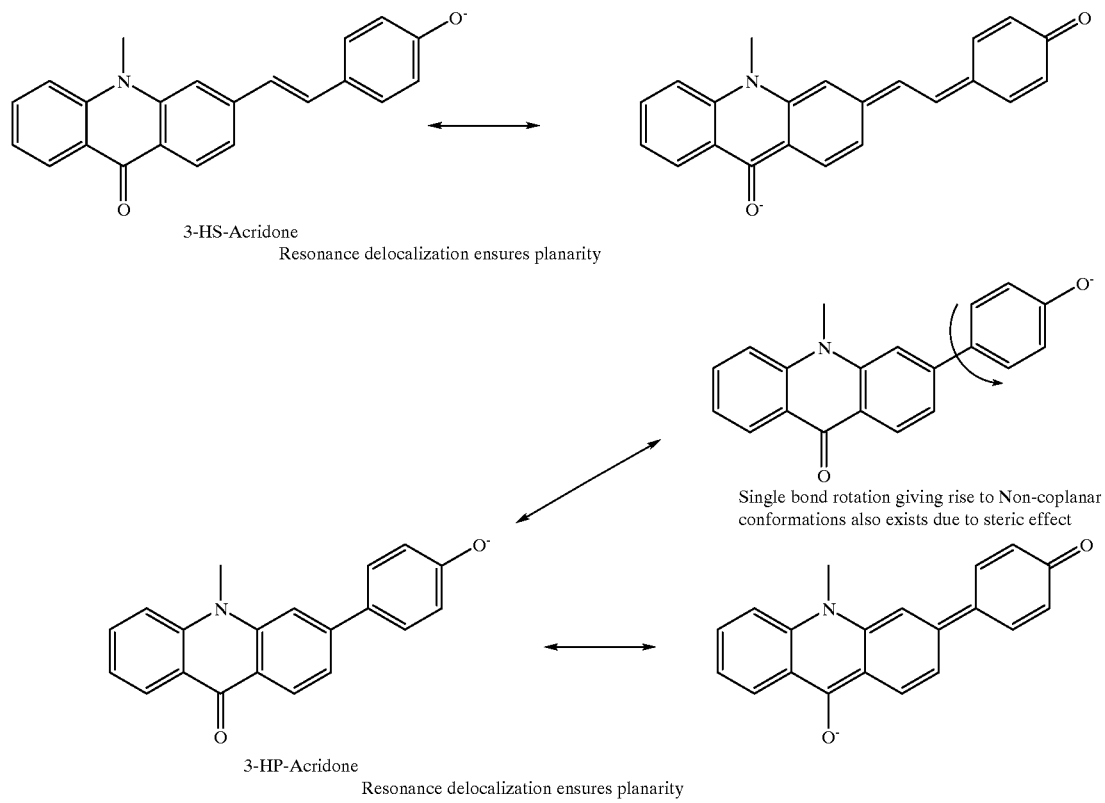

3-HS-Acridone
Resonance delocalization ensures planarity

Single bond rotation giving rise to Non-coplanar conformations also exists due to steric effect 3-HP-Acridone
Resonance delocalization ensures planarity

Preferred Embodiments

A. Structures of Chemiluminescent Near Infrared Acridinium Compounds (NIR-AC)

The general structure of the set A chemiluminescent NIR acridinium compounds of the present invention can be schematically represented as follows:

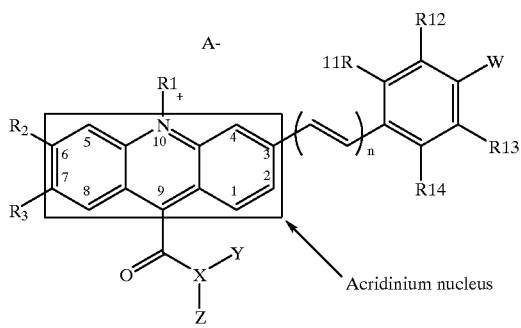

wherein $R_1$ is an alkyl, alkenyl, alkynyl or aralkyl containing optionally up to 20 heteroatoms; preferably $R_1$ is methyl or sulfoalkyl group.

$R_2$ and $R_3$ are identical or different, selected from hydrogen, R, substituted or unsubstituted aryl (ArR or Ar), halide, amino, hydroxyl, nitro, sulfonate, —CN, —COOH, —SCN, —OR, —SR, —SSR, —C(O)R, —C(O)OR, —C(O)NHR, or —NHC(O)R;

Throughout this application, R is selected from the group consisting of alkyl, alkenyl, alkynyl, aryl, and aralkyl containing optionally up to 20 heteroatoms;

Alternatively, $R_2$ and $R_3$ can be linked, or they can be bridged, as exemplified by the following structures, so as to form an additional aromatic or non-aromatic ring fused to the attached acridinium nucleus. (See, for example, the first structure in the second line. If this sp$_2$ carbon (═C—) is linked to $R_2$ and $R_3$, a 5-member non-aromatic ring results.) It should be noted that the ring can be either heterocyclic or non-heterocyclic, and, therefore, that some of these resulting structures include endocyclic heteroatoms (i.e., heteroatoms which are part of the ring structure itself).

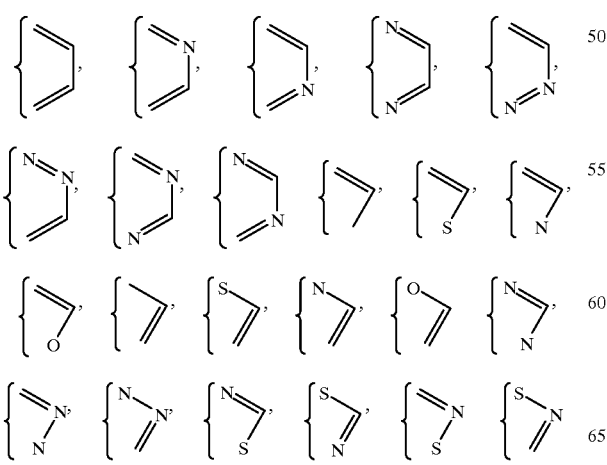

The $C_2$, $C_4$, $C_5$ peri-positions of the acridnium nucleus are optionally substituted.

n=1–4, preferably n=1;

W=an electron-donating group, preferably an ionizable group that can donate an electron pair such as OH, SH, NR'R", —CH(EWG)$_m$ where m=1 or 2 and EWG is an electron withdrawing group including but not limited to —NO$_2$, —NO, —CN, —CHO, —C(O)R, $^+$NR'R"R''', —COOR, —COOH, —S(O)R, —SO$_2$R, —SO$_2$OR, —SO$_2$NHR, —SO$_2$NR'R", —SO$_2$OH or F; R', R" and R''' are hydrogen or low alkyl and can all be the same or different;

Preferably, W=OH, SH, —NR'R";

$R_{11}$, $R_{12}$, $R_{13}$ and $R_{14}$ can be the same as $R_2$ or $R_3$; alternatively, either $R_{11}$ and $R_{12}$, or $R_{13}$ and $R_{14}$ can be linked as in $R_2$ and $R_3$ with the examples already shown above to form additional aromatic and/or heterocyclic ring fused to the attached phenyl ring.

A$^-$ is a counterion which is introduced to pair with the quaternary nitrogen of the acridinium nucleus either as a result of quaternarizing the acridine ring nitrogen by the use of alkylating agents during the synthesis, modification of the $R_1$, or subsequent exchanging mechanism that occurs during the work-up of reaction mixtures and purification of desired compounds in a solution or fluid containing excess amount of other anions. Examples of the counter ions include CH$_3$SO$_4$$^-$, FSO$_3$$^-$, CF$_3$SO$_4$$^-$, C$_4$F$_9$SO$_4$$^-$, CH$_3$C$_6$H$_4$SO$_3$$^-$, halide, CF$_3$COO$^-$, CH$_3$COO$^-$, and NO$_3$$^-$, X is nitrogen, oxygen or sulfur;

When X is oxygen or sulfur, Z is omitted and Y is a polysubstituted aryl moiety of the formula:

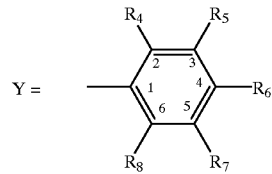

where $R_4$ and $R_8$ are alkyl, alkenyl, alkynyl, alkoxyl (—OR), alkylthiol (—SR), or substituted amino groups that serve to stabilize the -COX- linkage between the acridinium nucleus and the Y moiety, through steric and/or electronic effect; preferably $R_4$ and $R_8$ are low alkyl, more preferably methyl group, or at least one of them is as defined while the other is a hydrogen, if the $C_1$ or $C_8$ position of the acridinium nucleus is substituted with a low alkyl group, preferably also methyl;

$R_5$ and $R_7$ are any of $R_2$ and $R_3$ defined above;

$R_6$═—$R_9$—$R_{10}$, the key substituent containing necessary functional group for conjugating to biological molecule of interest, where $R_9$ is not required but optionally can be branched or straight-chained alkyl, substituted or unsubstituted aryl or aralkyl containing optionally up to heteroatoms, and $R_{10}$ is a leaving group or an electrophilic functional group attached with a leaving group including but not limited to:

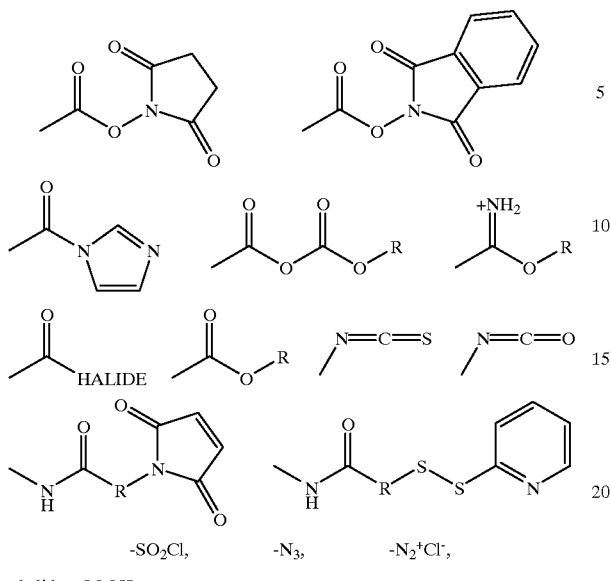

-SO₂Cl, -N₃, -N₂⁺Cl⁻, a halide, -COOH $R_{10}$ can also be —Q—R—Nu, —Q—R—(I)nNu—, —Q—Nu, —R—Nu, or —Nu, where n is a number of at least 1, Nu is a nucleophilic group, Q is a functional linkage, I is an ionic or ionizable group; detailed definitions of Nu, Q, and I can be found in the U.S. Pat. No. 5,241,070, column 3, line 45 to column 3, line 16. The reactions contemplated for Nu was also described in the same patent, column 3, line 48 to column 4, line 18.

$R_5$ and $R_6$, and $R_6$ and $R_7$ are interchangeable; and

When X is nitrogen, then Z is —SO₂—Y', Y' has the same definition of Y as described above, and both can be the same or different. Additionally, Y itself can be a branched or straight-chained alkyl containing optionally up to 20 carbon atoms, halogenated or unhalogenated, or a substituted aryl, or heterocyclic ring system.

The general structure of the set B chemiluminescent NIR acridinium compounds of the present invention can be schematically represented as follows:

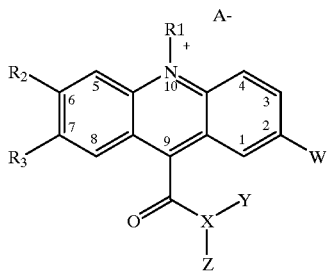

The definitions of $R_1$, $R_2$, $R_3$, A—, W, X, Y, and Z are the same as in set A NIR-AC general structure. The remaining $C_3$, $C_4$, $C_5$ peri-positions of the acridnium nucleus are optionally substituted. $R_3$ can also be the same as W in which case the acridinium ester has two electron donating groups instead of one. The disubstituted compounds are expected to show further bathochromic shifts in their emission maxima over their monosubstituted counterparts.

B. Biological Molecules Labeled with NIR-AC

NIR-AC functionalized with the previously mentioned chemically reactive functional groups and their obvious derivatives can be covalently coupled, directly or indirectly, both in vitro or in vivo, via a spacer or cross-linker (as described earlier in U.S. Pat. No. 5,656,426, and incorporated herein by reference) to:

(a) small organic biomolecules, haptens or ligands such as thyroid hormones, steroids, vitamins, antibiotics, enzyme cofactors, therapeutic drugs, metabolites, lipids, neurotransmitters, or controlled chemical substances, (b) macro-molecules such as bioactive proteins (including avidin, antibodies, DNA binding proteins, enzymes, histones, and others), polysaccharides, oligosaccharides, glycoproteins, glycosamino glycans, lectins, lipoproteins, lipopolysaccharides, isolated or intact RNA, DNA, oligonucleotides, proteins, peptides, inactivated proteins, hormones, viral antigens, bacterial antigens, eukaryotic antigens, immunoglobulin binding proteins, toxins, cytokines, antibody fragments, or receptor proteins, (c) higher order biological entities such as viruses, bacteria, eukaryotic cells, and sub-cellular components such as ribosomes.

The resulting covalent linkages such as amide, urea, and thioether are just a few examples most commonly anticipated by artisans skilled in the art. Other kinds of possible linkages that can be formed in organic (e.g. ether, ketone, ester, azo, etc.) or aqueous media (e.g. disulfide) and which are well recorded in literature should be considered obvious in the absence of a demonstration of unexpected benefits.

To illustrate how biological molecules such as nucleic acids, proteins, ligands or haptens can be conjuguated to an NIR-AC to form tracers useful in receptor binding, as well as for immuno and nucleic acid diagnostic tests, it was necessary to provide evidence that the NIR emission characteristics of free NIR-AC can be retained in the tracer. To this end the syntheses of an anti-TSH-3-HS-DMAE conjugate as well as a complementary, Vancomycin A oligonucleotide probe, conjugated to 2-OH-DMAE, are described in the examples section. The term, nucleic acid represents oligonucleotides typically synthesized in vitro using standard chemistry, and may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoramidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provide resistance to degradation without compromising affinity. Modification of the heterocyclic bases must maintain proper base pairing. Some useful substitutions include deoxyuridine for deoxythymidine; 5-methyl-2'-deoxycytidine and 5-bromo- 2'-deoxycytidine for deoxycytidine. 5-Propynyl-2'-deoxyuridine and 5-propynyl-2'-deoxycytidine have been shown to increase affinity and biological activity when substituted for deoxythymidine and deoxycytidine, respectively.

C. Applications of NIR-AC

The applications and benefits of NIR-AC are numerous. In the broadest sense, any applied diagnostic assays which might include but are not limited to the contemplated simultaneous use of more than one chemiluminescent compound as free molecules (such as in AE-encapsulated liposome technology, see U.S. Pat. Nos. 5,227,489; 5449,556; 5,595,875) or as conjugated labels for signaling purposes (as described earlier in U.S. Pat. Nos. 5,395,752; 5,702,887, the copending U.S. Pat. No. 5,879,894 and PCT application No. PCT/IB98/00831, and incorporated herein by reference), can benefit from the present invention. The presently described compounds are further improvements over the previously described LEAE and ETCs with respect to conventional AE, due to the better discrimination of their emission maxima and simplicity of design compared to ETCs. ETCs, as described in the copending PCT application number PCT/IB98/00831, are comprised of an acridinium ester covalently attached to a fluorophore. These conjugates are structurally complex and synthetically challenging. Furthermore, a method for conjugation to biomolecules is not always apparent. The NIR-AC of the present invention are structurally simpler by design than the ETCs and therefore, offer an effective alternative to ETCs for use with conventional acridinium compounds (blue emitting) and LEAE (green emitting) for simultaneous, multiple analyte assays. Thus, the NIR-AC invention has added to the family of acridinium compounds, another series of distinctive members characterized by their longer emission maxima. Moreover, taken in conjunction with our previous work, the invention has provided a broad picture for first enabling, and then improving the quality of simultaneous multi-analyte diagnostic tests.

With recent advances in photophysics, NIR-AC's can be employed in conjunction with improved light detectors such as the charge-coupled devices (CCDs), to take advantage of the intrinsically high quantum yield of these compounds. For example, a backed-illuminated thinned CCD with 1340× 700 pixels which can be cooled by various methods, is now commercially available (Princeton Instruments, Trenton, N.J.). This CCD has an extremely low dark count and read out noise while maintaining a high detection efficiency of 80–90% or better across the light emission range of 400–800 nm. In order to keep the readout noise at a low level and to avoid problems due to cosmic rays at the same time, it is very important to properly select the so-called binning of the CCD. Binning is defined as subdividing the total number of pixels on the CCD chip and grouping a number of pixels into a single photon sensing/detecting and signal exporting unit (also referred as superpixel) through electronic connection and software programming. The result of binning is therefore, the significant reduction of read out noise due to the great reduction in the number of signal exporting units (i.e. pixels vs. superpixels). Superpixels on the other hand should be kept at a sufficient number to cope with the great interference of cosmic rays which are ubiquitous and occur at the frequency of low number of seconds. Signal from an affected superpixel will have to be sacrificed through proper software programming in order not to greatly distort the accuracy of the total signal output. It is thus obvious that there is a counterbalancing need to tolerate low level of read out noise by maintaining a sufficient number of superpixels.

To improve the accuracy further and make up for the loss of the actual signal expected of the cosmic ray-affected superpixel(s), the number of photons originating from the luminescent sample under measurement, which have hit said affected superpixel(s), and therefore, the actual luminescence read out from said affected superpixel can be reconstructed by deriving or extrapolating from the read outs of the surrounding superpixels that are unaffected by the cosmic rays. Our theoretical calculations as well as experimental results showed that binning the 1340×700=938,000 pixels into 16 superpixels is optimal. Note that the currently available photomultiplier tube (PMT)-based detectors either show a precipitous drop in detection efficiency (from 15% to <1%) in the 500–650 nm range or are very noisy when they are designed to be more sensitive (detection efficiencies are 5–10%) in this region. The improved performance of CCDs is expected to enhance assay sensitivity primarily through the great reduction of the background signal contributed by the sample/buffer matrix in the same long wavelength region where there is a concurrent augmentation of NIR-AC detectability; consequently, providing the field of diagnostics with unprecedented assay performance. One embodiment for the CCD application is the modification of existing semi-automatic luminometers (e.g. MLA-II of Chiron Diagnostics) by replacing the PMT assembly with a CCD camera. Conceptually, the CCD can be oriented toward the sample chamber opening and brought to the closest possible proximity to detect the light emitted when chemiluminescence is triggered with alkaline hydrogen peroxide. A high transmission efficiency (95% plus) light pipe of proper shape can be installed between the chamber opening and the CCD detection window to improve the light collection efficiency. Utilizing or modifying the general mechanical and electrical connections for the MLA-II and CCD system interface in order to improve the prototype luminometer should be obvious to those skilled in the arts of photophysics and electrical engineering. A separate objective of this invention, therefore, is to point to a way by which the replacement of the current photo-multiplying tube (PMT)-based detector with a CCD would enhance the detectability of NIR-AE, thereby improving diagnostic assay sensitivity.

D. Light Emission Spectra

The light emission spectra of NIR-AC and the acridinium esters with shorter emission wavelengths were determined by a Fast Spectral Scanning System (FSSS) of Photo Research (a division of Kollmorgen Corp) of Burbank, Calif., U.S.A. The experiment was carried out in a dark room. Each compound was dissolved in acetonitrile or N,N-dimethylformamide, except for the protein-labeled conjugates and hydrophilic AE derivatives where aqueous solutions had to be used because of solubility. The resulting concentrates were diluted with the same solvent to form the working solution which upon reaction with alkaline hydrogen peroxide emitted light of adequate intensity. A typical experiment utilized 10~100 ug of the sample in 500 ul of the solvent contained in a 13×100 mm borosilicate test tube. The tube was placed into a test tube rack raised to a proper height. A piece of aluminum foil was placed at the back of the tube to enhance the detectability of the emitted light. The FSSS optical head was placed in front of the tube at an approximate distance of 130 mm with its lens focused on the liquid in the tube. The sample solution was first treated with 0.35 ml of the Flashing Reagent #1 (Chiron Diagnostics) containing 0.1 N $HNO_3$ and 0.1% $H_2O_2$. The room was then darkened, and 0.35 ml of the Flashing Reagent #2 (Chiron Diagnostics), containing 0.25 N NaOH and 0.2% ARQUAD was immediately added to the reaction mixture. (See U.S. Pat. No. 4,927,769 which is commonly assigned and incorporated herein by reference.) The light, which was generated instantaneously following the addition of the Reagent #2, was recorded by the FSSS for 5 seconds starting from about one second before the Reagent #2 was added. The various emission spectra determined on FSSS are given in FIG. 1, and are also summarized in Table 1.

mine label incorporation. This was easily accomplished by recording the masses of the underivatized and labeled proteins. From the observed mass differences, label incorporation could be calculated. These are described in examples 9–14. For the oligonucleotide conjugate, since the starting oligonucleotide was synthesized with only one reactive

TABLE 1

| No | Compound[+] | Range*[^] (nm) | Emission Max (nm) | Organic Solvent (%)[~] |
|---|---|---|---|---|
| | NIR-AC | | | |
| 1. | 3-HS-DMAE | 510–860 | 690 | MeCN/DMF (42) |
| 2. | 3-HS-DMAE-BSA | 500–800 | 610 | 0 |
| 3. | NSB-3-HS-DMAE-BSA | 500–800 | 620 | 0 |
| 4. | 2-OH-DMAE-Bz | 500–800 | 604 | MeCN/DMF (42) |
| 5. | 2-OH-DMAE-BSA | 500–780 | 594 | 0 |
| | AE's with shorter or very broad emission wavelength | | | |
| 6. | 3-HP-DMAE | 420–780 | Broad | MeCN/DMF (42) |
| 7 | NSB-3-MS-DMAE-Bz | 420–700 | 520 | MeCN/DMF (42) |
| 8. | 3-BS-DMAE-Bz | 430–700 | 520 | MeCN/DMF (42) |
| 9. | NSB-3-MS-DMAE | 420–720 | 522 | DMF (42) |
| 10. | NSB-3-MS-DMAE | 420–700 | 522 | MeCN (42) |
| 11. | NSB-3-MS-DMAE | 400–660 | 456 | 0 |
| 12. | NSB-2-BS-DMAE-Bz | 450–680 | 520 | MeCN/DMF (42) |
| 13. | NSB-3-MS-DMAE-NHS | 410–640 | 460 | 0 |
| 14. | NSB-3-MS-DMAE-BSA | 410–610 | 456 | 0 |
| 15. | NSB-3-MS-DMAE-anti-TSH | 410–600 | 456 | 0 |
| 16. | 2-HS-DMAE | 420–850 | Broad | MeCN/DMF (42) |
| 17. | 2-HS-DMAE-BSA | 420–620 | 482 | 0 |
| 18. | NSB-2-MS-DMAE-NHS | 400–680 | 454 | 0 |
| 19. | DMAE | 400–530 | 430 | DMF (42) |
| 20. | NSP-DMAE | 390–530 | 424 | DMF (42) |
| 21. | NSP-DMAE-BSA | 390–520 | 420 | 0 |
| 22. | LEAE-BZ | 490–670 | 522 | MeCN (42) |

*Range is set for spectral region with signal intensity of above 5% of peak height.
[^]Emission spectral range that goes beyond the scanning limit (380–780 nm) of FSSS, is extrapolated at the long end following the approximate trend of the curve
[~]The percentage of organic solvent in the final mix after flash reagents of #1 and #2 were added.
[+]The acronyms inside the table represent compounds, the full nomenclatures of which are given in the example section. NSP, MeCN and DMF stand for N-sulfopropyl, acetonitrile, and dimethylformamide, respectively.

E. Specific Activity

The chemiluminescent specific activities of various compounds and their conjugates are listed in Table 2. These values were determined either (a) on a Berthold luminometer (MLA-I, Chiron Diagnostics) fitted with a BG-38 filter (from Corion, Franklin, Mass.) with the wavelength transmission range of about 320 to 650 nm at transmission efficiency of 20–97%; or (b) on a prototype of a new instrument which comprised of an in-house semi-automatic luminometer (MLA-II) integrated to a back-illuminated, thinned, liquid nitrogen-cooled CCD detector from Princeton Instruments. The specific activities are therefore limited by the detectors used and the accessories selected.

Typically, each sample was prepared in acetonitrile or methanol (free labels) or water (conjugates). These stock solutions were diluted further into 10 mM phosphate pH 8 also containing 150 mM NaCl, 0.1% BSA, 0.05% sodium azide. Chemiluminescence of a 25 uL sample solution was initiated by the addition of Reagents 1 & 2 (Chiron Diagnostics) Typical dilutions of stock solutions resulted in overall observed RLUs in the range of $0.5-5 \times 10^6$ RLUs for a two second measurement time. From these measurements, the specific activity of the label could be calculated. For protein conjugates, since incorporation of more than one label per protein are possible, each conjugate was further characterized by MALDI-TOF mass spectrometry to determine label incorporation. This was easily accomplished by recording the masses of the underivatized and labeled proteins. From the observed mass differences, label incorporation could be calculated. These are described in examples 9–14. For the oligonucleotide conjugate, since the starting oligonucleotide was synthesized with only one reactive alkyl-amino group at the 5'-end (which can be labeled with NHS chemistry), the MALDI-TOF mass spectrum of this conjugate showed the expected incorporation of one label.

Protein concentrations were determined by a micro-Bradford assay (BioRad). From a knowledge of the protein concentration and the number of labels per protein, the concentration of the label that was being measured in the luminometer could be determined. Similarly, oligonucleotide-AE concentration, and hence acridinium ester concentration, was determined by recording the absorbance of the conjugate at 260 nm on a UV-spectrophotometer. Acridinium ester contribution relative to oligonucleotide to the absorption band at 260 nm is negligible. All specific activities listed in Table 2 are for single labels only.

The chemiluminescent specific activity of two compounds, 3-HS-DMAE and 2-OH-DMAE-NHS were measured on both luminometers which were described above. The observed specific activities clearly reflect the increased efficiency of the CCD in the red as opposed to conventional photomultiplier tube based detectors which the MLA-I was fitted with. Thus, 3-HS-DMAE is detected ~8-fold better with the CCD while 2-OH-DMAE-NHS is detected with a whopping 40-fold increase in detection efficiency with the CCD camera equipped luminometer. Further increases in the specific activities can be anticipated as the prototype of the modified luminometer is further refined. Thus, NIR-AC coupled with CCD based detectors offer the potential for maximal sensitivity in assays because of the negligible backgrounds normally observed from biological samples in the red, remarkable detector efficiency of the CCD as well as improved quantum yields at least for some compounds such as 2-OH-DMAE. Even in the case of 3-HS-DMAE, it must be noted that once this compound is conjugated to a protein its quantum efficiency increases >20-fold thus also making this an extremely useful NIR-AC.

TABLE 2

Specific Activity (RLU/mole) of NIR-AC Determined on MLA-I with Hamamatsu R268 PMT, and Corion BG38 optical filter and on MLA-II with back-illuminated, thinned, liquid $N_2$-cooled CCD detector

| | | RLU's/mol × $10^{-19}$ | |
|---|---|---|---|
| Compound/Conjugate+ | MW* | MLA-I | MLA-II |
| 3-HS-DMAE | 504.6 | 0.075 | 0.62 |
| 3-BS-DMAE-Bz | 685.8 | 3.8 | |
| 3-HS-DMAE-BSA | | 1.8 | |
| NSB-3-HS-DMAE-BSA | | 1.3 | |
| NSB-3-HS-DMAE-anti-TSH | | 3.6 | |
| NSB-3-MS-DMAE-NHS | 736.8 | 10 | |
| 2-HS-DMAE | 504.6 | 0.012 | |
| NSB-2-MS-DMAE-NHS | 736.8 | 3.9 | |
| 2-OH-DMAE | 402.4 | 0.49 | 20.2 |
| 2-OH-DMAE-Oligonucleotide | | 0.45 | |
| 3-HP-DMAE | 479.5 | 0.054 | |
| DMAE-Bz | 476.6 | 10 | |

+The acronyms inside the table represent compounds, the full nomenclatures of which are given in the example section.
*Molecular Weights (MW) of the labels were calculated without the inclusion of counter ion.

EXAMPLE 1

Synthesis of 2',6'-dimethyl-4'-carboxyphenyl 3-(4-hydroxystyrenyl)-10-methyl-acridinium-9-carboxylate (3-HS-DMAE) and its N-succinimidyl ester (3-HS-DMAE-NHS)

Synthesis of N-[3-(1,3-dioxolyl)phenyl]isatin

Isatin (3.2 g, 0.0218 mol) was dissolved in anhydrous DMF (75 mL) and cooled in an ice-bath under a nitrogen atmosphere. To this cold solution, sodium hydride (0.575 g, 0.0239 mol) was added and the reaction was stirred at 0° C. for 1.5 hours. This solution was then treated with 2-(3-bromophenyl)-1,3-dioxolane (5 g, 1 equivalent) followed by CuI (8.3 g, 2 equivalents). The resulting suspension was heated in an oil-bath under nitrogen at 130–140° C. for 16 hours. It was then cooled to room temperature and diluted with an equal volume of chloroform. This suspension was filtered and the filtrate was concentrated under reduced pressure. A viscous brown oil was recovered which was suspended in xylenes (150 mL) wand evaporated to dryness. The residue was used as such for the next reaction. TLC (5% methanol in chloroform) showed clean conversion; Rf (product)=0.86.

Synthesis of 2-(acridine-9-carboxyl)-1,3-dioxolane

Crude N-[3-(1,3-dioxolyl)phenyl]isatin from above was suspended in 10% KOH (150 mL) and the resulting suspension was refluxed under nitrogen for 4.5 hours. The reaction was then cooled to room temperature and filtered. The filtrate was diluted with ice and acidified with 20–30% HCl till weakly acidic. A yellow precipitate separated out which was collected by filtration and air dried. Yield ~5 g, yellow sticky solid which was used as such for the next reaction.

Synthesis of acridine-9-carboxylic acid-3-carboxaldehyde

Crude 2-(acridine-9-carboxyl)-1,3-dioxolane (5 g) was suspended in 80% aqueous acetic acid (100 mL). This suspension was heated at 80° C. under nitrogen for 16 hours. A yellow precipitate had appeared in the reaction. The reaction mixture was then cooled to room temperature and diluted with anhydrous ether (~500 mL). The precipitated solid was collected by filtration, rinsed with ether and air dried. It was then transferred to a round bottom flask, suspended in toluene (50 mL) and evaporated to dryness. This process was repeated once more. A bright yellow solid was recovered. Yield=1.72 g (31% overall). MALDI-TOF MS 252.3 obs. (251.24 calc.).

Synthesis of 2',6'-dimethyl-4'-benzyloxycarbonylphenyl acridine-9-carboxylate-3-carboxaldehyde Acridine-9-carboxylic acid-3-carboxaldehyde (0.3 g, 0.0012 mol) in pyridine (50 mL) was cooled in an ice-bath under nitrogen and treated with p-toluenesulfonyl chloride (0.456 g, 0.00239 mol). The reaction was stirred at 0° C. for 15 minutes and then 2,6-dimethyl-4-benzyoxycarbonyl-phenol (0.306 g, 1 equivalent) was added. The reaction was warmed to room temperature and stirred for 48 hours under nitrogen and then concentrated under reduced pressure. The residue was dissolved in chloroform which was then washed with aqueous bicarbonate and aqueous ammonium chloride. The organic layer was separated, dried over magnesium sulfate and concentrated under reduced pressure. The crude residue (0.6 g) was purified by preparative TLC on silica using 10% ethyl acetate in chloroform; Rf (product)=0.6. Yield=0.24 g (41%); bright yellow solid. MALDI-TOF MS 490.78 obs. (489.53 calc.).; $^1$H-NMR (CDCl$_3$) 2.46 (s, 6H), 5.40 (s, 2H), 7.37–7.50 (m, 5H), 7.78 (m, 1H), 7.94 (m, 3H), 8.12 (d, 1H, J=9.3 Hz), 8.39 (d, 1H, J=8.6 Hz), 8.45 (d, 1H, J=8.6 Hz), 8.51 (d, 1H, J=9.2 Hz), 8.79 (s, 1H), 10.31 (s, 1H).

Synthesis of 4-benzyloxybenzyltriphenyl phosphonium chloride

4-Benzyloxybenzyl chloride (1 g, 0.0043 mol) and triphenyl phosphine (1.127 g, 1 equivalent) in anhydrous toluene (20 mL) were refluxed under nitrogen for ~8–10 hours. A white precipitate appeared in the reaction mixture. The reaction mixture was then cooled to room temperature and ether (100 mL) was added. The precipitated phosphonium salt was collected by filtration, rinsed with ether and air dried. Yield=0.55 g (25%). MALDI-TOF MS 459.51 obs. (459.54 calc.).

Synthesis of 2',6'-dimethyl-4'-benzyoxycarbonylphenyl 3-(4-benzyloxystyrenyl)-acridine-9-carboxylate 4-Benzyloxybenyltriphenyl phosphonium chloride (0.475 g, 0.00096 mol) was suspended in anhydrous THF (10 mL) and cooled to −78° C. in an acetone-dry ice bath under nitrogen. n-Butyl lithium (0.6 mL of 1.6 M solution, 1 equivalent) was added dropwise. A reddish-orange color appeared instantly. The reaction was stirred at −78° C. for one hour and then a solution of 2',6'-dimethyl-4'-benzyoxycarbonylphenyl acridine-9-carboxylate-3-carboxaldehyde (0.469 g, 0.00096 mol) was added dropwise in dry THF (15 mL). The reaction was stirred for 3 hours at −78° C. and then diluted with ethyl acetate and aqueous ammonium chloride. The organic layer was separated and washed once with brine. It was then dried over magnesium sulfate and concentrated under reduced pressure. TLC (45% chloroform, 50% Hexanes, 5% ethyl acetate) of the residue showed a mixture of the E and Z isomers in a ~1:1 ratio; Rf=0.43 and 0.31. Purification by flash chromatography on silica gel using 7% ethyl acetate, 23% chloroform, 70% hexanes, resulted in complete isomerization to only one isomer (E). Evaporation of the flash fractions yielded a yellowish-orange solid. Yield=0.25 g (39%). MALDI-TOF-MS 671.2 obs. (670.78 calc.).; $^1$H-NMR (CDCl$_3$) 2.48 (s, 6H), 5.12 (s, 2H), 5.40 (s, 2H), 7.03 (d, 2H, J=8.7 Hz), 7.23 (d, 1H, J=18 Hz, E-olefin), 7.35–7.49 (m, 11H), 7.56 (d, 2H, J=8.7 Hz), 7.65 (m, 1H), 7.85 (m, 1H), 7.93 (m, 3H), 8.25 (s, 1H), 8.30 (d, 1H, J=8.6 Hz), 8.37 (d, 1H), 8.40 (d, 1H).

Synthesis of 2',6'-dimethyl-4'-benzyloxycarbonylphenyl 3-(4-benzyloxystyrenyl)-10-methyl acridinium-9-carboxylate trifluoromethanesulfonate (3-BS-DMAE-Bz)

A solution of 2',6'-dimethyl-4'-benzyloxycarbonylphenyl 3-(4-benzyloxystyrenyl)-acridine 9-carboxylate (50 mg, 75 umoles) in dichloromethane (5 mL) was treated with methyl triflate (125 uL, 15 equivalents). The reaction was stirred at room temperature. After 24 hours, HPLC analysis using a C18 column (3.9×300 mm) and a 30 minute gradient of 10→100% MeCN/water each containing 0.05% TFA at a flow of 1 ml/min. and UV detection at 260 nm showed Rt (product)=29 min., Rt (starting material)=32 min. (~74% conversion). The reaction was concentrated under reduced pressure and the residue was suspended in ethyl acetate and evaporated to dryness to afford a purple sticky solid. This material was used as such for the next reaction. MALDI-TOF MS 685.1 obs. (685.81 calc.).

Synthesis of 2',6'-dimethyl-4'-carboxyphenyl 3-(4-hydroxystyrenyl)-10-methyl-acridinium-9-carboxylate (3-HS-DMAE)

2',6'-Dimethyl-4'-benzyloxycarbonylphenyl 3-(4-benzyloxystyrenyl)-10-methyl-acridinium-9-carboxylate (11 mg) was stirred in a mixture of dimethyl sulfide (2 mL) and 30% HBr in acetic acid (1 mL). After 4 hours at room temperature, ether+hexanes (20 mL, 1:1) was added and the precipitated solid was collected by filtration and rinsed with ether. The residue was dissolved in methanol and concentrated under reduced pressure. HPLC analysis as described above showed Rt (product)=17 minutes. The product was isolated by preparative HPLC using a 20×300 mm column. The HPLC fraction containing the product was evaporated to dryness to afford a purple solid. Yield=5 mg (63%). MALDI-TOF MS 504.98 obs. (504.56 calc.).

Synthesis of 2',6'-dimethyl-4'-N-succinimidyloxycarbonylphenyl 3-(4-hydroxystyrenyl)-10-methyl-acridinium-9-carboxylate (3-HS-DMAE-NHS)

A solution of 2',6'-dimethyl-4'-carboxyphenyl 3-(4-hydroxystyrenyl)-10-methyl-acridinium-9-carboxylate (5 mg) in DMF (10 mL) was treated with N-hydroxysuccinimide (8.8 mg, 10 equivalents) and dicyclohexylcarbodiimide (15.7 mg, 10 equivalents). The reaction was stirred at room temperature for 16 hours. HPLC analysis as described above showed Rt (product)=21 min. The product was purified by preparative HPLC using a 20×300 mm column and the HPLC fraction containing the product was lyophilized to dryness. Yield 9.4 mg (quant.). MALDI-TOF MS 601.63 obs. (601.64 calc.).

EXAMPLE 2

Synthesis of 2',6'-dimethyl-4'-N-succinimidyloxycarbonylphenyl 3-(4-hydroxystyrenyl)-10-sulfobutyl-acridinium-9-carboxylate (NSB-3-HS-DMAE-NHS)

Synthesis of 2',6'-dimethyl-4'-benzyloxycarbonylphenyl 3-(4-benzyloxystyrenyl)-10-sulfobutyl-acridinium-9-carboxylate (NSB-3-BS-DMAE-Bz)

2',6'-Dimethyl-4'-benzyoxycarbonylphenyl 3-(4-benzyloxystyrenyl)-acridine-9-carboxylate (24 mg) and 1,4-butane sultone (2 mL) were heated in an oil-bath at ~150° C. under nitrogen for 16 hours. It was then cooled to room temperature and ether (25 mL) was added to precipitate the product which was collected by filtration to afford a purple solid. HPLC analysis using a C18 column (3.9×300 mm) and a 30 minute gradient of 10→100% MeCN/water each containing 0.05% TFA at a flow rate of 1 mL/min. and UV detection at 260 nm showed Rt (product)=29 min.; Rt (starting material)=32 min (40% conversion). The crude material (30–40 mg) was used as such for the next reaction.

Synthesis of 2',6'-dimethyl-4'-carboxyphenyl 3-(4-hydroxystyrenyl)-10-sulfobutyl-acridinium-9-carboxylate (NSB-3HS-DMAE)

Crude 2',6'-dimethyl-4'-benzyloxycarbonylphenyl-3-(4-benzyloxystyrenyl)-10-sulfobutyl-acridinium-9-carboxylate (30–40 mg) was stirred in a mixture of dimethyl sulfide (2 mL) and 30% HBr in acetic acid (5 mL) for 4 hours. Ether (75 mL) was added and a dark purple solid separated out. The ether was decanted and the residue was rinsed with ether and air dried. Crude yield=30 mg. HPLC analysis as described above showed Rt (product)=16 minutes. This material was used as such for the next reaction. MALDI-TOF MS 627.39 obs. (625.7 calc.).

Synthesis of 2',6'-dimethyl-4'-N-succinimidyloxycarbonylphenyl 3-(4-hydroxystyrenyl)-10-sulfobutyl-acridinium-9-carboxylate (NSB-3-HS-DMAE-NHS)

Crude 2',6'-dimethyl-4'-carboxyphenyl 3-(4-hydroxystyrenyl)-10-sulfobutyl-9-acridinium carboxylate (15 mg) was dissolved in a mixture of MeCN (2 mL) and DMF (1 mL). N-Hydroxysuccinimide (8.5 mg, 73.9 umoles) and dicyclohexylcarbodiimide (11 mg, 53.4 umoles) were added and the reaction was stirred at room temperature for 16 hours. HPLC analysis as described earlier showed Rt (product)=19 minutes. The product was purified by preparative HPLC using a 10×250 mm column at a solvent flow rate of 4 mL/min. The HPLC fraction containing the product was lyophilized to dryness to afford a purple powder. Yield=5.6 mg (42% overall, three steps). MALDI-TOF MS 724.66 obs. (722.77 calc.).

EXAMPLE 3

Synthesis of 2',6'-dimethyl-4'-N-succinimidyloxycarbonylphenyl 3-(4-methoxystyrenyl)-10-sulfobutyl-acridinium-9-carboxylate (NSB-3-MS-DMAE-NHS)

Synthesis of 4-methoxybenzyltriphenyl phosphonium chloride

A solution of 4-methoxybenzyl chloride (1.153 g, 0.0074 mol) in anhydrous toluene (10 mL) was treated with triphenylphosphine (1.93 g, 1 equivalent). The resulting solution was refluxed under nitrogen. After 8–10 hours, the reaction was cooled to room temperature and diluted with ether. The phosphonium salt was collected by filtration. Yield=1.5 g (53%); MALDI-TOF MS 383.9 obs. (383.45 calc.).

Synthesis of 2',6'-dimethyl-4'-benzyloxycarbonylphenyl 3-(4-methoxystyrenyl)-acridine-9-carboxylate A suspension of 4-methoxybenzyltriphenylphosphonium chloride (0.11 g, 0.25 mmol) in anhydrous THF (5 mL) was cooled to −78° C. in a acetone-dry ice bath under nitrogen and treated with n-butyl lithium (0.25 mL of 1.6 M, 1.3 equivalents). An orange-red color appeared. The reaction was stirred at −78° C. for 0.5 hour and then a solution of 2',6'-dimethyl-4'-carboxybenzylphenyl acridine-9-carboxylate-3-carboxaldehyde (0.1 g, 0.2 mmol) in anhydrous THF (5 mL) was added dropwise. The resulting solution was stirred in the acetone-dry ice bath for 0.5 hour and then warmed to room temperature over 0.5 hour. It was then diluted with ethyl acetate (40 mL) and the resulting solution was washed twice with aqueous ammonium chloride. The organic layer was dried over magnesium sulfate and concentrated under reduced pressure. TLC (5:3:2, hexanes, chloroform, ethyl acetate) showed a mixture of E and Z olefins; Rf (E-isomer)=0.54, Rf (Z-isomer)=0.69. The products were isolated by preparative TLC on silica gel. Partial isomerization of the Z isomer to the E isomer was observed during purification. Yield=31 mg (E), 43 mg (E+Z), total yield=74 mg (61%), MALDI-TOF MS (E-isomer) 594.7 obs. (594.7 calc.); $^1$H-NMR (CDCl$_3$) 2.48 (s, 6H), 3.86 (s, 3H), 5.40 (s, 2H), 6.95 (d, 2H, J=8.7 Hz), 7.24 (d, 1H, J=17 Hz, E-olefin), 7.34–7.50 (m, 6H), 7.56 (d, 2H, J=8.7 Hz), 7.65 (m, 1H), 7.85 (m, 1H), 7.95 (m, 3H), 8.26 (s, 1H), 8.31 (d, 1H, J=8.6 Hz), 8.37 (d, 1H, J=9.2 Hz), 8.39 (d, 1H, J=8.7 Hz).

Synthesis of 2',6'-dimethyl-4'-benzyloxycarbonylphenyl 3-(4-methoxystyrenyl)-10-sulfobutyl-acridinium-9-carboxylate (NSB-3-MS-DMAE-Bz)

2',6'-Dimethyl-4'-benzyloxycarbonylphenyl 3-(4-methoxystyrenyl)-acridine-9-carboxylate (10 mg, E isomer) was mixed with 1,4-butane sultone (~1 mL) and the mixture was heated in an oil-bath at 140° C. under nitrogen for 16 hours. The reaction was then cooled to room temperature and ethyl acetate was added. The precipitated solid was collected by filtration and dissolved in DMF+MeCN. This was concentrated under reduced pressure to afford a sticky solid which was used as such without purification for the next reaction. HPLC analysis using a C18 column (3.9×30 mm) and a 30 minute gradient of 10→100% MeCN/water each containing 0.05% TFA at a flow rate of 1 mL/min., and UV detection at 260 nm showed Rt (product)=24.8 min. MALDI-TOF MS 731.7 obs. (729.9 calc.).

Synthesis of 2',6'-dimethyl-4'-carboxyphenyl 3-(4-methoxystyrenyl)-10-sulfobutyl-acridinium carboxylate (NSB-3-MS-DMAE)

2',6'-Dimethyl-4'-benzyloxycarbonylphenyl 3-(4-methoxystyrenyl)-10-sulfobutyl-acridinium-9-carboxylate from above (crude) was stirred in a 2:1 mixture of dimethyl sulfide and 30% HBr in acetic acid (1.5 mL). After ~3 hours, ether was added and the precipitated solid was collected by filtration and rinsed with ether. The residue was dissolved in methanol and concentrated under reduced pressure. HPLC analysis using the protocol described above showed Rt (product)=17 minutes. Yield=5.6 mg (64% 2 steps); MALDI-TOF MS 641.25 obs. (639.7 calc.).

Synthesis of 2',6'-dimethyl-4'-N-succinimidyloxycarbonylphenyl 3-(4-methoxystyrenyl)-10-sulfobutyl-acridinium-9-carboxylate (NSB-3-MS-DMAE-NHS)

A solution of 2',6'-dimethyl-4'-carboxyphenyl-3-(4-methoxystyrenyl)-10-sulfobutyl-acridinium-9-carboxylate (5.6 mg crude, 8.75 umoles) was dissolved in DMF (1 mL) and treated with N-hydroxysuccinimide (5 mg, 43.5 umoles) and dicyclohexylcarbodiimide (53.4 umoles). The reaction was stirred at room temperature for 16 hours. HPLC analysis as described above showed Rt (product)=20 min. This was isolated by preparative HPLC on a 10×250 mm column. The HPLC fraction containing the product was lyophilized to dryness. Yield=2 mg (31%); MALDI-TOF MS 737.8 obs. (736.8 calc.).

Scheme 1
Synthesis of 3-Substituted AE Derivatives

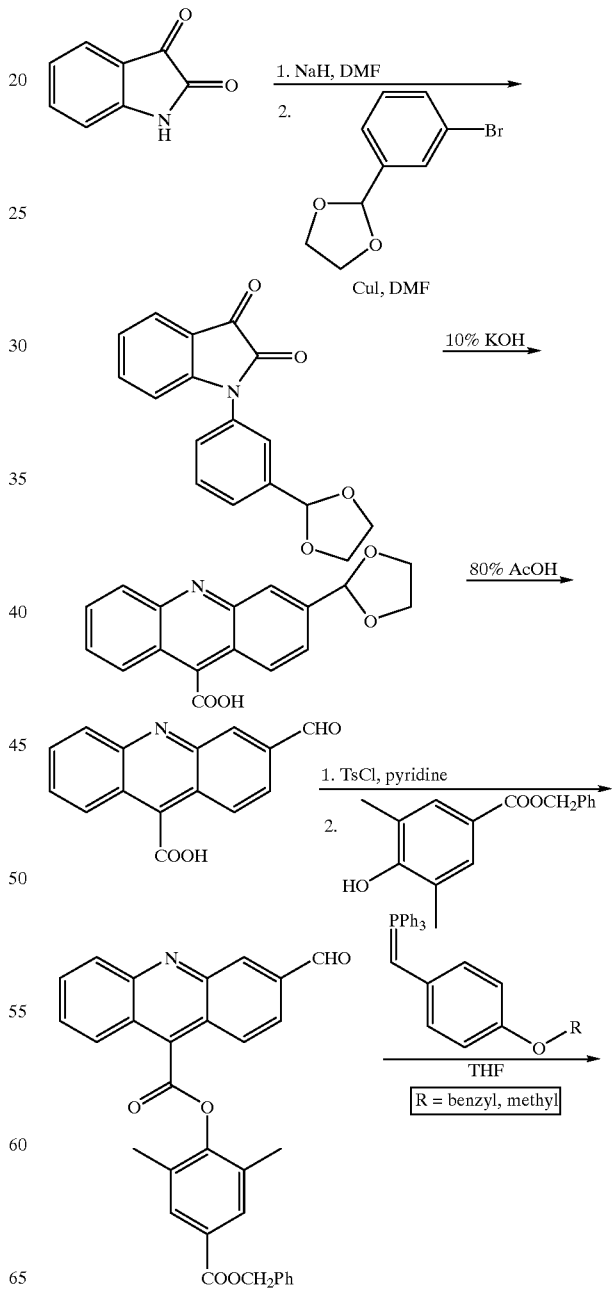

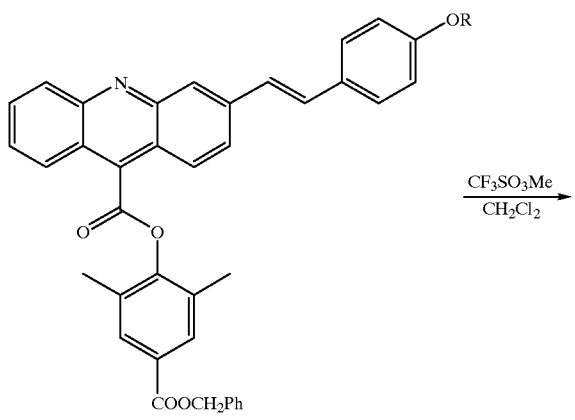
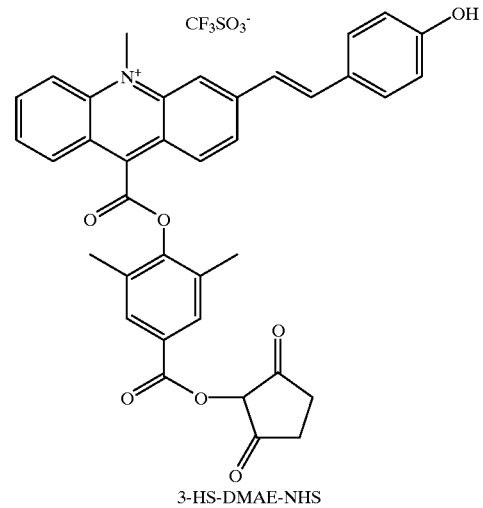
3-HS-DMAE-NHS
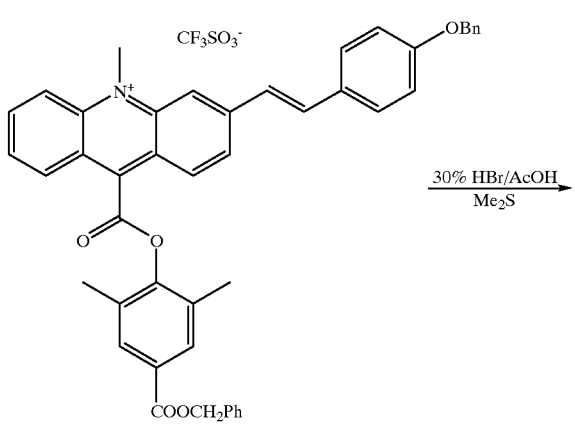
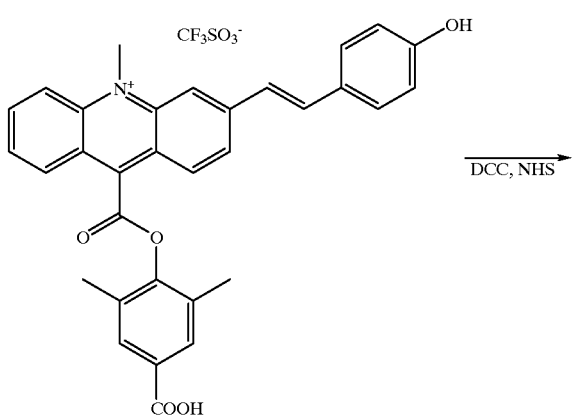
3-HS-DMAE
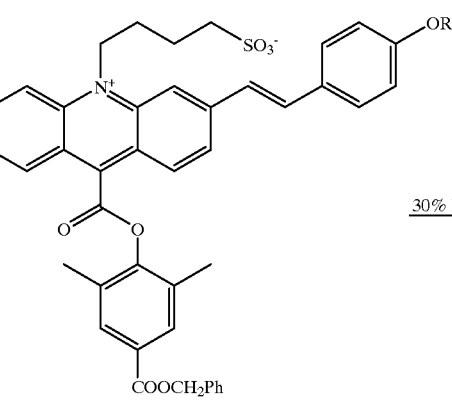
R = benzyl, methyl

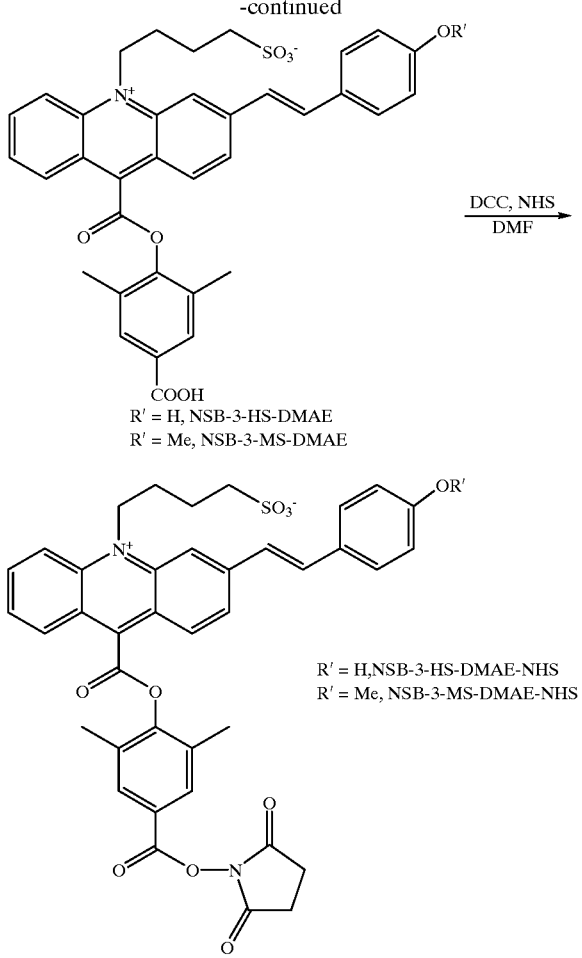

R' = H, NSB-3-HS-DMAE
R' = Me, NSB-3-MS-DMAE

R' = H, NSB-3-HS-DMAE-NHS
R' = Me, NSB-3-MS-DMAE-NHS

EXAMPLE 4

Synthesis of 2',6'-dimethyl-4'-carboxyphenyl 2-(4-hydroxystyrenyl)-10-methyl-acridinium-9-carboxylate (2-HS-DMAE)

Synthesis of 2-(4-bromophenyl)-1,3-dioxolane

4-Bromobenzaldehyde (3 g, 0.0162 mol) in benzene (60 mL) was treated with p-toluenesulfonic acid monohydrate (0.15 g, 0.79 mmol) and ethylene glycol (5 mL, 0.0896 mol). The reaction was refluxed under nitrogen with azeotropic removal of water. After 3 hours, the reaction was cooled to room temperature and diluted with an equal volume of ethyl acetate. This solution was washed twice with aqueous bicarbonate, dried over magnesium sulfate and concentrated under reduced pressure. A colorless oil was recovered. Yield=2.83 g (92%). TLC (5% ethyl acetate in hexanes) showed clean product, Rf=0.17.

Synthesis of N-[4-(1,3-dioxolyl)phenyl]isatin

Isatin (1.88 g, 0.0128 mol) in anhydrous DMF (100 mL) was cooled in an ice-bath under nitrogen and treated with sodium hydride (0.3 g, 1 equivalent). The reaction was warmed to room temperature and stirred for 1 hour. It was then treated with 2-(4-bromophenyl)-1,3-dioxalane (2.83 g, 0.0124 mol) followed by CuI (4.71 g, 2 equivalents). This suspension was heated in an oil-bath at 135° C. under nitrogen for 16 hours. It was then cooled to room temperature and diluted with an equal volume of chloroform. The resulting suspension was filtered and the filtrate was concentrated under reduced pressure. The residue was suspended in xylenes (100 mL) and evaporated to dryness. A thick, viscous oil was recovered which was used as such for the next reaction. TLC (5% methanol in chloroform) showed clean conversion, Rf (product)=0.91.

Synthesis of 2-(acridine-9-carboxyl)-1,3-dioxolane

The crude product from above, N-[4-(1,3-dioxolyl)phenyl]isatin, was suspended in 10% KOH (100 mL) and the suspension was refluxed under nitrogen for 4–5 hours. The reaction was then cooled to room temperature and filtered. The filtrate was chilled in ice and acidified with ice-cold concentrated HCl. A thick yellow precipitate appeared which was collected by filtration and air dried. Yield=2 g. This crude product was used as such for the next reaction. MALDI-TOF MS 295.31 obs. (295.29 calc.).

Synthesis of acridine-9-carboxylic acid-2-carboxaldehyde

Crude 2-(acridine-9-carboxyl)-1,3-dioxolane (2 g) was suspended in 80% aqueous acetic acid (100 mL) and heated at 75–80° C. in an oil-bath under nitrogen for 16 hours. The reaction was then cooled to room temperature and poured into ether (300 mL). A bright yellow solid separated out which was collected by filtration and rinsed with ether. The product was transferred to a round bottom flask and suspended in toluene (50 mL) and evaporated to dryness to yield a yellow powder. Yield=1.5 g (47%). MALDI-TOF MS 251.1 obs. (251.24 calc.).

Synthesis of 2',6'-dimethyl-4'-benzyloxycarbonylphenyl acridine-9-carboxylate-2-carboxaldehyde A solution of acridine-9-carboxylic acid-2-carboxaldehyde (0.3 g, 0.0012 mol) in pyridine (50 mL) was cooled in an ice-bath under nitrogen and treated with p-toluenesulfonyl chloride (0.455 g, 2 equivalents). The reaction was stirred at 0° C. for 10 minutes and then 2,6-dimethyl-4-benzyloxycarbonylphenol (0.306 g, 1 equivalent) was added. The reaction was warmed to room temperature and stirred for 48 hours. The reaction mixture was then concentrated under reduced pressure and the residue was dissolved in chloroform. The chloroform solution was washed with aqueous bicarbonate and aqueous ammonium chloride. The organic layer was then dried over magnesium sulfate and concentrated under reduced pressure. The crude residue (0.6 g) was purified by preparative TLC on silica gel using 10% ethyl acetate in chloroform; Rf (product)=0.57. Yield=0.24 g (41%). MALDI-TOF MS 489.1 obs. (489.53 calc.).; $^1$H-NMR (CDCl$_3$) 2.50 (s, 6H), 5.40 (s, 6H), 7.42 (m, 5H), 7.77 (dd, 1H), 7.97 (m, 3H), 8.32 (d, 1H, J=8.9 Hz), 8.42–8.49 (m, 3H), 8.99 (s, 1H), 10.23 (s, 1H).

Synthesis of 2',6'-dimethyl-4'-benzyoxycarbonylphenyl 2-(4-benzyloxystyrenyl)-acridine-9-carboxylate 4-Benzyloxyphosphonium chloride (0.1 g, 0.2 mmol) in anhydrous THF (5 mL) was cooled to −78° C. in an acetone-dry ice bath under nitrogen and treated with n-butyl lithium (0.15 mL of 1.6 M, 1.3 equivalents). A pale orange color appeared. The reaction was stirred at −78° C. for 1 hour and then a solution of 2',6'-dimethyl-4'-benzyloxycarbonylphenyl acridine-9-carboxylate-2-carboxaldehyde (90 mg, 0.9 equivalents) was added dropwise as a solution in anhydrous THF (5 mL). The reaction was stirred at −78° C. for 0.5 hour and then warmed to room temperature over 0.5 hour. The reaction was then diluted with ethyl acetate (50 mL) and aqueous ammonium chloride (200 mL). The organic layer was separated and dried over magnesium sulfate. Concentration afforded crude product (0.17 g) which by TLC (6:3:1 hexanes, chloroform, ethyl acetate) showed a mixture of Z (Rf=0.63) and E (Rf=0.75) olefins. The two isomers were separated by preparative TLC on silica gel. As observed before, partial isomerization of the Z isomer to a mixture of E and Z isomers was observed. Yield=100 mg (combined yield, 81%); E=44 mg, E+Z=56 mg. MALDI-TOF MS (E-olefin) 671.37 obs. (670.78 calc.); $^1$H-NMR (CDCl$_3$) 2.51 (s, 6H), 5.12 (s, 2H), 5.40 (s, 2H), 7.01 (d, 2H, J=8.7 Hz), 7.16 (d, 1H, J=16.3 Hz), 7.32–7.52 (m, 11H), 7.67 (m, 1H), 7.84 (m, 1H), 7.96 (s, 2H0, 8.14 (d, 1H, J=9.2 Hz), 8.32 (m, 3H), 8.41 (d, 1H, J=8.7 Hz).

Synthesis of 2',6'-dimethyl-4'-benzyloxycarbonylphenyl 2-(4-benzyloxystyrenyl)-10-methyl-acridinium-9-carboxylate (2-BS-DMAE-Bz)

A solution of 2',6'-dimethyl-4'-carboxybenzylphenyl-2-(4-benzyloxyphenyl) acridine-9-carboxylate (13.5 mg, 20 umoles) in dichloromethane (1.5 mL) was treated with methyl trifluoromethanesulfonate (116 uL, 50 equivalents). The reaction was stirred at room temperature for 16 hours. HPLC analysis on a C18 column (3.9×30 mm) and a 30 minute gradient of 10→100% MeCN/water each containing 0.05% TFA at a flow of 1 mL/min. and UV detection at 260 nm showed Rt (product)=24.5 min. The reaction mixture was concentrated and the crude mixture was used directly for the next reaction. MALDI-TOF MS 685.67 obs. (685.81 calc.).

Synthesis of 2',6'-dimethyl-4'-carboxyphenyl 2-(4-hydroxystyrenyl)-10-methyl-acridinium-9-carboxylate (2-HS-DMAE)

The crude product mixture from above was stirred in a mixture of dimethyl sulfide (1 mL) and 30% HBr in acetic acid (0.5 mL) at room temperature. After 4 hours, ether (50 mL) was added and the precipitated solid was collected by filtration. The solid was dissolved in MeOH+MeCN and concentrated. HPLC analysis using the protocol described above showed Rt (product)=17 min. The product was purified by preparative HPLC using a 20×300 mm column. The HPLC fraction containing the product was lyophilized to dryness to afford a dark purple solid. Yield=7.6 mg (76%, two steps); MALDI-TOF MS 504.9 obs. (504.6 calc.).

EXAMPLE 5

Synthesis of 2',6'-dimethyl-4'-N-succinimidyloxycarbonylphenyl 2-(4-methoxystyrenyl)-10-sulfobutyl-acridinium-9-carboxylate (NSB-2-MS-DMAE-NHS)

Synthesis of 2',6'-dimethyl-4'-benzyloxycarbonylphenyl 2-(4-methoxystyrenyl)-acridine-9-carboxylate 4-Methoxybenzyltriphenylammonium chloride (85 mg, 0.0002 mol) was suspended in THF (5 mL) and cooled to −78° C. in an acetone-dry ice bath under nitrogen. N-Butyl lithium (0.15 mL of 1.6 M, 1.2 equivalents) was added and the reaction was stirred at −78° C. under nitrogen for an additional 30 minutes. To this was added a solution of 2',6'-dimethyl-4'-benzyloxycarbonylphenyl acridine-9-carboxylate-2-carboxaldehyde (75 mg, 0.15 mmol) in anhydrous THF (5 mL). The reaction was stirred at −78° C. for 30 minutes and then warmed to room temperature over 30 minutes. The reaction was then diluted with ethyl acetate (40 mL) and the resulting solution was washed twice with aqueous ammonium chloride. The organic layer was separated and dried over magnesium sulfate. It was then concentrated under reduced pressure. TLC (5:3:2, hexanes, chloroform, ethyl acetate) showed a mixture of E (Rf=0.59) and Z (Rf=0.65) olefins. The two products were purified by preparative TLC. Combined yield=61 mg (67%); E=24 mg; E+Z=37 mg (isomerization of Z to E observed during purification). MALDI-TOF MS (E isomer) 595.6 obs. (594.7 calc.); $^1$H-NMR (CDCl$_3$) 2.51 (s, 6H), 3.86 (s, 3H), 5.40 (s, 2H), 6.94 (d, 2H, J=8.7 Hz), 7.15 (d, 1H. J=16.2 Hz), 7.32–7.53 (m, 6H), 7.67 (m, 1H), 7.84 (m, 1H), 7.96 (s, 2H), 8.14 (d, 1H, J=9.2 Hz), 8.31 (m, 3H), 8.41 (d, 1H, J=8.6 Hz).

Synthesis of 2',6'-dimethyl-4'-benzyloxycarbonylphenyl 2-(4-methoxystyrenyl)-10-sulfobutyl-acridinium-9-carboxylate (NSB-2-MS-DMAE-Bz)

2',6'-Dimethyl-4'-benzyloxycarbonylphenyl 2-(4-methoxystyrenyl)-acridine-9-carboxylate (19 mg, 32 umoles) was mixed with 1,4-butane sultone (3–4 mL) and the mixture was heated in an oil-bath under nitrogen at 140° C. for 16 hours. The reaction was then cooled to room temperature and diluted with ethyl acetate (40 mL). The precipitated solid was collected by filtration. This was dissolved in DMF and concentrated under reduced pressure. A dark, purple solid was recovered which was used directly for the next reaction. HPLC analysis using a C18 column and a 30 minute gradient of 10→100% MeCN/water each containing 0.05% TFA at 1 ml/min/and UV detection at 260 nm showed Rt (product)=25 minutes. MALDI-TOF MS Synthesis of 2',6'-dimethyl-4'-carboxyphenyl 2-(4-methoxystyrenyl)-10-sulfobutyl-acridinium-9-carboxylate (NSB-2-MS-DMAE)

The crude material from above was stirred in a mixture of dimethyl sulfide (1 mL) and 30% HBr in acetic acid (0.5 mL) for 4 hours at room temperature. Ether (50 mL) was added and the precipitated solid was collected by filtration. The residue was dissolved in DMF and concentrated under reduced pressure. The recovered reside was suspended in toluene and evaporated to dryness. Crude Yield=4.5 mg (~22%). HPLC analysis using the above protocol showed Rt (product)=15 minutes. MALDI-TOF MS Synthesis of 2',6'-dimethyl4'-N-succinimidyloxycarbonylphenyl 2-(4-methoxystyrenyl)-10-sulfobutyl-acridinium-9-carboxylate (NSB-2-MS-DMAE-NHS)

2',6'-Dimethyl4'-carboxyphenyl 2-(4-methoxystyrenyl)-10-sulfobutyl-9-acridinium carboxylate (5.6 mg) was dissolved in DMF (1 mL) and treated with N-hydroxysuccinimide (5 mg, 43.5 umoles) and dicyclohexylcarbodiimide (10 mg, 48.5 umoles). The reaction was stirred at room temperature for 16 hours. HPLC analysis as described above showed Rt (product)=19 minutes. The product was isolated by preparative HPLC using a 10×250 mm column and the HPLC fraction containing the product was lyophilized to dryness. A purple powdery solid was recovered. Yield=0.6 mg (12%); MALDI-TOF MS 738.9 obs. (736.8 calc.).

Scheme 2
Synthesis of 2-Substituted AE Derivatives

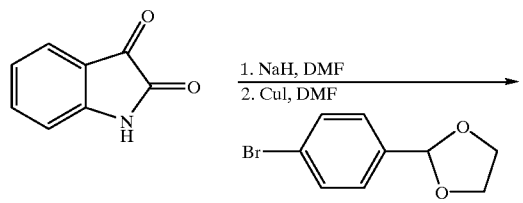

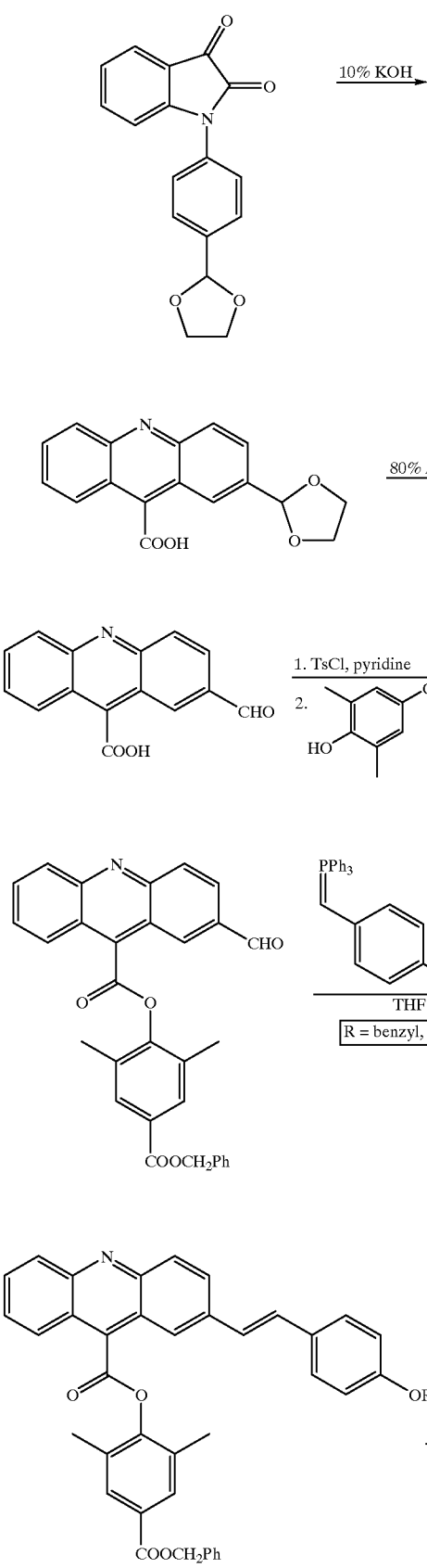
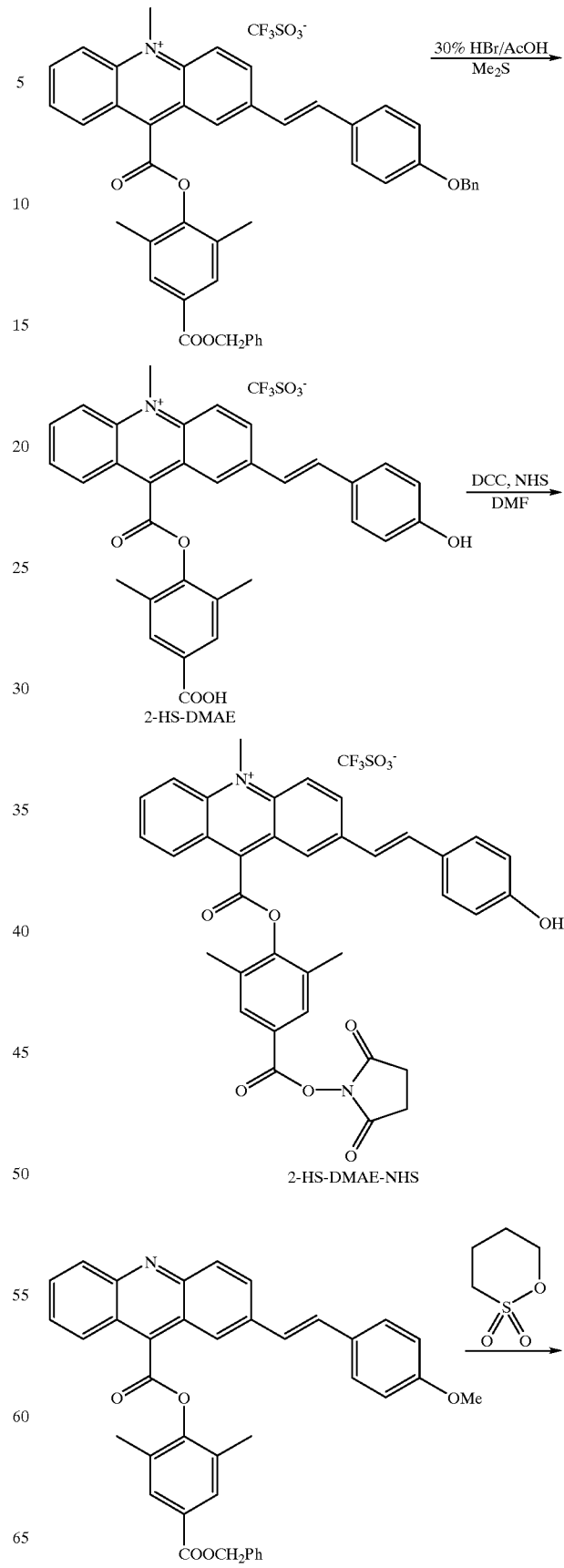

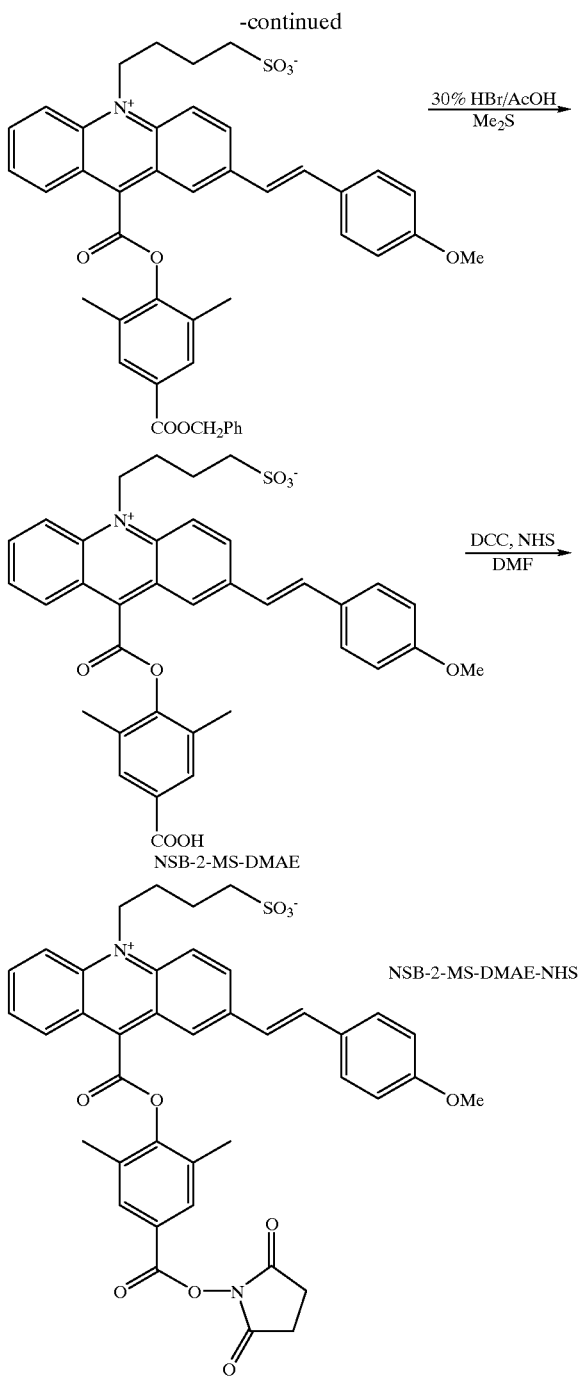

NSB-2-MS-DMAE

NSB-2-MS-DMAE-NHS

EXAMPLE 6

Synthesis of 2',6'-dimethyl-4'-carboxyphenyl 2-(4-hydroxyphenyl)-10-methyl-acridinium-9-carboxylate (2-HP-DMAE)

Synthesis of N-[3-(4-benzyloxyphenyl)phenyl]isatin

Isatin (0.12 g, 0.81 mmol) in anhydrous DMF (30 mL) was cooled in an ice-bath under nitrogen and treated with sodium hydride (21 mg, 1.1 equivalents). The reaction was stirred in ice for 0.5 hours and then warm ed to room temperature. This solution was then treated with 4-(3-bromophenyl)phenol benzyl ether (Hajduk et al. *Am. Chem. Soc.* 1997, 119, 5818–5827), (0.16 g, 0.47 mmol) followed by copper iodide (0.32 g, 1.68 mmol). The reaction was heated in an oil-bath at 140° C. After ~16 hours, the reaction was cooled to room temperature and concentrated under reduced pressure. The residue was dissolved in ethyl acetate (~75 mL) and filtered. The filtrate was concentrated under reduced pressure to afford a sticky, brown solid which was purified by preparative TLC on silica gel using 25% ethyl acetate in hexanes as the developing solvent. Rf (product)= 0.38. Yield =47 mg (25%); MADI-TOF MS 407.02 obs. (405.5 calc.); $^1$H-NMR (CDCl$_3$) 5.12 (s, 2H), 6.95 (d, 1H, J=8 Hz), 7.06 (d, 2H, J=8.8 Hz), 7.18 (t, 1H, J=7.5 Hz), 7.33–7.47 (m, 7H), 7.53 (d, 2H, J=8.8 Hz), 7.57–7.60 (m, 2H), 7.71 (d, 1H, J=7.5 Hz).

Synthesis of 3-(4-benzyloxyphenyl)-9-carboxyacridine

The alkylated isatin from above (47 mg) was suspended in 25 mL of 10% KOH and refluxed under nitrogen for 3 hours. The reaction was then cooled to room temperature and diluted with an equal volume of ice water. This was acidified with ~10% Hcl till pH 2. The yellow solid that separated out was collected by filtration and rinsed with ice water (3×5 mL). Following thorough air drying, the yellow solid was dissolved in methanol and the solution was evaporated to dryness. The residue was suspended in toluene and the resulting suspension was evaporate d to dryness. Yield=44 mg (94%). This material was us ed a such for the next reaction.

Synthesis of 2',6'-dimethyl-4'-benzyloxycarbonylphenyl 3-(4-benzyloxyphenyl)-acridine-9-carboxylate (3-BzP-DMAeE-Bz)

3-(4-Benzyloxyphenyl)-9-carboxyacridine (44 mg, 0.108 mmol) in anhydrous pyridine (20 mL) was cooled in an ice-bath under nitrogen and treated with 4-carboxybenzyl-2,6-dimethylphenol (33.3 mg, 1.2 equivalents) and p-toluenesulfonyl chloride (41 mg, 2 equivalents). The reaction was warmed to room temperature and stirred for 16 hours under nitrogen. It was then concentrated under reduced pressure and the residue was suspended in toluene (~25 mL) and evaporated to dryness. The recovered material was dissolved in chloroform (~2 mL) and the product was isolated by preparative TLC on silica gel using 25% ethyl acetate in hexanes as the developing solvent. Yield=22 mg (31%), MALDI-TOF MS 645.52 obs. (645.75 calc.).

Synthesis of 2',6'-dimethyl-4'-benzyloxycarbonylphenyl 3-(4-benzyloxyphenyl)-10-methyl-acridinium-9-carboxylate (3-BzP-DMAE-Bz)

The above ester (21 mg, 0.033 mmol) was dissolved in dichloromethane (1.5 mL) and treated with methyl trifluoromethanesulfonate (100 uL, 0.88 mmol). The reaction was stirred at room temperature for 16 hours. The solvent was then removed under reduced pressure and the residue was dissolved in MeCN (2 mL). HPLC analysis using a C18 column (3.9×300 mm) and a 30 minute gradient of 10→100% MeCN/water, each containing 0.05% TFA, at a flow rate of 1.0 mL/min. and UV detection at 260 nm showed products eluting at 20, 24, 25 and 29.5 minutes. These were isolated by preparative HPLC using a 20×300 mm column and the fractions were analysed by mALDI-TOF MS. The major product eluting at 24 minutes gave the correct molecular ion at 659.57 amu (660.78 calc.). The HPLC fraction containing this product, which was deep red in color, was evaporated to dryness. Yield=14 mg (65%).

Synthesis of 2',6'-dimethyl-4'-carboxyphenyl 3-(4-hydroxyphenyl)-10-methyl-acridinium-9-carboxylate (3-HP-DMAE)

The above benzyl protected acridinium ester (14 mg, 0.017 mmol) was stirred in a 1:1 mixture of methyl silfide and 30% Hbr in acetic acid at room temperature for 3.5 hours. Ether was then added to precipitate the product which was collected by filtration and rinsed with ether. The red product was dissolved in methanol. HPLC analysis as described above indicated clan product eluting at 16 minutes. This was isolated by preparative HPLC and the HPLC fraction was evaporated to dryness. Yield=2.6 mg (26%); MALDI-TOF MS 479.13 obs. (479.52 calc.).

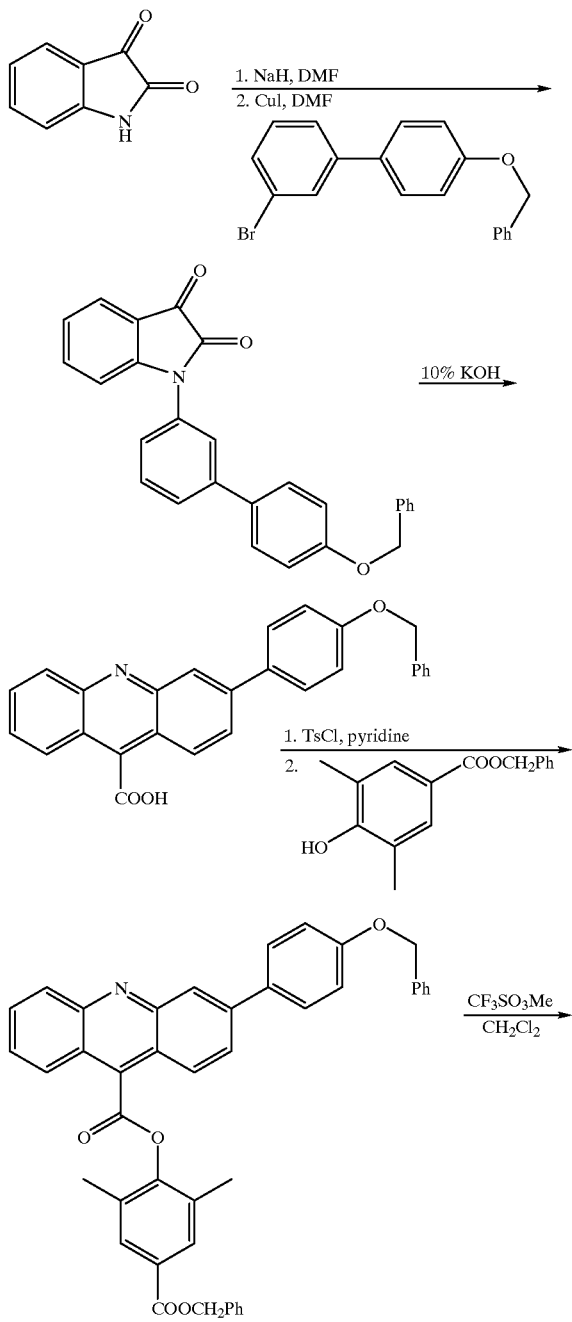

Scheme 3
Synthesis of 3-HP-DMAE

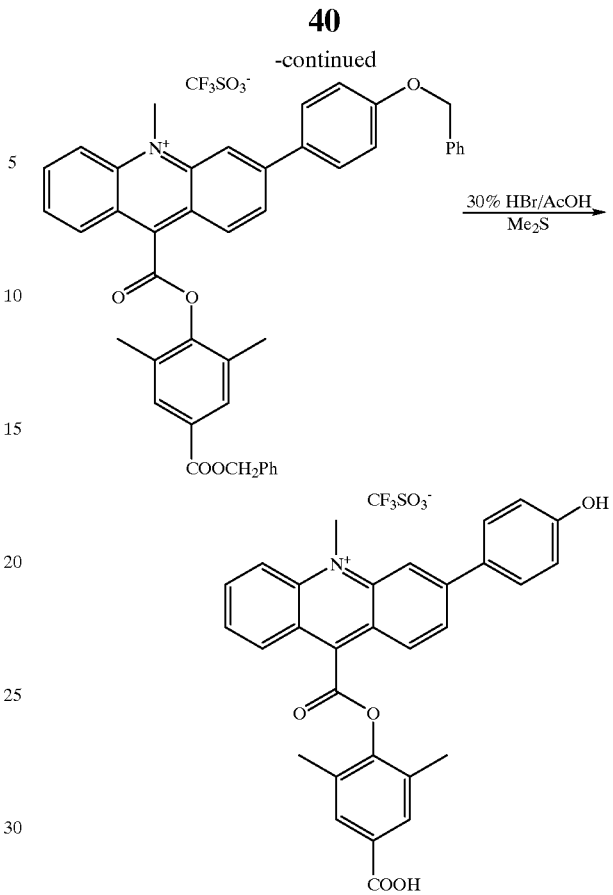

EXAMPLE 7

Synthesis of 2',6'-dimethyl-4'-carboxyphenyl 2-hydroxy-10-methyl-acridinium-9-carboxylate (2-OH-DMAE)

Synthesis of 4-Methoxyethoxymethoxy-iodobenzene

A solution of 4-iodophenol (10 g, 45.45 mmol) in 200 ml of anhydrous tetrahydrofuran was treated at 0° C. with sodium hydride (2.36 g, 60% dispersion, 59.09 mmol) for 5 minutes. To the resulting mixture was slowly added over a 5-minute period methoxyethoxymethyl chloride (8.3 ml, 72.73 mmol). The mixture was stirred at 0° C. for 30 minutes, warmed to room temperature, and stirred under nitrogen for 24 hours. The solvent was removed under reduce pressure. The residue was taken into 500 ml of ether, washed with 200 ml of 5% sodium hydroxide (4×200 ml), water (4×200 ml), saturated sodium chloride (1×200 ml), and dried over sodium sulfate. Evaporation of the solvent under reduced pressure gave an oily product in 14.1 g. TLC (silica gel, ether): Rf 0.5.

N-(4-Methoxyethoxymethoxy)phenyl isatin

A solution of isatin (4.0 g, 27.2 mmol) in 200 ml of anhydrous N,N-dimethylformaldehyde was treated at room temperature with sodium hydride (1.036 g, 60% dispersion, 32.64 mmol) for 0.5 hour, followed by addition of 4-methoxyethoxymethoxy-iodobenzene (12.57 g, 40.8 mmol) and copper (I) iodide (10.34 g, 54.4 mmol). The resulting mixture was stirred at 160° C. under nitrogen for 17 hours. It was cooled to room temperature, and diluted with 400 ml of chloroform. The resulting mixture was filtrated to remove the inorganic materials. The filtrate was evaporated under reduced pressure to give a crude mixture containing N-(4-methoxyethoxymethoxy)phenyl isatin as a major product. TLC (silica gel, ether): Rf 0.8.

2-Methoxyethoxymethoxy-acridine-9-carboxylic acid

The above crude 4-methoxyethoxymethoxyphenyl isatin, without purification, was suspended in 120 ml of 10% potassium hydroxide. The suspension was refluxed at 150° C. for 5 hours. After cooling to room temperature, the mixture was filtrated to remove the orange impurities. The filtrate was acidified in an ice-water bath with concentrated hydrochloric acid to pH 2. The resulting yellow precipitate was collected and washed with water (4×50 ml) and air-dried. The dried material was further washed with ether (6×50 ml) to yield the desired product in 6.7 g. TLC (silica gel, 30% methanol/chloroform): Rf 0.5.

2',6'-dimethyl4'-benzyloxycarbonylphenyl 2-methoxyethoxymethoxy-acdidine-9-carboxylate (2-MEM-DMAeE-Bz)

A suspension of 2-methoxyethoxymethoxy-acridine-9-carboxylic acid (3.6 g, 11 mmol) in 150 ml of anhydrous pyridine was treated with p-toluenesulfonyl chloride (4.183 g, 22 mmol) at 0° C. for 5 minutes to form a homogeneous brown solution. Then, benzyl 3,5-dimethyl-4-hydroxy-benzoate (2.818 g, 11 mmol) was added. The solution was stirred at room temperature under nitrogen for 20 hours. The solvent was removed under reduced pressure. The residue was separated on a silica flash chromatography column packed with hexane. It was eluted with 50% ether/hexane (1 liter) followed by 70% ether/hexane (3 liters). The product fraction was obtained from the 70% ether/hexane eluent. Evaporation of the solvents under reduced pressure gave 3.74 g of the desired product. TLC (silica gel, ether): Rf 0.8.

2',6'-dimethyl-4'-benzyloxycarbonylphenyl 2-hydroxy-10-methyl-acridinium-9-carboxylate trifluoromethanesulfonate (2-OH-DMAE-Bz)

A light-yellow solution of 2',6'-dimethyl-4'-benzyloxycarbonylphenyl 2-methoxyethoxymethoxy-acdidine-9-carboxylate (400 mg, 0.708 mmol) in 20 ml of anhydrous methylene chloride was treated with methyl trifluoromethanesulfonate (0.4 ml, 3.54 mmol) at room temperature under nitrogen with stirring for 14 hours. The resulting mixture was treated with anhydrous ether (20 ml). The precipitate was collected and washed with ether (4×20 ml) to yield 325 mg of the product. MS: (ESI): m/z 492.6 (M+). $^1$H NMR (300 MHz, MeOD-d$_4$/CDCl$_3$): δ 2.52 (6H, s), 5.01 (3H, s), 5.42 (2H, s), 7/37–7.51 (5H, m), 7.81 (1H, d, J=2.6 Hz), 7.97 (2H, s), 8.10 (1H, t, J=7.0 Hz), 8.16 (1H, dd, J$_1$=8.0 Hz, J$_2$=2.6 Hz), 8.42 (1H, t, J=7.0 Hz), 8.60 (1H, d, J=8.8 Hz), and 8.73 (2H, two overlapping doublets, J~8.0 Hz).

2',6'-dimethyl-4'-carboxyphenyl 2-hydroxy-10-methyl-acridinium-9-carboxylate bromide (2-OH-DMAE)

A solution of 2',6'-dimethyl-4'-benzyloxycarbonylphenyl 2-hydroxy-10-methyl-acridiniumn-9-carboxylate trifluoromethanesulfonate (100 mg) in 4 ml of 30% hydrogen bromide in acetic acid was stirred at 55° C. under nitrogen for 1 hour, and then treated with 10 ml of anhydrous ether. The resulting precipitate was collected and washed with ether (4×10 ml) to give 80 mg of (4-carboxyl-2,6-dimethyl) phenyl 2-hydroxy-10-methyl-acridinium-9-carboxylate bromide. MS (ESI): m/z 402.7 (M+). $^1$H NMR (300 MHz, CD$_3$CN/MeOD-d$_4$): δ 2.52 (6H, s), 4.95 (3H, s), 7.78 (1H, d, J=2.7Hz), 7.76 (2H, s), 8.10 (1H, t, J=7.0Hz), 8.13 (1H, dd, J$_1$=9.9 Hz, J$_{3=2}$=2.7 Hz), 8.40 (H, d t, J$_1$=2.7 Hz, J$_2$=8.0 Hz), 8.62 (1H, d, J=8.0 Hz), 8.77 (1H, d, J=9.2 Hz), and 8.78 (1H, d, J=9.9 Hz).

Scheme 4
Synthesis of 2-OH-DMAE

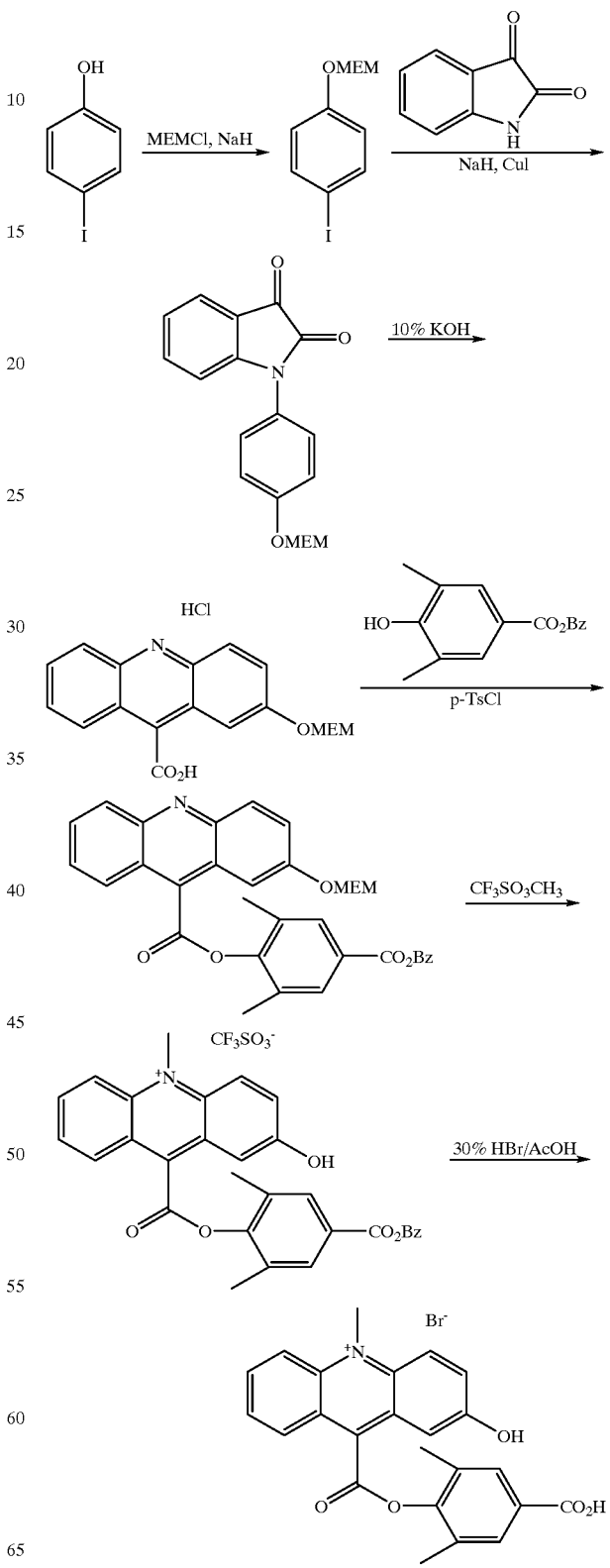

EXAMPLE 8

Synthesis of NSB-3-HS-DMAE-BSA conjugate

BSA (0.5 mg, 0.0075 umoles) in 0.1 M carbonate pH 9 (0.9 mL) was treated with a solution of NSB-3-HS-DMAE-NHS (0.25 mg, 0.35 umoles) in DMF (0.1 mL) dropwise. A clear solution resulted which was stirred at room temperature for ~16 hours. The labeled protein was isolated by column chromatography on Sephadex G25 using water as eluent. The protein fraction eluting in the void volume was collected and concentrated using an amicon filter (MW 30,000 cutoff). MALDI-TOF analysis of the conjugate indicated a mass increase of 1180 units corresponding to the incorporation of approximately 2 labels NSB-3-HS-DMAE per BSA.

EXAMPLE 9

Synthesis of NSB-3-HS-DMAE-anti-TSH conjugate

TSH antibody (0.5 mg, 3.33 nmoles) in 0.1 M carbonate pH 9 (0.45 mL) was treated with a solution of NSB-3-HS-DMAE-NHS (120 ug, 50 equivalents) in DMF (60 uL). The reaction was stirred at room temperature for 2 hours and then the labeled protein was isolated as described above. MALDI-TOF MS analysis the conjugate indicated a mass increase of 1796 units corresponding to the incorporation of approximately 3 labels per molecule of anti-TSH.

EXAMPLE 10

Synthesis of 3-HS-DMAE-BSA conjugate

BSA (2 mg, 0.03 umoles) in 0.1 M carbonate pH 9 (400 uL) was treated with a solution of 3-HS-DMAE-NHS (0.45 mg, 25 equivalents) in DMF (100 uL). The reaction, which was slightly turbid, was stirred at 4° C. for 16 hours. The conjugate was isolated as described above. MALDI-TOF MS analysis of the conjugate indicated a mass increase of 415 units corresponding to the incorporation of approximately one label per BSA.

EXAMPLE 11

Synthesis of NSB-3-MS-DMAE-BSA conjugate

BSA (0.5 mg, 0.0075 umoles) in 0.1 M carbonate pH 9 (400 uL) was treated with a solution of NSB-3-MS-DMAE-NHS (140 ug, 25 equivalents) in DMF (140 uL). The reaction was stirred at room temperature for 16 hours and then the conjugate was isolated as described above. MALDI-TOF MS analysis of the conjugate showed a mass increase of 3250 units corresponding to the incorporation of approximately 5 labels per BSA.

EXAMPLE 12

Synthesis of NSB-3-MS-DMAE-anti-TSH conjugate

TSH antibody (0.5 mg, 3.33 nmoles) in 0.1 M carbonate pH 9 (400 uL) was treated with a solution of NSB-3-MS-DMAE-NHS (120 ug, ~50 equivalents) in DMF (120 uL). The reaction was stirred at room temperature for 16 hours and then the conjugate was isolated as described earlier. MALDI-TOF MS analysis of the conjugate showed a mass increase of 6074 units corresponding to the incorporation of approximately 10 labels per TSH antibody.

EXAMPLE 13

Synthesis of 2-HS-DMAE-BSA conjugate

2-HS-DMAE (1.3 mg, 2 umoles) in MeCN (0.65 mL)+ DMF (0.1 mL) was treated with N-hydroxysuccinimide (1.4 mg, 12 umoles) and dicyclohexylcarbodiimide (3 mg, 14.6 umoles). The reaction was stirred at room temperature. After 2–3 hours HPLC analysis on a C18 column (3.9×300 mm) using a 30 minute gradient of 10→100% MeCN/water each containing 0.05% TFA at 1 mL/min. and UV detection at 260 nm) showed Rt (product)=18.2 min (>80%), Rt (sm)=17 min. The reaction was stirred for an additional hour and then the MeCN was removed under reduced pressure. The remainder was added dropwise to a solution of BSA (5 mg, 0.075 umoles) in 0.1 M carbonate pH 9 (0.5 mL) followed by additional DMF (0.2 mL). The reaction was stirred at room temperature for 1 hour and then centrifuged to remove insoluble material. The filtrate was purified by column chromatography on Sephadex G25 with water as eluent. The labeled protein eluting in the void volume was collected and concentrated by amicon filtration (MW 30,000 cutoff filter). MALDI-TOF MS analysis of the conjugate showed a mass increase of 2822 units corresponding to the incorporation of approximately 6 labels per BSA.

EXAMPLE 14

TSH Assay Comparison of DMAE and NSB-3-HS-DMAE as Tracer Labels

Conjugate binding functionality for diagnostic assay applicability was evaluated using a divalent sandwich immunoassay formulated for the clinical quantitation of TSH in serum. In this assay the NSB-3-HS-DMAE-antiTSH conjugate (henceforth referred to as a tracer) should bind specifically to the selected analyte, TSH, present in a patient sample or in TSH-containing standards (Chiron Diagnostics Corp., Walpole, Mass.), to form a noncovalently associating antibody-antigen complex. The resultant tracer-analyte complex is in turn captured by a second, polyclonal, sheep antiTSH antibody, covalently coupled to a paramagnetic particle solid phase. Chemiluminescent signal is determined following the magnetic separation of the solidphase-bound conjugate from unbound conjugate. Tracer qualification is assessed through two related methods; primarily, a comparative analysis of normalized standard curve data, generated for both the conjugate in question and also a DMAE-antiTSH tracer of previously established utility. The standard curve data were used to calculate the TSH concentration of several control samples. The NSB-3-HS-DMAE-antiTSH concentrate was diluted $8.96 \times 10^{-4}$-fold from 2.4 $\mu$M in ACS™ TSH3 Lite Reagent Buffer (Chiron Diagnostics Corp., Walpole, Mass.) to 2.15 nM, which was the concentration of the reference DMAE-antiTSH tracer supplied in the Chiron Diagnostics TSH3 Assay kit. The TSH assay was initiated when 100 uLs of the novel NSB-3-HS-DMAE-antiTSH tracer and 100 uLs of the reference DMAE-antiTSH kit tracer were mixed separately with 200 $\mu$Ls of either a TSH standard or control. Ten TSH standards were used, containing TSH in concentrations of 0.000, 0.120, 0.740, 1.92, 3.86, 8.99, 19.9, 49.6, 97.1 and 183 $\mu$I.U./mL (Chiron Diagnostics Corp., Walpole, Mass.). Six controls were also assayed. These were Ligands 1, 2 and 3 from Chiron Diagnostics, which contained TSH in mean concentrations of 0.600, 4.90 and 17.0 $\mu$I.U./mL, respectively, and Lyphochek® Immunoassay Control Serums 1, 2 and 3 from Bio-Rad Laboratories, which contained TSH in mean concentrations of 2.94, 11.5 and 40.6 $\mu$I.U./mL, respectively. The mixtures were collectively vortexed thrice for 5 seconds at setting no. 5 on a Coming, Inc. model 4010 Multi-Tube Vortexer. Data points were acquired in triplicate. The assay mixtures were then incubated for 20 minutes at room temperature, after which 200 uLs of ACS™ TSH3 Solid Phase (~67 μgs) was added to each assay. The assay mixtures were vortexed thrice as described above and incubated for 30 minutes at room temperature. The solid phase was magnetically separated from the supernatant by the 3 minute application of an array of permanent magnets in a Ciba-Corning Magic Lite Assay Rack. The supernatant was decanted from the solid phase. Residual supernatant was removed by blotting for 3 minutes and then again for 1 minute.

The solid phase was washed with two separate 1.0 ml volumes of Chiron Diagnostics ACS™:NG Wash Buffer and suspended in 100 μls of reagent grade water. The chemiluminescent reaction was initiated with the sequential addition of 300 μLs each of Chiron Diagnostics MLA Reagent 1 (0.1 NHNO$_3$, 0.5% H$_2$O$_2$) and Reagent 2 (0.25 NNaOH, 0.05% CTAC) on a Ciba-Corning Diagnostics Magic Lite Analyzer equipped with a Corion BG38 optical filter. Chemiluminescence data were collected as photons detected by the Magic Lite Analyzer and expressed in relative light units (RLUs).

Method of Calculation for Sandwich Assay Parameters.

Arithmetic means for RLUs resulting from a specific analyte concentration, represented here as μ, were calculated from three replicates. Non-tracer assay reagents also contribute a small though sometimes significant number of RLUs. Hence, a control reaction, containing all assay reagents except tracer, was run in parallel to determine non-tracer reagent background, represented here as n. Arithmetic mean RLUs, μ, were corrected to represent RLUs obtained from the tracer only, represented here as B, where B=μ-n. Where the analyte concentration was highest, the corrected arithmetic mean RLU value for that point was denoted as B$_{max}$. A direct but non-linear relationship exists between the analyte concentration present in the standard and the detected RLUs. Consequently, the same direct sigmoidal correlation also relates the analyte concentration to the resultant %B/B$_{max}$ and may be accurately expressed in the empirical linear form as $$y = y_0 + \frac{(y_\infty - y_0)}{(1 + 10^{-m\log x - b})}$$

where x is the analyte concentration, and y is the observed signal generated either as %B/B$_{max}$ or RLUs (Ref.A, B C).

A. Rodbard, David; *Ligand Analysis*; (1981); Langon, J.; Clapp, J. (Eds.); Masson Publishing, Inc., New York; pp 45–101.

B. Nix, Barry; *The Immunoassay Handbook*; (1994); Wild, David (Ed.); Stockton Press, Inc., New York; pp. 117–123.

C. Peterman, Jeffrey H.; *Immunochemistry of Solid-Phase Immunoassay*; (1991); Butler, J. (Ed.); CRC Press, Inc., Boca Raton; pp. 47–65.).

Additionally, there are four more parameters, namely the regression constant, b, the regression coefficient, m, the assymptotic nonspecific binding (NSB) at zero dose (analyte concentration), y$_0$, and the assymptotic infinite limit response for an infinitely high dose, y$_\infty$. The latter three of these parameters were calculated directly using the iterative, weighted, four-parameter logistic (4PL-WTD) analysis function of the DOSECALC.EXE Rev.1.73 program (Chiron Diagnostics Corp., Walpole, Mass.). The arithmetic mean of the regression constant b was determined over the entire range of analyte concentrations as calculated from the dose response expression re-written as $$b = -\log\frac{y_\infty - y}{y - y_0} - m\log x.$$

Analyte concentrations of unknowns were subsequently calculated using the dose response equation arranged as $$x = 10^{\frac{\log[(y_\infty - y)/(y - y_0)] + b}{-m}}.$$

TSH Assay Standard Curves Using NSB-3-HS-DMAE and DMAE as Tracer Labels.

Figure 3:
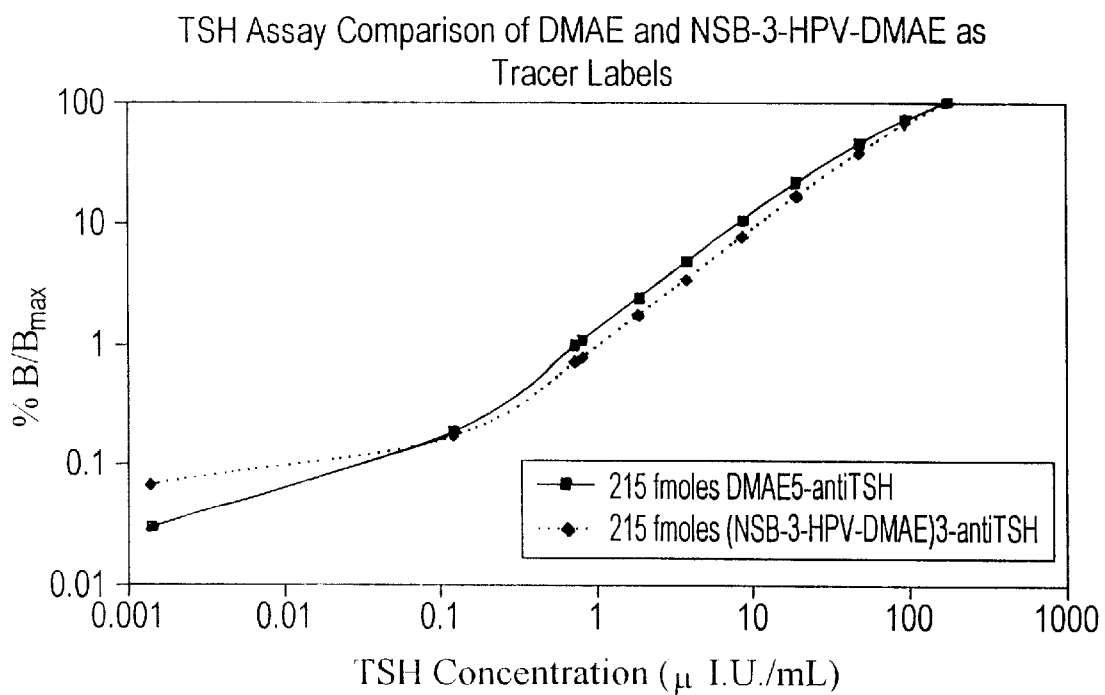
FIG. 3 shows the TSH Assay results discussed in Example 14.

Double logarithmic plots of %B/B$_{max}$ versus TSH concentration (see FIG. 3) illustrate the close similarity in the normalized standard curve shape generated by the NSB-3-HS-DMAE-antiTSH and DMAE-antiTSH conjugates. Therefore, indicating that the NSB-3-HS-DMAE label and other long emission wavelength acridinium ester labels have utility as immunoassay tracers over four or five orders of magnitude in analyte concentration: satisfactory in this case for the determination of TSH concentration over the its entire clinically relevant range.

Assay Accuracy in Determination of TSH Concentration.

TSH concentrations were calculated for the Ciba-Corning Ligands 1, 2 and 3, as well as, for the Bio-Rad Control Serums 1, 2 and 3 using the weighted 4PL function. The calculated values were compared to the established value ranges stated in the associated product literature. In all cases NSB-3-HS-DMAE displayed demonstrable utility as a tracer label for the accurate determination of TSH concentration in the indicated controls. Results were comparable to those associated with the DMAE label. NIR acridinium esters have practical utility as tracer labels in immunoassay.

| Expected vs. Determined TSH Concentration for TSH Controls | | | | | | |
|---|---|---|---|---|---|---|
| TSH Concentration (uI.U./ml) | Ciba-Corning Diagnostics Ligands | | | Bio-Rad Laboratories Control Sera | | |
| Levels | 1 | 2 | 3 | 1 | 2 | 3 |
| Expected Range | 0.50–0.70 | 4.20–5.60 | 14.0–20.0 | 2.34–3.54 | 9.10–13.9 | 35.6–45.6 |
| Determined | | | | | | |
| Using DMAE label | 0.607 | 4.48 | 17.5 | 2.84 | 10.8 | 35.9 |
| Using NSB-3-HS-DMAE label | 0.688 | 4.95 | 19.3 | 3.32 | 12.0 | 41.1 |

EXAMPLE 15

Synthesis of 2',6'-dimethyl-4'-(N-succinimidyloxycarbonyl)phenyl 2-hydroxy-10-methyl-acridinium-9-carboxylate (2-OH-DMAE-NHS)

A solution of 2',6'-dimethyl-4'carboxyphenyl 2-hydroxy-10-methyl-acridinium-9-carboxylate (3.5 mg, 6.35 umoles) in anhydrous DMF (0.5 mL) was treated with N-hydroxysuccinimide (3.7 mg, 5 equivalents) and dicyclohexylcarbodiimide (6.5 mg, 5 equivalents). The reaction was stirred at room temperature. After 5–6 hours, HPLC analysis using a C18 column (3.9×300 mm) and a 30 minute gradient of 10→100% MeCN/water, each containing 0.05% TFA, at a flow rate of 1.0 mL/min. and UV detection at 260 nm, indicated complete conversion; Rt (product)=15 min., Rt (starting acid)=14 min. The product was isolated by preparative HPLC using a 20×300 mm column and the HPLC fraction containing the product was lyophilized to dryness. Yield=3 mg (75%). This material as used as such for the following labeling reaction.

EXAMPLE 16

Dual Acridinium Ester-label Hybridization Assay
A. Oligonucleotide Labelings
2-OH-DMAE-Vanco A Probe 526.20 (SEQ ID NO 1):

A 20-mer synthetic oligonucleotide containing the following Vancomycin A probe sequence 5'-XCG CAA GGT TTT TCG CAC ATT (SEQ ID NO 7) was synthesized using standard phosphoramidite chemistry. An amino group was introduced at the 5' end using Clontech's 'Unilink' aminomodifier (X in the above sequence). Ten nmoles of this oligonucleotide in 0.3 mL of 0.1 M sodium bicarbonate, pH 8.5 was chilled in ice and treated with a DMF solution of the above NHS ester (3×500 nmoles, 1 mg total) in three equal portions of 70 uL each. The reaction was stirred at room temperature for 16 hours and then the labeled DNA was separated from free label by gel-filtration on a Sephadex G25 column. The labeled DNA eluting in the void volume of the column was collected and further purified by preparative HPLC on a C18 column (3.9×300 mm) and a gradient of 8→20% in 20 minutes followed by a 20→60% gradient in 20 minutes of MeCN in 0.1 M trimethylammonium acetate pH 7.3. The conjugate eluted at 16 minutes and was collected and lyophilized to dryness. Yield=1.73 nmoles (17%), MALDI-TOF MS 6678.5 obs. (unmodified oligonucleotide 6292.7) indicated the expected incorporation of one label. Specific activity of the label was found to be unchanged from that of the free label at $0.45 \times 10^{19}$ RLUs/mole.

DMAE-Vanco B Probe 495.23 (SEQ ID NO 2):

The synthesis of the amino-linked Van B probe sequence and DMAE labeling were carried out in the same manner as in the preceding paragraph.

B. Immobilization of Oligo-deoxyribonuctides onto Amino-PMP.

All reactions were performed at room temperature unless noted otherwise. PMP coated with the aminoethylaminopropyl siloxane polymer (Amino-PMP, 0.59 mL of 50.8 mg/mL, 30 mgs) was magnetically separated from its storage buffer with the application of a strong permanent magnet (ten minutes, Industrial Magnetics, Inc. model 5C3894). The storage buffer was removed by aspiration. The amino-PMP was washed sequentially with four separate volumes (10 ml) of 10 mM prydine by mixing (ten minutes, setting 5 on a Corning, Inc. model 4010 Multi-Tube Vortexer) and magnetic separation (ten minutes) for each wash cycle. Glutaraldehyde (5% (w/v) in 10 mM pyridine, 10 mLs) was mixed (setting 3, three hours) with the amino-PMP suspension. Unreacted glutaraldehyde was removed with four wash cycles of 10 mM pyridine (40 ml total). Thirty O.D. of 5'-amino-linked oligomer was coupled in 415 uLs 10 mM pyridine. The reaction mixtures were mixed in an end-over-end shaker (Lab Industries, Inc. model 400–100) for 16 hours. The supernatant was removed and the oligo-PMPs were treated with 10 mLs of 100 mM sodium cyanoborohydride for four hours. The oligo-PMPs were washed five-fold with 1.0 mL of water and then deprotected with 2.0 mLs of concentrated ammonium hydroxide for 16 hours at 55° C. The supernatant was removed and the oligo-PMPs were washed with 1.0 mL of water and resuspended in 1.0 mL of water. (Vanco-A PMP-Probe 557.22 is designated as SEQ ID NO 3. Vanco B PMP-Probe 496.20 is designated as SEQ ID NO 4.)

C. Dual-Analyte Probe Assay:
Assay Set Up:

In preparation for the assay several buffers were prepared: Hybridization Buffer (0.60 M sodium chloride, 60 mM citric acid, 10 mM Tris, 1.0 mM EDTA, 0.10% (w/v) bovine serum albumin, 0.020% (v/v) Tween-20, 0.020% (w/v) sodium azide, 1.0 % (w/v) dextran sulfate, pH 8.0), Probe Diluent (50 mM sodium phosphate, pH 6.0), Wash Solution (0.30 M sodium chloride, 30 mM citric acid, 0.10% (w/v) sodium dodecyl sulfate, pH7.7) and DNase I Solution (10 mM Tris, 1.0 mM EDTA, 10 mM magnesium chloride, 3.3 µg/mL DNase I, pH 8.0). Solid phases and synthetic targets were diluted to the indicated working concentrations in Hybridization Buffer, while the probes were diluted in Probe Diluent. A hybridization reaction mixture was set up (See FIG. 4) so as to contain 12.5 µLs of 80 nM 2-OH-DMAE-Vanco A-Probe 526.20 (1.0 pmole) (SEQ ID NO 1), 12.5 µLs of 1.6 nM DMAE-Vanco B-Probe 459.23 (0.10 pmole) (SEQ ID NO 2), 100 µLs of 2.0 mg/mL Vanco-A PMP-Probe 557.22 solid phase (0.20 mgs) (SEQ ID NO 3), 100 µLs of 0.20 mg/mL VancoB PMP-Probe 496.20 (20 µgs) (SEQ ID NO 4), 75 µLs of both Vanco A 526.53 (SEQ ID NO 5) and Vanco B 459.57 (SEQ ID NO 6) synthetic targets at concentrations of $10^{-8}$, $5 \times 10^{-9}$, $10^{-9}$, $5 \times 10^{-10}$, $10^{-10}$ and 0 M. (Note that Vanco is also referred to herein as Van.) Whereupon the mass of target in each test was either 750, 375, 75, 37.5, 7.5 and 0.000 fmoles, otherwise represented as $4.5 \times 10^{11}$, $2.3 \times 10^{11}$, $4.5 \times 10^{10}$, $2.3 \times 10^{10}$, $4.5 \times 10^{9}$, and 0 molecules. While the simultaneous assay reactions were constituted as indicated above, the individual assays for each analyte contained the complementary probe only, the other being substituted with Probe Diluent. The assay mixtures were vortexed thrice for five seconds at setting number five on a Coming, Inc. model 4010 Multi-Tube Vortexer. The reaction mixtures were incubated at 45° C. for thirty minutes. The solid phase was magnetically separated from the supernatant by the three minute application of an array of permanent magnets in a Ciba Corning Magic Lite Assay Rack. The supernatant was decanted from the solid phase. Residual supernatant was removed by blotting for three minutes and then again for one minute. The solid phase was washed with two separate 1.0 mL volumes of Wash Solution to remove unbound probe and then suspended in 300 µLs of DNase I Solution to release the probe from the solid phase surface. The chemiluminescent reaction was initiated under the control of the Dual PMT luminometer with the sequential addition of 300 µLs Chiron Diagnostics ACS Reagent 1 (0.1 N nitric acid, 0.5% (w/v) hydrogen peroxide) followed 0.1 seconds later with the addition of 300 µLs of ACS Reagent 2 (0.25 N sodium hydroxide, 0.5% (w/v) N,N,N,N-hexadecyltrimethylammonium chloride surfactant). Chemiluminescence data were collected as quanta detected by the Dual PMT Fixture for 2.0 seconds immediately following the addition of Reagent 2 and were expressed in relative light units (RLUs). (The target and probe sequences shown in FIG. 4 do not show the entire structure for the compounds. Specifically, the cross-linkers between the nucleic acid sequence and the label (or PMP) is omitted. The description above provides detailed information about the cross-linkers.)

Instrumentation:

The Dual-PMT luminometer has been described in U.S. Pat. Nos. 5,395,752 and 5,447,687. For the present application, the two photomultiplier tubes (PMTs) on the Dual PMT luminometer were each equipped with a separate and different optical filter. Cross-talk values were determined from 25 µLs of each probe solution. The arithmetic means of five replicates were totaled from both PMTs, where T=(mean RLUs from PMT1)+(mean RLUs from PMT2). Cross-talk for 2-HO-DMAE chemiluminescence on PMT1 was calculated as (PMT1 RLUs from 2-HO-DMAE-Van A)×100/T. Cross-talk for DMAE chemiluminescence on PMT2 was calculated as (PMT2 RLUs from DMAE-Van B)×100/T. The short wavelength channel, here designated as PMT1, was fitted with a Corion, Inc. BG-12-S-0939-4M229 optical filter through which wavelengths from 350 nm to 475 nm are transmitted by better than 20% of incident light. Consequently, the BG-12-S-0939-4M229 filter will transmit only 3.5% (cross-talk) of the total light emitted by the 2-HO-DMAE-Van A probe. Therefore, chemiluminescent signal from DMAE is preferentially detected by PMT1. The long wavelength channel, here designated as PMT2, was fitted with a Corion, Inc. LL-550-F-950B optical filter, which transmits light wavelengths from 560 nm and longer at approximately 90% of incident light. As a result, the LL-550-F-950B filter will transmit only 1.1% (cross-talk) of the total light emitted by the DMAE-Van B probe. Therefore, chemiluminescent signal from 2-HO-DMAE is preferentially detected by PMT2. As evidenced with the low cross-talk percentages, the Dual PMT luminometer equipped with these optical filters provides excellent discrimination of the separate chemiluminescent signals from a combined sample of DMAE- and 2-HO-DMAE-labeled probes.

Figure 5:
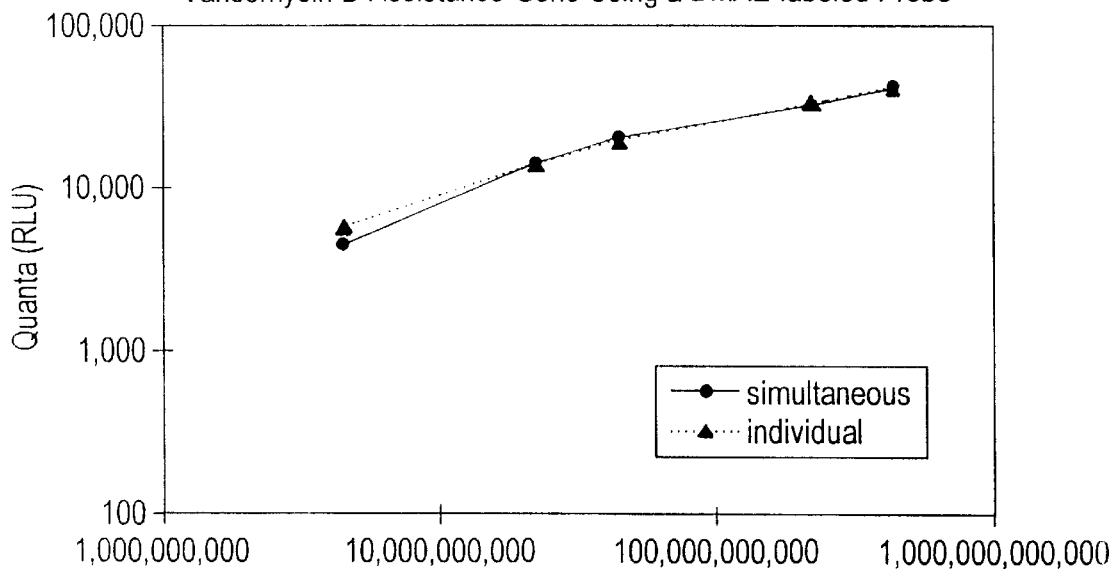
FIG. 5 shows the results of the hybridization assay for Vancomycin A resistance gene discussed in Example 16.
Figure 6:
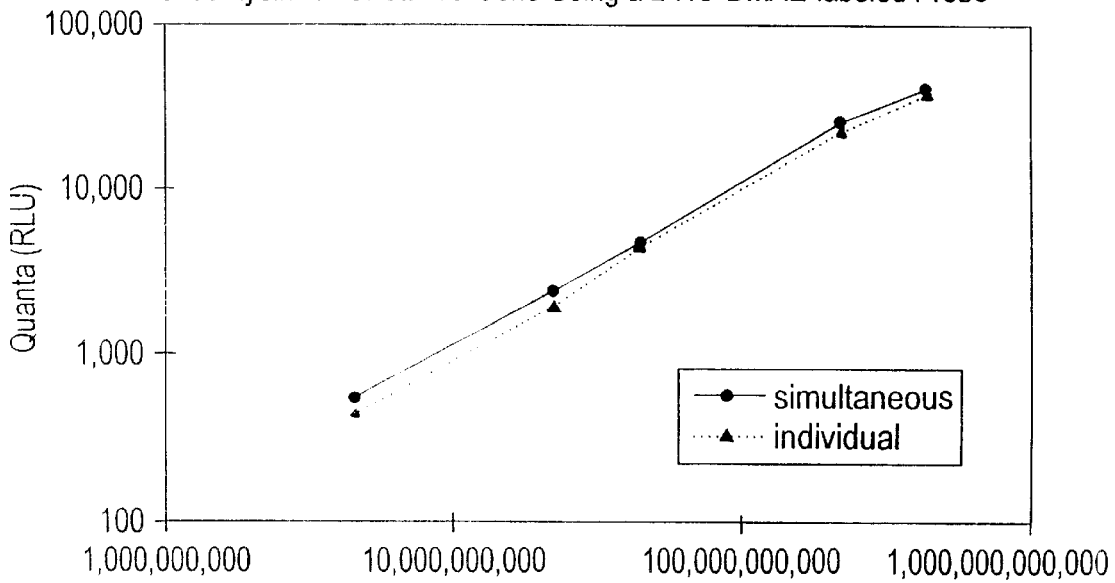
FIG. 6 shows the results of the hybridization assay for Vancomycin B resistance gene discussed in Example 16.

Results:

Besides the AE-labeled probe other assay reagents also contribute a small though sometimes significant number of RLUs. Hence, a control reaction, containing all assay reagents except probe, was run in parallel to determine non-probe reagent background, represented here as n. Mean RLUs from three replicates, $\mu$, were corrected to represent RLUs obtained from the probe only, represented here as B, where B=$\mu$-n. Results have been tabulated and are shown below. Double-log plots were generated for background corrected RLUs versus target number. As illustrated in the two graphs below (see FIGS. 5 and 6), the standard curves are identical for both the individual Van A assay and the simultaneous Van A and B assay using chemiluminescence generated by the 2-HO-DMAE-labeled Van A probe. Similarly, the standard curves are also identical for both the individual Van B assay and the simultaneous Van A and B assay using chemiluminescence generated by the DMAE-labeled Van B probe. The identical shapes of the standard curves in both the individual and dual analyte assays indicate that the mixed DMAE- and 2-HO-DMAE-labeled probes hybridize independently to their respective target sequences and are not perturbed by the presence of non-related, dual assay components. These results along with the excellent discrimination of the short and long wavelength chemiluminescent signals on the Dual PMT luminometer demonstrate the practicality of using two AE-labeled probes with optically discernible chemiluminescent emission maxima to simultaneously quantify two distinct analytes within the same sample.

| | Quanta (RLUs) | |
|---|---|---|
| Target Number | Individual | Simultaneous |
| Individual and Simultaneous Hybridization Assays for Vancomycin A Resistance Gene Using a 2-HO-DMAE-labeled Probe | | |
| 0 | 93 | 89 |
| 4,500,000,000 | 453 | 563 |
| 23,000,000,000 | 1,981 | 2,491 |
| 45,000,000,000 | 4,502 | 4,820 |
| 230,000,000,000 | 22,208 | 25,209 |
| 450,000,000,000 | 37,171 | 40,239 |
| Individual and Simultaneous Hybridization Assays for Vancomycin B Resistance Gene Using a DMAE-labeled Probe | | |
| 0 | 339 | 468 |
| 4,500,000,000 | 5,663 | 4,449 |
| 23,000,000,000 | 13,743 | 13,970 |
| 45,000,000,000 | 18,815 | 19,875 |
| 230,000,000,000 | 32,065 | 30,396 |
| 450,000,000,000 | 38,591 | 38,771 |

We claim:

1. An acridinium compound emitting light having wavelength maxima longer than 590 nm, said compound comprising an extended, coplanar, conjugated system, formed by the attachment of a functional group on the acridinium nucleus, said system maintaining coplanarity during light emission, said functional group comprising at least one aromatic ring and one electron-donating atom or group, wherein said functional group is attached to C-3 or C-1 position of the acridinium nucleus, said compound with the functional group attached at the C-3 position having the following structure:

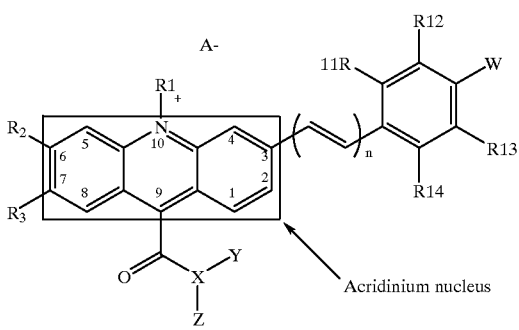

Acridinium nucleus wherein $R_1$ is an alkyl, alkenyl, alkynyl or aralkyl containing 0–20 heteroatoms;

$R_2$ and $R_3$ are identical or different, selected from hydrogen, R, substituted or unsubstituted aryl, wherein said substituents are selected from the group consisting of halide, amino, hydroxyl, nitro, sulfonate, —CN, —COOH, —SCN, —OR, —SR, —SSR, —C(O)R, —C(O)OR, —C(O)NHR, and —NHC(O)R;

R is selected from the group consisting of alkyl, alkenyl, alkynyl, aryl, and aralkyl containing 0–20 heteroatoms;

Alternatively, $R_2$ and $R_3$ can be bridged, so as to form an additional ring, fused to the attached acridinium nucleus;

$C_2$, $C_4$, $C_5$ peri-positions of the acridinium nucleus are optionally substituted;

n=1–4;

W is an electron-donating group;

$R_{11}$, $R_{12}$, $R_{13}$ and $R_{14}$ can be the same as $R_2$ or $R_3$; with either $R_{11}$ and $R_{12}$, or $R_{13}$ and $R_{14}$ optionally linked as in $R_2$ and $R_3$ to form additional aromatic and/or heterocyclic ring fused to the attached phenyl ring;

$A^-$ is a counter ion which is introduced to pair with the quarternary nitrogen of the acridinium nucleus;

X is nitrogen, oxygen or sulfur;

such that when X is oxygen or sulfur, Z is omitted and Y is a polysubstituted aryl moiety of the formula:

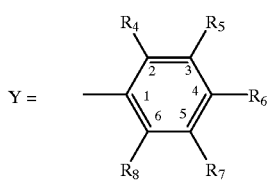

where $R_4$ and $R_8$ are alkyl, alkenyl, alkynyl, alkoxyl (—OR), alkylthiol (—SR), or substituted amino groups that serve to stabilize the -COX- linkage between the acridinium nucleus and the Y moiety, through steric and/or electronic effect;

$R_5$ and $R_7$ are any of $R_2$ and $R_3$ defined above;

$R_6$=—$R_9$—$R_{10}$ the key substituent containing necessary functional group for conjugating to biological molecule of interest, where $R_9$ is not required but optionally can be branched or straight-chained alkyl, substituted or unsubstituted aryl or aralkyl containing 0–20 heteroatoms, and $R_{10}$ is a leaving group or an electrophilic functional group attached with a leaving group selected from the group consisting of:

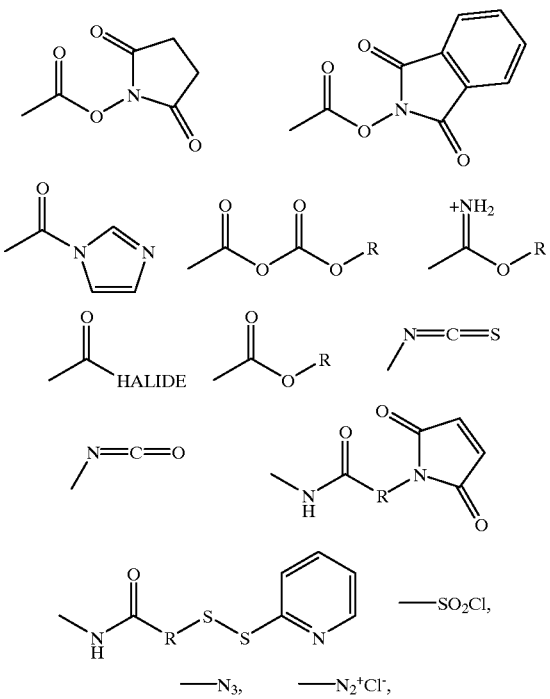

a halide, —COOH, —Q—R—Nu, —Q—R—(I)nNu—, —Q—Nu, —R—Nu, and —Nu, where n is a number of at least 1, Nu is a nucleophilic group, Q is a functional linkage, I is an ionic or ionizable group;

$R_5$ and $R_6$, and $R_6$ and $R_7$ are interchangeable; and when X is nitrogen, then Z is —$SO_2$—Y', Y' has the same definition of Y as described above, and both can be the same or different; Y itself can be a branched or straight-chained alkyl containing optionally up to 20 carbon atoms, halogenated or unhalogenated, or a substituted aryl, or heterocyclic ring system;

and said compound with the functional group attached at the C-1 position being the same except that the functional group is attached to the C-1 position of the acridinium nucleus.

2. The compound of claim 1, wherein said light is emitted upon reaction with hydrogen peroxide, sodium peroxide, or bivalent peroxide salts.

3. The compound of claim wherein said compound is selected from the group consisting of 3-HS-DMAE, NSB-3-HS-DMAE, NSP-3-HS-DMAE, and their corresponding ester, amide, carbonyl halide, and anhydride derivatives of the free carboxylate group.

4. An acridinium compound of claim 1 conjugated to a small organic biomolecule, macromolecule, viral particle, sub-cellular component, or entire cell, said conjugation being either by direct covalent bonding between the acridinium compound and the small organic biomolecule, macromolecule, viral particle, entire cell, or sub-cellular component or by indirect covalent bonding through a spacer.

5. An acridinium compound of claim 4 where the conjugation is through a spacer and the spacer is provided by a bifunctional cross-linker.

6. An acridinium compound of claim 4 where the macromolecule is selected from the group consisting of protein, peptide, inactivated protein, DNA, RNA, oligonucleotide, polysaccharide, oligosaccharide, glycoprotein, glycosamino glycan, lectin, lipoprotein, lipopolysaccharide, hormone, toxin, and cytokine.

7. An acridinium compound of claim 6 where the protein is selected from the group consisting of antibody, antibody fragment, avidin, streptavidin, allergen, receptor protein, DNA binding protein, viral antigen, bacterial antigen, eukaryotic antigen, immunoglobulin binding protein, and enzyme.

8. An acridinium compound of claim 4 where the sub-cellular component is ribosome and the entire cell is selected from the group consisting of bacterial and eucaryotic cells.

9. An acridinium compound of claim 4 where the small organic biomolecule is a hapten, ligand, or biologically active molecule.

10. An acridinium compound of claim 9 where the hapten is a thyroid hormone, steroid, vitamin, antibiotic, enzyme cofactor, therapeutic drug, metabolite, lipid, neurotransmitter, or controlled chemical substance.

11. The compound of claim 1 wherein:

n=1;

EWG is selected from the group consisting of —$NO_2$, —NO, —CN, —CHO, —C(O)R, $^+$NR'R"R'", —COOR, —COOH, —S(O)R, —$SO_2$R, —$SO_2$OR, —$SO_2$NHR, —$SO_2$NR'R", —$SO_2$OH and F;

W=$^-$OH, $^-$SH, $^-$NR'R"

$A^-$ is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$;

$R_4$ and $R_8$ are methyl or low alkyl;

$R_1$ is methyl or sulfoalkyl.

12. The compound of claim wherein W is an ionizable group that can donate an electron pair.

13. The compound of claim 12 wherein W is selected from the group consisting of OH, SH, NR'R", and —CH(EWG)$_m$ where m=1 or 2 and EWG is an electron withdrawing group; R', R" and R'" are hydrogen or low alkyl and can all be the same or different.

14. An assay for the detection or quantitation of an analyte, said assay comprising the use of the conjugated biological molecule of claim 4 as a label.

15. An assay for the simultaneous detection of multiple analytes comprising the use of conjugated biological molecules of claim 4 as labels.

16. The assay of claim 15 wherein two or more said conjugated biological molecules are used, and wherein said conjugated biological molecules allow the discrimination of their wavelengths and magnitude, and wherein differences in said magnitude can be correlated to the amounts of said various analytes present.

17. The assay of claim 15 for the determination of 2 analytes, wherein two of said conjugated biological molecules are used, and wherein said conjugated biological molecules luminesce at two different wavelength maxima, which allow discrimination of their signals and magnitude, which in turn can be correlated to the amounts of said two analytes present.

* * * * *

UNITED STATES PATENT AND TRADEMARK OFFICE
CERTIFICATE OF CORRECTION

PATENT NO. : 6,355,803 B1
DATED : March 12, 2002
INVENTOR(S) : Anand Natrajan et al.

It is certified that error appears in the above-identified patent and that said Letters Patent is hereby corrected as shown below:

Column 1,
Line 39, "front" should read -- from --;

Column 2,
Line 23, "naphthylmoieties" should read -- naphthyl moieties --;

Column 3,
Line 2, "Then" should read -- When --;

Column 11,
Line 10, "4-ethoxybenzyltriphenylphosphonium" should read
-- 4-methoxybenzyltriphenylphosphonium --;
Line 52, delete "30";

Column 16,
Line 65, "to heteroatoms," should read -- to 20 heteroatoms, --;

Column 24,
Line 2, "(5g)" should read -- (~5g) --;

Column 26,
Line 41, "(15mg)" should read -- (~15mg) --;

Column 37,
Line 64, "warm ed" should read -- warmed --;
Line 66, "*Am. Chem.*" should read -- *J. Am. Chem.* --;

Column 38,
Line 24, "evaporate d" should read -- evaporated --;
Line 25, "us ed a such" should read -- used as such --;
Line 57, "mALDI-" should read -- MALDI- --;

Column 41,
Line 18, "2',6'-dimethyl4'-benzyloxycarbonylphenyl" should read -- 2',6'-dimethyl-4'-benzyloxycarbonylphenyl --;
Lines 19 and 40, "acdidine" should read -- acridine --;
Line 66, "(H, d t, $J_1$=2.7 Hz, $J_2$=8.0" should read -- (1H, d t $J_1$=2.7 Hz, $J_2$=8.0 --;

UNITED STATES PATENT AND TRADEMARK OFFICE
CERTIFICATE OF CORRECTION

PATENT NO. : 6,355,803 B1
DATED : March 12, 2002
INVENTOR(S) : Anand Natrajan et al.

It is certified that error appears in the above-identified patent and that said Letters Patent is hereby corrected as shown below:

Column 43,
Line 44, "25" should read -- ~25 --;

Column 44,
Line 38, "solidphase-bound" should read -- solid phase-bound --;

Column 45,
Line 6, "Ciba-Coming" should read -- Ciba-Corning --;

Column 47,
Line 28, "8→20%" should read -- 8->20% --;
Line 28, "20→60%" should read -- 20->60% --;

Column 48,
Line 34, "Coming, Inc." should read -- Corning, Inc. --;

Column 55,
Line 15, "claim wherein" should read -- claim 1, wherein --; and

Column 56,
Line 17, "claim wherein" should read -- claim 1, wherein --.

Signed and Sealed this

Fourth Day of October, 2005

JON W. DUDAS
*Director of the United States Patent and Trademark Office*

SEQUENCE LISTING

<160> NUMBER OF SEQ ID NOS: 7

<210> SEQ ID NO 1
<211> LENGTH: 20
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO A 2-OH-DMAE-PROBE 526.20 (TRACER) IN
      EXAMPLE 16

<400> SEQUENCE: 1
cgcaaggttt ttcgcacatt                                              20

<210> SEQ ID NO 2
<211> LENGTH: 23
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO B DMAE-PROBE 459.23 (TRACER) IN EXAMPLE
      16

<400> SEQUENCE: 2
ttttgtaaga atgtaggcca gtg                                              23

<210> SEQ ID NO 3
<211> LENGTH: 52
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO A PROBE 557.22 (ON PMP) IN EXAMPLE 16

<400> SEQUENCE: 3
ggaggaggag gaggaggagg aggagctagt cagctgaata gcaattgtcg tt              52

<210> SEQ ID NO 4
<211> LENGTH: 50
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO B PMP-PROBE 496.20 (ON PMP) IN EXAMPLE 16

<400> SEQUENCE: 4
ggaggaggag gaggaggagg aggaggaagt tcatttgaaa ttcggggacg                 50

<210> SEQ ID NO 5
<211> LENGTH: 53
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO A SYNTHETIC TARGET 526.53 IN EXAMPLE 16

<400> SEQUENCE: 5
aatgtgcgaa aaaccttgcg cggaatggga aaacgacaat tgctattcag ctg             53

<210> SEQ ID NO 6
<211> LENGTH: 57
<212> TYPE: DNA
<213> ORGANISM: Homo sapiens
<220> FEATURE:
<221> NAME/KEY: misc_feature
<222> LOCATION: (223)...(223)
<223> OTHER INFORMATION: VANCO B SYNTHETIC TARGET 459.57 IN EXAMPLE 16

<400> SEQUENCE: 6
cactggccta cattcttaca aaaaatgcgg gcatcgccgt ccccgaattt caaatga         57

<210> SEQ ID NO 7
<211> LENGTH: 20
<212> TYPE: DNA
<213> ORGANISM: Homo sapiens
<220> FEATURE:
<221> NAME/KEY: misc_feature
<222> LOCATION: (223)...(223)

-continued

<223> OTHER INFORMATION: VANCO A PROBE 526.20 IN EXAMPLE 16

<400> SEQUENCE: 7
cgcaaggttt ttcgcacatt                    20